(12) United States Patent
Kato et al.

(10) Patent No.: US 9,163,254 B2
(45) Date of Patent: Oct. 20, 2015

(54) RECOMBINANT DNA MOLECULE ENCODING 5′ UTR CAPABLE OF PREVENTING INHIBITION OF TRANSLATION UNDER ENVIRONMENTAL STRESSES

(75) Inventors: Ko Kato, Kizugawa (JP); Shigehiko Kanaya, Ikoma (JP); Hideyuki Matsuura, Toyonaka (JP); Shinya Takenami, Yokohama (JP); Tatsuya Nosho, Ikoma (JP); Yuhki Kubo, Ikoma (JP); Kiyotaka Ueda, Ikoma (JP)

(73) Assignee: National University Corporation Nara Institute of Science and Technology, Nara (JP)

( * ) Notice: Subject to any disclaimer, the term of this patent is extended or adjusted under 35 U.S.C. 154(b) by 609 days.

(21) Appl. No.: 13/391,069

(22) PCT Filed: Aug. 19, 2010

(86) PCT No.: PCT/JP2010/064006
§ 371 (c)(1),
(2), (4) Date: Feb. 17, 2012

(87) PCT Pub. No.: WO2011/021666
PCT Pub. Date: Feb. 24, 2011

(65) Prior Publication Data
US 2012/0174256 A1    Jul. 5, 2012

(30) Foreign Application Priority Data

Aug. 19, 2009  (JP) ................................. 2009-190179
Mar. 11, 2010  (JP) ................................. 2010-054891

(51) Int. Cl.
*C12N 15/82* (2006.01)
*C12N 15/67* (2006.01)
*C12N 15/113* (2010.01)

(52) U.S. Cl.
CPC .......... *C12N 15/8273* (2013.01); *C12N 15/113* (2013.01); *C12N 15/67* (2013.01); *C12N 15/8216* (2013.01)

(58) Field of Classification Search
None
See application file for complete search history.

(56) References Cited

U.S. PATENT DOCUMENTS

2006/0150283 A1*  7/2006  Alexandrov et al. ......... 800/288
2012/0174256 A1   7/2012  Kato et al.
(Continued)

FOREIGN PATENT DOCUMENTS

| WO | 98/21321    | 5/1998 |
| WO | 98/37189    | 8/1998 |
| WO | 2011/021666 | 2/2011 |

OTHER PUBLICATIONS

Papdi et al. Functional identification of Arabidopsis stress regulatory genes using the controlled cDNA overexpression system. Plant Physiology. 2008. 147: 528-542.*

(Continued)

*Primary Examiner* — Anne Kubelik
*Assistant Examiner* — Ashley K Buran
(74) *Attorney, Agent, or Firm* — Wenderoth, Lind & Ponack, L.L.P.

(57) ABSTRACT

An object of the present invention is to identify sequence features of the 5′ UTR, which are involved in changes in the translational state of plants under environmental stresses, and to provide a recombinant DNA molecule, an expression vector, a transformant, and the like, having the above sequence features. The present invention provides a recombinant DNA molecule encoding mRNA containing the 5′ UTR (a) or (b) defined below, a vector obtained by ligating the recombinant DNA molecule to a site immediately downstream of the transcription initiation point of a promoter, and a transformant comprising the vector:
(a) 5′ UTR in which a sequence of bases 1 to 7 and a sequence of bases 12 to 32 from the 5′ end are, respectively, a sequence of bases 1 to 7 and a sequence of bases 12 to 32 of SEQ ID NO: 4, 6, 20, 36, or 60; and
(b) 5′ UTR in which one or more bases in the base sequence of the 5′ UTR of (a) are replaced, and which escapes translational repression induced by at least one environmental stress selected from the group consisting of heat stress and salt stress.

12 Claims, 31 Drawing Sheets

(56) References Cited

U.S. PATENT DOCUMENTS

2012/0185969 A1* 7/2012 DeBrecht et al. ............. 800/298
2014/0315248 A1* 10/2014 Kato et al. .................... 435/69.1

OTHER PUBLICATIONS

Sugio et al. The 5'-untranslated region of the Oryza sativea alcohol dehydrogenase gene functions as a translational enhancer in monocotyledonous plant cells. Journal of Bioscience and Bioengineering. 2008. 105(3): 300-302.*
GenBank Accession No. X77943. A. thaliana (Columbia) Adh gene. Published Nov. 14, 2006. pp. 1-3.*
International Search Report issued Oct. 9, 2012 in International (PCT) Application No. PCT/JP2012/071815.
International Search Report issued Sep. 14, 2010 in International (PCT) Application No. PCT/JP2010/064006.
"Arabidopsis thaliana At1g06760/F4H5 14 mRNA, complete cds", AY050452 [online], National Center for Biotechnology Information, <http://www.ncbi.nlm.nih.gov/nuccore/AY050452>, Aug. 20, 2001.
"AU237926 RAFL16 Arabidopsis thaliana cDNA clone RAFL16-67-M01 5-, mRNA sequence", AU237926 [online], National Center for Biotechnology Information, <http://www.ncbi.nlm.nih.gov/nucest/AU237926>, Aug. 7, 2006.
"SAIL 302 G07.v1 SAIL Collection Arabidopsis thaliana genomic clone SAIL 302 G07.v1, genomic survey sequence", CL479140 [online], National Center for Biotechnology Information, <http://www.ncbi.nlm.nih.gov/nucgss/CL479140>, Apr. 1, 2004.
"Arabidopsis thaliana clone 38378 mRNA, complete sequence", AY087780 [online], National Center for Biotechnology Information, <http://www.ncbi.nlm.nih.gov/nuccore/AY087780>, Jan. 27, 2006.
Kato et al., "5' UTR is an Important Factor to Determine Translational State Under Stressful Environment", Japanese Society for Plant Cell and Molecular Biology Taikai Symposium Koen Yoshishu, vol. 28, 2010, p. 137, with English translation.
Matsuura et al., "Genome-Wide Analyses of Early Translational Responses to Elevated Temperature and High Salinity in *Arabidopsis thaliana*", Plant and Cell Physiology, vol. 51, No. 3, 2010, pp. 448-462.
International Preliminary Report on Patentability issued Mar. 2, 2014 in corresponding International Application No. PCT/JP2012/071815 with English translation.
27th Japanese Society for Plant Cell and Molecular Biology (Fujisawa) Taikai Symposium Yoshishu, Jul. 29, 2009, p. 149, 2Ea-04 (together with English translation).
Abstract of the Annual Meeting of the Society for Biotechnology, Japan, Sep. 25, 2005, p. 124, 1D14-2 (together with English translation).
Abstracts of the Annual Meeting of the Society for Biotechnology, Japan, Sep. 25, 2005, p. 124, 1D14-3 (together with English translation).
51st The Japanese Society of Plant Physiologists Nenkai Koen Yoshishu, Mar. 12, 2010, p. 330, P2D016 (908) (together with English translation).
Gebauer F et al., "Molecular Mechanisms of Translational Control," Nature Reviews Molecular Cell Biology, vol. 5, Oct. 2004, pp. 827-835.
Kawaguchi R et al., "Differential mRNA translation contributes to gene regulation under non-stress and dehydration stress conditions in *Arabidopsis thaliana*", The Plant Journal, 2004, vol. 38, pp. 823-839.
Branco-Price C et al., "Genome-wide Analysis of Transcript Abundance and Translation in Arabidopsis Seedlings Subjected to Oxygen Deprivation", Annals of Botany, vol. 96, pp. 647-660, 2005.
Kawaguchi R et al., "mRNA sequence features that contribute to translational regulation in Arabidopsis", Nucleic Acids Research, vol. 33, No. 3, pp. 955-965, 2005.
Branco-Price C et al., "Selective mRNA translation coordinates energetic and metabolic adjustments to cellular oxygen deprivation and reoxygenation in *Arabidopsis thaliana*", The Plant Journal, vol. 56, pp. 743-755, 2008.
Matsuura H et al., "Preferential Translation Mediated by *Hsp81-3* 5'-UTR during Heat Shock Involves Ribosome Entry at the 5'-end Rather than an Internal Site in *Arabidopsis* Suspension Cells", Journal of Bioscience and Bioengineering, vol. 105, No. 1, pp. 39-47, 2008.
Dinkova T et al., "Cap-independent translation of maize *Hsp101*", The Plant Journal, vol. 41, pp. 722-731, 2005.
Mardanova E et al., "The 5' untranslated region of the maize alcohol dehydrogenase gene contains an internal ribosome entry site", Gene, vol. 420, pp. 11-16, 2008.

* cited by examiner

Fig. 1

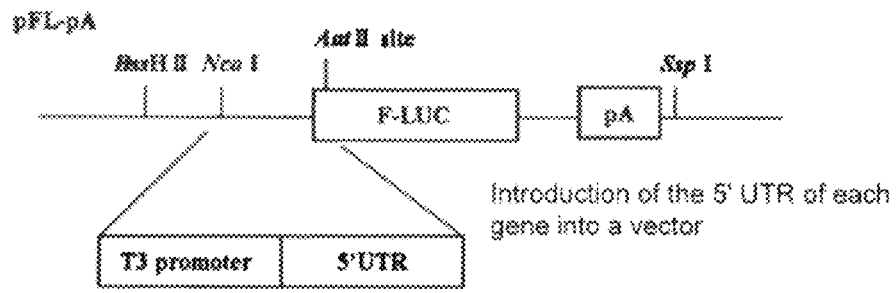

Fig. 2

|   | $s_1$ | $s_2$ | $\cdots$ | $s_k$ | $\cdots$ | $s_{k+L-1}$ | $\cdots$ | $s_M$ | $y$ |
|---|---|---|---|---|---|---|---|---|---|
| 1 | $s_{11}$ | $s_{12}$ | $\cdots$ | $s_{1k}$ | $\cdots$ | $s_{1(k+L-1)}$ | $\cdots$ | $s_{1M}$ | $y_1$ |
| 2 | $s_{21}$ | $s_{22}$ | $\cdots$ | $s_{2k}$ | $\cdots$ | $s_{2(k+L-1)}$ | $\cdots$ | $s_{2M}$ | $y_2$ |
| $\vdots$ | $\cdots$ | $\cdots$ | $\cdots$ | $\cdots$ | $\cdots$ | $\cdots$ | $\cdots$ | $\cdots$ | $\cdots$ |
| $i$ | $s_{i1}$ | $s_{i2}$ | $\cdots$ | $s_{ik}$ | $\cdots$ | $s_{i(k+L-1)}$ | $\cdots$ | $s_{iM}$ | $y_i$ |
| $\vdots$ | $\cdots$ | $\cdots$ | $\cdots$ | $\cdots$ | $\cdots$ | $\cdots$ | $\cdots$ | $\cdots$ | $\cdots$ |
| $N$ | $s_{N1}$ | $s_{N2}$ | $\cdots$ | $s_{Nk}$ | $\cdots$ | $s_{N(k+L-1)}$ | $\cdots$ | $s_{NM}$ | $y_N$ |

Fig. 3

|   | $f^{(k,k+L-1)}(R_1(t))$ | $f^{(k,k+L-1)}(R_2(t))$ | $\cdots$ | $f^{(k,k+L-1)}(R_v(t))$ | $\cdots$ | $f^{(k,k+L-1)}(R_Y(t))$ |
|---|---|---|---|---|---|---|
| 1 | $f_1^{(k,k+L-1)}(R_1(t))$ | $f_1^{(k,k+L-1)}(R_2(t))$ | $\cdots$ | $f_1^{(k,k+L-1)}(R_v(t))$ | $\cdots$ | $f_1^{(k,k+L-1)}(R_Y(t))$ |
| 2 | $f_2^{(k,k+L-1)}(R_1(t))$ | $f_2^{(k,k+L-1)}(R_2(t))$ | $\cdots$ | $f_2^{(k,k+L-1)}(R_v(t))$ | $\cdots$ | $f_2^{(k,k+L-1)}(R_Y(t))$ |
| $\vdots$ | $\cdots$ | $\cdots$ | $\cdots$ | $\cdots$ | $\cdots$ | $\cdots$ |
| $i$ | $f_i^{(k,k+L-1)}(R_1(t))$ | $f_i^{(k,k+L-1)}(R_2(t))$ | $\cdots$ | $f_i^{(k,k+L-1)}(R_v(t))$ | $\cdots$ | $f_i^{(k,k+L-1)}(R_Y(t))$ |
| $\vdots$ | $\cdots$ | $\cdots$ | $\cdots$ | $\cdots$ | $\cdots$ | $\cdots$ |
| $N$ | $f_N^{(k,k+L-1)}(R_1(t))$ | $f_N^{(k,k+L-1)}(R_2(t))$ | $\cdots$ | $f_N^{(k,k+L-1)}(R_v(t))$ | $\cdots$ | $f_N^{(k,k+L-1)}(R_Y(t))$ |

A. The relative activity level and the sequence information of the 39 genes tested in Fig. 9 are extracted.

| Sample | Relative activity level | Sequence | | | |
|---|---|---|---|---|---|
| A 5'UTR | 1.15 | a u g c a u | a u a a a a u a g a | u c u g u c g g u c c u g u | SEQ ID NO:13 |
| B 5'UTR | 0.20 | g c g a u u | g g a g a c c a u a | a c u g c u g | SEQ ID NO:14 |
| n 5'UTR | 1.80 | a a a u c a | u u a u u a a a g a | a a u a c c c c | SEQ ID NO:15 |

B. A sequence of length L from base position k is taken out.

k=7, L=10

| | $s_7$ | $s_8$ | $s_9$ | $s_{10}$ | $s_{11}$ | $s_{16}$ | y |
|---|---|---|---|---|---|---|---|
| $Seq_1$ | a | u | a | a | a | ⋯ a | 1.15 |
| $Seq_2$ | g | g | a | g | a | a | 0.20 |
| ⋮ | | | | | | | |
| $Seq_N$ | u | u | a | u | u | ⋯ a | 1.80 |

C. Frequencies of sequences each consisting of t number of bases contained in the sequence taken out are counted.

t = 3

| | y | f(aua) | f(uaa) | f(aaa) | f(aau) | f(uag) | f(aga) | ⋯ | $f(R_p(t))$ |
|---|---|---|---|---|---|---|---|---|---|
| $Seq_1$ | 1.15 | 2 | 1 | 2 | 1 | 1 | 1 | ⋯ | $f_1(R_p(t))$ |
| $Seq_2$ | 0.20 | 1 | 0 | 0 | 0 | 0 | 1 | ⋯ | $f_2(R_p(t))$ |
| ⋮ | ⋮ | ⋮ | ⋮ | ⋮ | ⋮ | ⋮ | ⋮ | ⋯ | ⋮ |
| $Seq_N$ | 1.80 | 0 | 1 | 1 | 0 | 0 | 1 | ⋯ | $f_N(R_p(t))$ |

D. The regression coefficient for each sequence consisting of t number of bases is determined by PLS.

$$y = a_{(aua)}f(aua) + a_{(uaa)}f(uaa) + a_{(aaa)}f(aaa) \cdots + a_{(R_p(t))}f(R_p(t)) + a_{0(t)}$$

| | $a_{(aua)}$ | $a_{(uaa)}$ | $a_{(aaa)}$ | $a_{(aau)}$ | ⋯ | $a_{(R_p(t))}$ |
|---|---|---|---|---|---|---|
| PLS coefficient | 0.251 | 1.234 | 1.805 | 0.777 | ⋯ | 0.101 |

Fig. 19

A. PLS regression coefficients are placed.

| k | 7 | 8 | 9 | 10 | 11 | 12 | 13 | 14 | 15 | 16 |
|---|---|---|---|----|----|----|----|----|----|----|
| $Seq_1$ | a | u | a | a | a | ... | ... | a | g | a |
| | 0.251 | 0.251 | 0.251 | | | | | | | |
| | | 1.234 | 1.234 | 1.234 | | | | | | |
| | | | 1.805 | 1.805 | 1.805 | | | | | |
| | | | | | | ... | ... | ... | ... | |
| | | | | | | | | $a_{(\alpha g a)}$ | $a_{(\alpha g a)}$ | $a_{(\alpha g a)}$ |
| ⋮ | | | | | | | | | | |
| $Seq_N$ | u | u | a | u | u | ... | ... | a | g | a |
| | $a_{(uua)}$ | $a_{(uua)}$ | $a_{(uua)}$ | | | | | | | |
| | | $a_{(uau)}$ | $a_{(uau)}$ | $a_{(uau)}$ | | | | | | |
| | | | $a_{(auu)}$ | $a_{(auu)}$ | $a_{(auu)}$ | | | | | |
| | | | | | | ... | ... | ... | ... | |
| | | | | | | | | $a_{(\alpha g a)}$ | $a_{(\alpha g a)}$ | $a_{(\alpha g a)}$ |

B. The means of the numerical values placed in the matrix for bases a, u, g, and, c at each base position are determined, and a t-test is performed.

$$t(base)_{k,j} = \frac{|av(base)_{k,j}|}{\sqrt{\frac{V(base)_{k,j}}{n(s_{k,j} = base)}}}$$

| k | | 7 | 8 | 9 | 10 | 11 | 12 | 13 | 14 | 15 | 16 |
|---|---|---|---|---|----|----|----|----|----|----|----|
| a | $av$ | $av(A)_7$ | $av(A)_8$ | ... | ... | ... | ... | ... | ... | ... | $av(A)_{16}$ |
|   | $V$ | $V(A)_7$ | $V(A)_8$ | ... | ... | ... | ... | ... | ... | ... | $V(A)_{16}$ |
| u | $av$ | $av(U)_7$ | $av(U)_8$ | ... | ... | ... | ... | ... | ... | ... | $av(U)_{16}$ |
|   | $V$ | $V(U)_7$ | $V(U)_8$ | ... | ... | ... | ... | ... | ... | ... | $V(U)_{16}$ |
| g | $av$ | $av(G)_7$ | $av(G)_8$ | ... | ... | ... | ... | ... | ... | ... | $av(G)_{16}$ |
|   | $V$ | $V(G)_7$ | $V(G)_8$ | ... | ... | ... | ... | ... | ... | ... | $V(G)_{16}$ |
| c | $av$ | $av(C)_7$ | $av(C)_8$ | ... | ... | ... | ... | ... | ... | ... | $av(C)_{16}$ |
|   | $V$ | $V(C)_7$ | $V(C)_8$ | ... | ... | ... | ... | ... | ... | ... | $V(C)_{16}$ |

At1g77120+   m⁷-GGCACGGGGACUCUAGA [At1g77120] [F-LUC] (AAA)ₙ₌₄₉   (SEQ ID NO: 90)

At1g77120    m⁷-GG [At1g77120] [F-LUC] (AAA)ₙ₌₄₉

Fig. 32

RECOMBINANT DNA MOLECULE ENCODING 5' UTR CAPABLE OF PREVENTING INHIBITION OF TRANSLATION UNDER ENVIRONMENTAL STRESSES

This application is a U.S. national stage of International Application No. PCT/W2010/064006 filed Aug. 19, 2010.

TECHNICAL FIELD

The present invention mainly relates to recombinant gene encoding the 5' untranslated region (hereinafter also referred to as 5' UTR) that contributes to the escape from translational repression under environmental stresses; an expression vector comprising the recombinant gene; and a transformant comprising the expression vector.

BACKGROUND ART

As is the case with other eukaryotes such as animals and yeast, the rate of protein synthesis in plants is also usually controlled by the initial translation reaction (NPL 1).

The initiation of translation is one of the important control stages for plants to control gene expression in quick response to changes in the external environment. For example, translation of the majority of mRNAs to proteins is repressed under various stresses such as temperature, osmotic pressure, and anaerobic conditions (low-oxygen). However, the translation of mRNA is not entirely repressed. The translation of some mRNAs, i.e., protein synthesis, is maintained. Such knowledge suggests the presence of a gene expression control mechanism, which selectively and quickly synthesizes necessary proteins while repressing the majority of protein synthesis, at the translational level in response to external environmental stresses.

In recent years, attempts have been made to exhaustively analyze changes in the translational state of each mRNA induced by various environmental stresses. These attempts are to exhaustively understand the translational state of each gene by subjecting mRNA fractionated according to the degree of ribosomal binding to microarray analysis (NPL 2 to 5). Because of these attempts, the presence of numerous mRNA species whose translation is not repressed even under stress has become evident, and it has become clear that changes in the translational level in response to stress are not digitally determined to be repressed or not repressed depending on the mRNA species, but such changes occur in a continuous manner as a whole.

At the same time, a relationship between changes in the translational state caused by stress and the 5' untranslated region (5' UTR) has been suggested. For example, it has been reported from an analysis in which the 5' UTR of corn Hsp 101 or ADH or *Arabidopsis thaliana* HSP 81-3 was linked to a reporter gene, that the 5' UTR is important for the escape from stress-induced translational repression (NPL 6 to 8). However, a detailed mechanism thereof has not been clarified.

Based on the above-described relationship, which became clear by polysome/microarray analysis, between the translational state of each mRNA species and the features of the 5' UTR of *Arabidopsis thaliana* plants under dehydration stress, Kawaguchi et al. made an attempt to search for an intrinsic factor of the 5' UTR, which regulates translational control under stress, and reported that there is a correlation between the translational state under dehydration stress and the features of the 5' UTR such as the length of the 5' UTR and low GC content in the 5' UTR. However, important sequence features have not been found even in this report, and Kawaguchi et al. themselves state that the length of 5' UTR and the rate of GC content are not considered to be determining factors of the translational state under stress (NPL 4).

CITATION LIST

[NPL]

[NPL 1] Gebauer, F. and Hentze, M. W., 2004, Molecular mechanisms of translational control, Nat. Rev. Mol. Cell Biol., 5: 827-835

[NPL 2] Kawaguchi, R., Girke, T., Bray, E. A., and Bailey-Serres. J., 2004, Differential mRNA translation contributes to gene regulation under non-stress and dehydration stress conditions in *Arabidopsis thaliana*, The Plant Journal, 38: 823-839.

[NPL 3] Branco-Price, C., Kawaguchi, R., Ferreira, R. B., and Bailey-Serres, J., 2005, Genome-wide Analysis of Transcript Abundance and Translation in *Arabidopsis* Seedlings Subjected to Oxygen Deprivation, Annals of Botany, 96: 647-660

[NPL 4] Kawaguchi, R., and Bailey-Serres, J., 2005, mRNA sequence features that contribute to translational regulation in *Arabidopsis*, Nucleic Acids Res., 3: 955-965

[NPL 5] Branco-Price, C., Kaiser, K. A., Jang, C. J. H., Larive, C. K., and Bailey-Serres, J., 2008, Selective mRNA translation coordinates energetic and metabolic adjustments to cellular oxygen deprivation and reoxygenation in *Arabidopsis thaliana*. The Plant Journal, 56: 743-755

[NPL 6] Matsuura, H., Shinmyo, A., and Kato, K. 2008. Preferential translation mediated by Hsp 81-3 5'-UTR during heat shock involves ribosome entry at the 5'-end rather than an internal site in *Arabidopsis* suspension cells. J. Biosci. Bioeng., 105: 39-47

[NPL 7] Dinkova, T. D., Zepeda, H., Martinez-Salas, E., Martinez, L. M., Nieto-Sotelo, J., and de Jimenez, E. S., 2005, Cap-independent translation of maize Hsp 101. The Plant Journal, 41: 722-731

[NPL 8] Mardanova, E. S., Zamchuk. L. A., Skulachev, M. V., and Ravin, N, V., 2008, The 5' untranslated region of the maize alcohol dehydrogenase gene contains an internal ribosome entry site. Gene, 420: 11-16

SUMMARY OF INVENTION

Technical Problem

As described above, sequence features of the 5' UTR that regulates translational control in plants under environmental stresses have not been clarified.

A main object of the present invention is to find sequence features of the 5' UTR, which are involved in changes in the translational state of plants under environmental stresses, and to provide a recombinant gene, an expression vector, and a transformant, which have the above sequence features.

Solution to Problem

The present inventors conducted extensive research to solve the above problem. As a result, the present inventors obtained sequence information of the 5' UTR and actual measurement data relating to changes in the translational state under environmental stresses, performed in silico analysis based on the above data, and conducted examinations based on the actual data. Thereby, the present inventors succeeded in identifying an important region and sequence of the 5' UTR that regulates translational control. The present invention was accomplished by further extensive examinations.

Specifically, the present invention encompasses, for example, Item 1 to 13 described below, including a recombinant DNA molecule, an artificial mRNA molecule, a vector, a transformant, a method for producing a protein encoded by the recombinant gene by the use of the transformant, a method for producing a gene, and a method for escaping translational repression.

Item 1.

A recombinant DNA molecule encoding mRNA containing the 5' UTR as defined in (a) or (b) below:

(a)

(i) 5' UTR in which a sequence of bases 1 to 7 from the 5' end is a sequence of bases 1 to 7 of SEQ ID NO: 4, and a sequence of bases 12 to 32 from the 5' end is a sequence of bases 12 to 32 of SEQ ID NO: 4;

(ii) 5' UTR in which a sequence of bases 1 to 7 from the 5' end is a sequence of bases 1 to 7 of SEQ ID NO: 6, and a sequence of bases 12 to 32 from the 5' end is a sequence of bases 12 to 32 of SEQ ID NO: 6;

(iii) 5' UTR in which a sequence of bases 1 to 7 from the 5' end is a sequence of bases 1 to 7 of SEQ ID NO: 20, and a sequence of bases 12 to 32 from the 5' end is a sequence of bases 12 to 32 of SEQ ID NO: 20;

(iv) 5' UTR in which a sequence of bases 1 to 7 from the 5' end is a sequence of bases 1 to 7 of SEQ ID NO: 36, and a sequence of bases 12 to 32 from the 5' end is a sequence of bases 12 to 32 of SEQ ID NO: 36; or (v) 5' UTR in which a sequence of bases 1 to 7 from the 5' end is a sequence of bases 1 to 7 of SEQ ID NO: 60, and a sequence of bases 12 to 32 from the 5' end is a sequence of bases 12 to 32 of SEQ ID NO: 60; or (b) 5' UTR in which one or more bases in the base sequence of the 5' UTR of (a) are replaced, and which escapes translational repression induced by at least one environmental stress selected from the group consisting of heat stress and salt stress.

Item 2.

The recombinant DNA molecule as defined in Item 1, wherein the 5' UTR of (a) is 5' UTR having a base sequence of SEQ ID NO: 4, 6, 20, 36, or 60 at the 5' end.

Item 3.

A vector obtained by ligating the recombinant DNA molecule as defined in Item 1 or 2 to a site immediately downstream of the transcription initiation point of a promoter.

Item 4.

A transformant transformed by the vector as defined in Item 3.

Item 5.

The transformant as defined in Item 4, wherein the transformant is a transgenic plant.

Item 6.

A method for producing a protein encoded by the recombinant DNA molecule, comprising growing the transformant as defined in Item 4 or 5 under at least one environmental stress selected from the group consisting of heat stress and salt stress.

Item 7.

A method for producing a plant capable of escaping translational repression induced by at least one environmental stress selected from the group consisting of heat stress and salt stress, the method comprising introducing the vector as defined in Item 3 into a plant.

Item 8.

A method for producing a gene that escapes translational repression induced by at least one environmental stress selected from the group consisting of heat stress and salt stress, the method comprising modifying a base sequence so as to encode mRNA containing 5' UTR defined in (a) or (b) below:

(a)

(i) 5' UTR in which a sequence of bases 1 to 7 from the 5' end is a sequence of bases 1 to 7 of SEQ ID NO: 4, and a sequence of bases 12 to 32 from the 5' end is a sequence of bases 12 to 32 of SEQ ID NO: 4;

(ii) 5' UTR in which a sequence of bases 1 to 7 from the 5' end is a sequence of bases 1 to 7 of SEQ ID NO: 6, and a sequence of bases 12 to 32 from the 5' end is a sequence of bases 12 to 32 of SEQ ID NO: 6;

(iii) 5' UTR in which a sequence of bases 1 to 7 from the 5' end is a sequence of bases 1 to 7 of SEQ ID NO: 20, and a sequence of bases 12 to 32 from the 5' end is a sequence of bases 12 to 32 of SEQ ID NO: 20;

(iv) 5' UTR in which a sequence of bases 1 to 7 from the 5' end is a sequence of bases 1 to 7 of SEQ ID NO: 36, and a sequence of bases 12 to 32 from the 5' end is a sequence of bases 12 to 32 of SEQ ID NO: 36; or (v) 5' UTR in which a sequence of bases 1 to 7 from the 5' end is a sequence of bases 1 to 7 of SEQ ID NO: 60, and a sequence of bases 12 to 32 from the 5' end is a sequence of bases 12 to 32 of SEQ ID NO: 60; or (b) 5' UTR in which one or more bases in the base sequence of the 5' UTR of (a) are replaced, and which escapes translational repression induced by at least one environmental stress selected from the group consisting of heat stress and salt stress.

Item 9.

The method for producing a gene as defined in Item 8, wherein the 5' UTR of (a) is 5' UTR having a base sequence of SEQ ID NO: 4, 6, 20, 36, or 60 at the 5' end.

Item 10.

A method for escaping translational repression of a protein encoded by a gene, the translational repression being induced by at least one environmental stress selected from the group consisting of heat stress and salt stress, the method comprising modifying a base sequence of the gene so as to encode mRNA containing 5' UTR defined in (a) or (b) below:

(a)

(i) 5' UTR in which a sequence of bases 1 to 7 from the 5' end is a sequence of bases 1 to 7 of SEQ ID NO: 4, and a sequence of bases 12 to 32 from the 5' end is a sequence of bases 12 to 32 of SEQ ID NO: 4;

(ii) 5' UTR in which a sequence of bases 1 to 7 from the 5' end is a sequence of bases 1 to 7 of SEQ ID NO: 6, and a sequence of bases 12 to 32 from the 5' end is a sequence of bases 12 to 32 of SEQ ID NO: 6;

(iii) 5' UTR in which a sequence of bases 1 to 7 from the 5' end is a sequence of bases 1 to 7 of SEQ ID NO: 20, and a sequence of bases 12 to 32 from the 5' end is a sequence of bases 12 to 32 of SEQ ID NO: 20;

(iv) 5' UTR in which a sequence of bases 1 to 7 from the 5' end is a sequence of bases 1 to 7 of SEQ ID NO: 36, and a sequence of bases 12 to 32 from the 5' end is a sequence of bases 12 to 32 of SEQ ID NO: 36; or (v) 5' UTR in which a sequence of bases 1 to 7 from the 5' end is a sequence of bases 1 to 7 of SEQ ID NO: 60, and a sequence of bases 12 to 32 from the 5' end is a sequence of bases 12 to 32 of SEQ ID NO: 60; or (b) 5' UTR in which one or more bases in the base sequence of the 5' UTR of (a) are replaced, and which escapes translational repression induced by at least one environmental stress selected from the group consisting of heat stress and salt stress.

Item 11.
The method for escaping translational repression of a protein as defined in Item 10, wherein the 5' UTR of (a) is 5' UTR having a base sequence of SEQ ID NO: 4, 6, 20, 36, or 60 at the 5' end.

Item 12.
An artificial mRNA molecule containing 5' UTR defined in (a) or (b) below:
(a)
(i) 5' UTR in which a sequence of bases 1 to 7 from the 5' end is a sequence of bases 1 to 7 of SEQ ID NO: 4, and a sequence of bases 12 to 32 from the 5' end is a sequence of bases 12 to 32 of SEQ ID NO: 4;
(ii) 5' UTR in which a sequence of bases 1 to 7 from the 5' end is a sequence of bases 1 to 7 of SEQ ID NO: 6, and a sequence of bases 12 to 32 from the 5' end is a sequence of bases 12 to 32 of SEQ ID NO: 6;
(iii) 5' UTR in which a sequence of bases 1 to 7 from the 5' end is a sequence of bases 1 to 7 of SEQ ID NO: 20, and a sequence of bases 12 to 32 from the 5' end is a sequence of bases 12 to 32 of SEQ ID NO: 20;
(iv) 5' UTR in which a sequence of bases 1 to 7 from the 5' end is a sequence of bases 1 to 7 of SEQ ID NO: 36, and a sequence of bases 12 to 32 from the 5' end is a sequence of bases 12 to 32 of SEQ ID NO: 36; or
(v) 5' UTR in which a sequence of bases 1 to 7 from the 5' end is a sequence of bases 1 to 7 of SEQ ID NO: 60, and a sequence of bases 12 to 32 from the 5' end is a sequence of bases 12 to 32 of SEQ ID NO: 60; or
(b) 5' UTR in which one or more bases in the base sequence of the 5' UTR of (a) are replaced, and which escapes translational repression induced by at least one environmental stress selected from the group consisting of heat stress and salt stress.

Item 13.
The artificial mRNA molecule as defined in Item 8, wherein the 5' UTR of (a) is 5' UTR having a base sequence of SEQ ID NO: 4, 6, 20, 36, or 60 at the 5' end.

Advantageous Effects of Invention

The present invention provides a recombinant gene capable of escaping translational repression under environmental stresses. The present invention also provides a vector obtained by ligating the recombinant gene to a site immediately downstream of the transcription initiation point of a promoter, and also provides a transformant comprising the vector. These techniques allow expression of a gene with high efficiency without being subjected to translational repression even under environmental stresses. Further, these techniques also contribute particularly to the production of plants that are resistant to environmental stresses and to the establishment of production technology of stable, useful substances in plants.

BRIEF DESCRIPTION OF DRAWINGS

FIG. 1 shows a schematic diagram of a constructed plasmid. A DNA fragment in which the 5' UTR sequence to be tested is ligated to the downstream of a T3 promoter is inserted into a plasmid to synthesize f-luc mRNA using the NcoI and AatII sites.

FIG. 2 shows an example of arrangement of the sequence information and the relative activity level. A sequence of length L from position k taken out from sample i is expressed as $Seq_i = s_{ik} s_{ik+1} \ldots s_{ik+L-1}$. Herein, the positions in the base sequence of sample i are expressed as $s_1, s_2, \ldots, s_k, \ldots, s_M$ in the direction from the 5' end to 3'. Further, the relative activity of sample i is expressed as $y_i$.

FIG. 3 shows an example of a matrix of the frequencies of sequences each consisting of t number of consecutive bases $(R_1(t), R_2(t), \ldots, R_v(t), R_V(t))$ in a sequence of length L from k to k+L−1 in N number of samples. Sequences each consisting of t number of bases, which appear at least once in the sequence of length L from base positions k to k+L−1 in N number of samples, are expressed as $R_1(t), R_2(t), \ldots, R_v(t), R_V(t)$. Further, the appearance frequencies of these sequences are expressed as $f_i^{(k, k+L-1)}(R_1(t)), \ldots, f_i^{(k, k+L-1)}(R_v(t)), \ldots, f_i^{(k, k+L-1)}(R_V(t))$. The frequency of the $v^{th}$ sequence is expressed as variable $f_i^{(k, k+L-1)}(R_v(t))$.

FIG. 4 shows an example of a matrix of the regression coefficients for base position j+k. FIG. 4 also shows the averages and the unbiased estimates of the variance of the regression coefficients corresponding to four bases. Whether the distribution of the regression coefficients individually corresponding to the 4 bases (A, U, G, and C) is considered to be statistically significantly positive or negative is tested based on the averages and the unbiased estimates of the variance of the regression coefficients with the 4 bases (A, U, G, and C) at the position j+k and unbiased estimates of the variance, thereby obtaining information regarding what base at what position in the sequence of length L from base positions k to k+L−1 contributes to the relative activity level positively or negatively.

FIG. 10 shows a conceptual diagram of the construction of a regression model and the calculation of the regression coefficients based on PLS method. FIG. 10A: the relative activity level and the sequence information of the 39 genes tested in FIG. 9 are extracted. FIG. 10B: a sequence of length L from base position k is taken out. FIG. 10C: frequencies of sequence each consisting of t number of bases contained in the sequence taken out are counted. FIG. 10D: the regression coefficient for each sequence consisting of t number of bases is determined by PLS.

FIG. 19 shows a conceptual diagram for the calculation of the degree of contribution to the relative activity level of each base at each base position, using PLS regression coefficients. FIG. 19A:PLA regression coefficients are placed. FIG. 19B: the means of the numerical values placed in the matrix for bases a, u, g, and c at each base position are determined, and a t-test is performed.

FIG. 20A: the base position 1 to 9 in the 5' UTR. FIG. 20B: the base position 14 to 34 in the 5' UTR.

FIG. 28A shows the results obtained by recording the absorbance profile at 254 nm after fractionating cell extracts prepared from normal cells (22° C.) and heat stress-treated cells (37° C./10 min.) by sucrose density gradient centrifugation (15-60%). In FIG. 28B, cell extracts derived from normal cells and heat stress-treated cells (37° C./10 min.) were collected by dividing the fractionated sucrose density gradient into 15 fractions, and RNA was extracted from each fraction. The position of each fraction corresponds to the absorbance profile described in FIG. 28A. The same amount of each RNA extract solution was subjected to denaturing gel electrophoresis, followed by EtBr staining. The figure shows the positions of 28S rRNA and 18S rRNA. In FIG. 28C, the same amount of each RNA extract was subjected to RT-PCR assay, and the mRNA present in each fraction was detected in each of the following: GUS containing the 5' UTR of At3g47610; At1g77120; At4g14560; and Actin2. The figure shows the results.

FIG. 29A shows the results obtained by recording the absorbance profile at 254 nm after fractionating the cell extracts prepared from normal cells (22° C.) and heat stress-treated cells (37° C./10 min.) by sucrose density gradient centrifugation (15-60%). In FIG. 29B, the cell extracts derived from normal cells and heat stress-treated cells (37° C./10 min.) were collected by dividing the fractionated sucrose density gradient into 15 fractions, and RNA was extracted from each fraction. The position of each fraction corresponds to the absorbance profile described in FIG. 29A. The same amount of each RNA extract solution was subjected to denaturing gel electrophoresis, followed by EtBr staining. The figure shows the positions of 28S rRNA and 18S rRNA. In FIG. 29C, the same amount of each RNA extract was subjected to RT-PCR assay, and the mRNA present in each fraction was detected in each of the following: GUS containing the 5' UTR of At5g39740; At1g77120; At3g47610; and Actin2. The figure shows the results.

FIG. 30A shows the results obtained by recording the absorbance profile at 254 nm after fractionating the cell extracts prepared from normal cells (22° C.) and heat stress-treated cells (37° C./10 min.) by sucrose density gradient centrifugation (15-60%). For FIG. 30B, the cell extracts derived from normal cells and heat stress-treated cells (37° C./10 min.) were collected by dividing the fractionated sucrose density gradient into 15 fractions, and RNA was extracted from each fraction. The position of each fraction corresponds to the absorbance profile described in FIG. 30A. The same amount of each RNA extract solution was subjected to denaturing gel electrophoresis, followed by EtBr staining. The figure shows the positions of 28S rRNA and 18S rRNA. For FIG. 30C, the same amount of each RNA extract was subjected to RT-PCR assay, and the mRNA present in each fraction was detected in each of the following: GUS containing the 5' UTR of At4g14560; At4g14560; At3g47610; and Actin2. The figure shows the results.

FIG. 31A shows the results obtained by recording the absorbance profile at 254 nm after fractionating the cell extracts prepared from normal cells (22° C.) and heat stress-treated cells (37° C./10 min.) by sucrose density gradient centrifugation (15-60%). For FIG. 31B, the cell extracts derived from normal cells and heat stress-treated cells (37° C./10 min.) were collected by dividing the fractionated sucrose density gradient into 15 fractions, and RNA was extracted from each fraction. The position of each fraction corresponds to the absorbance profile described in FIG. 31A. The same amount of each RNA extract solution was subjected to denaturing gel electrophoresis, followed by EtBr staining. The figure shows the positions of 28S rRNA and 18S rRNA. For FIG. 31C, the same amount of each RNA extract was subjected to RT-PCR assay, and the mRNA present in each fraction was detected in each of the following: GUS containing the 5' UTR of At1g77120; At1g77120; At3g47610; and Actin2. The figure shows the results.

FIG. 32 shows the results from polysome/RT-PCR assay of cells transformed with At4g14560+ and the results obtained using two independently isolated lines of transformed cells. FIG. 32A shows the results obtained by recording the absorbance profile at 254 nm after fractionating the cell extracts prepared from normal cells (22° C.) and heat stress-treated cells (37° C./10 min.) by sucrose density gradient centrifugation (15-60%). For FIG. 32B, the cell extracts derived from normal cells and heat stress-treated cells (37° C./10 min.) were collected by dividing the fractionated sucrose density gradient into 15 fractions, and RNA was extracted from each fraction. The position of each fraction corresponds to the absorbance profile described in FIG. 32A. The same amount of each RNA extract solution was subjected to denaturing gel electrophoresis, followed by EtBr staining. The figure shows the positions of 28S rRNA and 18S rRNA. For FIG. 32C, the same amount of each RNA extract was subjected to RT-PCR assay, and the mRNA present in each fraction was detected in each of the following: GUS containing the 5' UTR of At4g14560+; At4g14560; At3g47610; and Actin2. The figure shows the results.

FIG. 33A shows the results obtained by recording the absorbance profile at 254 nm after fractionating the cell extracts prepared from normal cells (22° C.) and heat stress-treated cells (37° C./10 min.) by sucrose density gradient centrifugation (15-60%). For FIG. 33B, the cell extracts derived from normal cells and heat stress-treated cells (37° C./10 min.) were collected by dividing the fractionated sucrose density gradient into 15 fractions, and RNA was extracted from each fraction. The position of each fraction corresponds to the absorbance profile described in FIG. 33A. The same amount of each RNA extract solution was subjected to denaturing gel electrophoresis, followed by EtBr staining. The figure shows the positions of 28S rRNA and 18S rRNA. For FIG. 33C, the same amount of each RNA extract was subjected to RT-PCR assay, and the mRNA present in each fraction was detected in each of the following: GUS containing the 5' UTR of At1g77120+; At1g77120; At3g47610; and Actin2. The figure shows the results.

FIG. 34A shows the results obtained by recording the absorbance profile at 254 nm after fractionating the cell extracts prepared from normal cells (22° C.) and heat stress-treated cells (37° C./10 min.) by sucrose density gradient centrifugation (15-60%). For FIG. 34B, the cell extracts derived from normal cells and heat stress-treated cells (37° C./10 min.) were collected by dividing the fractionated sucrose density gradient into 15 fractions, and RNA was extracted from each fraction. The position of each fraction corresponds to the absorbance profile described in FIG. 34A. The same amount of each RNA extract solution was subjected to denaturing gel electrophoresis, followed by EtBr staining. The figure shows the positions of 28S rRNA and 18S rRNA. For FIG. 34C, the same amount of each RNA extract was subjected to RT-PCR assay, and the mRNA present in each fraction was detected in each of the following: GUS containing the 5' UTR of At5g39740-S; At1g77120; At3g47610; and Actin2. The figure shows the results.

FIG. 35A shows the results obtained by recording the absorbance profile at 254 nm after fractionating the cell extracts prepared from normal cells (22° C.) and salt stress-treated cells (200 mM NaCl/10 min.) by sucrose density gradient centrifugation (15-60%). For FIG. 35B, the cell extracts derived from normal cells and salt stress-treated cells (200 mM NaCl/10 min.) were collected by dividing the fractionated sucrose density gradient into 15 fractions, and RNA was extracted from each fraction. The position of each fraction corresponds to the absorbance profile described in FIG. 35A. The same amount of each RNA extract solution was subjected to denaturing gel electrophoresis, followed by EtBr staining. The figure shows the positions of 28S rRNA and 18S rRNA. For FIG. 35C, the same amount of each RNA extract was subjected to RT-PCR assay, and the mRNA present in each fraction was detected in each of the following: GUS containing the 5' UTR of At3g47610; At1g77120; At3g47610; and Actin2. The figure shows the results.

FIG. 36A shows the results obtained by recording the absorbance profile at 254 nm after fractionating the cell extracts prepared from normal cells (22° C.) and salt stress-treated cells (200 mM NaCl/10 min.) by sucrose density gradient centrifugation (15-60%). For FIG. 36B, the cell extracts derived from normal cells and salt stress-treated cells (200 mM NaCl/10 min.) were collected by dividing the fractionated sucrose density gradient into 15 fractions, and RNA was extracted from each fraction. The position of each fraction corresponds to the absorbance profile described in FIG. 36A. The same amount of each RNA extract solution was subjected to denaturing gel electrophoresis, followed by EtBr staining. The figure shows the positions of 28S rRNA and 18S rRNA. For FIG. 36C, the same amount of each RNA extract was subjected to RT-PCR assay, and the mRNA present in each fraction was detected in each of the following: GUS containing the 5' UTR of At4g14560; At4g14560; At3g47610; and Actin2. The figure shows the results.

FIG. 37A shows the results obtained by recording the absorbance profile at 254 nm after fractionating the cell extracts prepared from normal cells (22° C.) and salt stress-treated cells (200 mM NaCl/10 min.) by sucrose density gradient centrifugation (15-60%). For FIG. 37B, the cell extracts derived from normal cells and salt stress-treated cells (200 mM NaCl/10 min.) were collected by dividing the fractionated sucrose density gradient into 15 fractions, and RNA was extracted from each fraction. The position of each fraction corresponds to the absorbance profile described in FIG. 37A. The same amount of each RNA extract solution was subjected to denaturing gel electrophoresis, followed by EtBr staining. The figure shows the positions of 28S rRNA and 18S rRNA. For FIG. 37C, the same amount of each RNA extract was subjected to RT-PCR assay, and the mRNA present in each fraction was detected in each of the following: GUS containing the 5' UTR of At1g77120; At1g77120; At3g47610; and Actin2. The figure shows the results.

DESCRIPTION OF EMBODIMENTS

Figure 5:
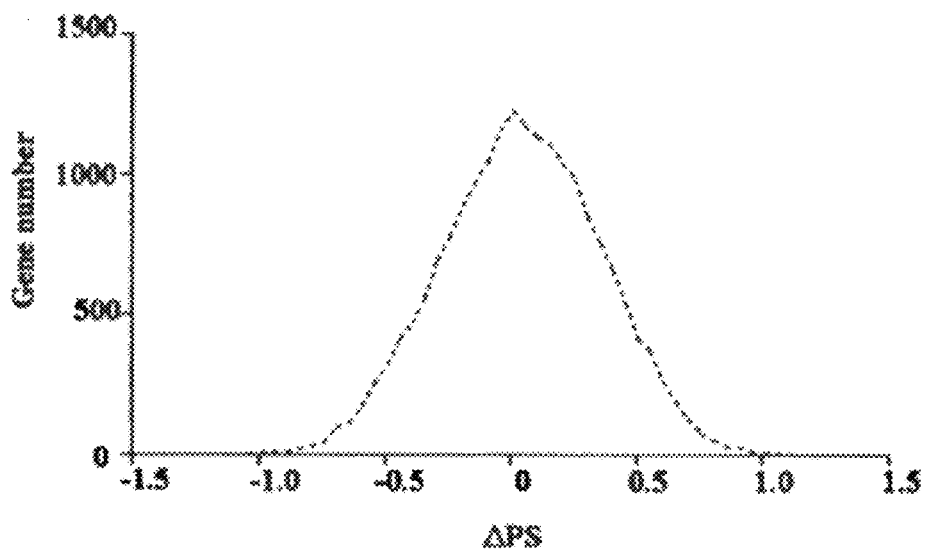
FIG. 5 shows a ΔPS histogram of 19,099 types of mRNA. ΔPS is an index that indicates heat stress-induced changes in the state of polysome formation. A smaller ΔPS value indicates that the translation is more significantly inhibited. The ordinate shows the number of genes.

The present invention is described in further detail below. Abbreviations of amino acids, peptides, base sequences, nucleic acids, and the like indicated in this specification are in accordance with the rules of IUPAC and IUB, "the Guideline for Preparing Specifications, etc., Containing Base Sequences or Amino Acid Sequences" (edited by the Japan Patent Office), and the symbols conventionally used in the relevant field. In particular, DNA stands for deoxyribonucleic acid, RNA stands for ribonucleic acid, and mRNA stands for messenger RNA.

Further, molecular biological manipulations such as genetic manipulation can be suitably performed by known methods. For example, such manipulation can be performed in accordance with a method described in "Molecular Cloning: A Laboratory Manual 3rd Edition" (Cold Spring Harbor Laboratory Press) and the like, unless otherwise specified.

Recombinant Gene (Recombinant DNA Molecule)

In the present invention, a gene is actually a DNA molecule encoding mRNA. An mRNA transcribed from a gene is divided into three regions: 5' UTR, open reading frame (ORF), and 3' UTR. The recombinant gene of the present invention is a gene modified so as to encode mRNA containing a specific 5' UTR sequence. In other words, the gene is a recombinant gene encoding a specific 5' UTR sequence. It can also be said that the gene is a recombinant gene that expresses mRNA containing a specific 5' UTR sequence. The recombinant gene of the present invention is not a gene existing in nature (i.e., not a gene found in various species), but is a gene that is produced by artificially modifying a base sequence of a portion corresponding to at least the 5' UTR.

A protein is produced by translation of mRNA encoded by a gene. Therefore, it can be said that a gene encodes a protein. It can also be said that mRNA encodes a protein.

Because a gene is actually a DNA molecule, in the present description, the "gene" may be referred to as a "DNA molecule" as long as no contradiction occurs. For example, the recombinant gene can also be referred to as a recombinant DNA molecule. In detail, the recombinant gene of the present invention is a recombinant DNA molecule obtained by modifying (changing) the base sequence of DNA encoding mRNA. Further, preferably, the gene is an isolated recombinant DNA molecule. An mRNA molecule transcribed from the recombinant DNA molecule contains a specific 5' UTR sequence.

Further, the present invention also encompasses an artificial mRNA molecule having the specific 5' UTR sequence. The artificial RNA molecule may be obtained by transcription of the recombinant DNA molecule of the present invention or by chemical synthesis.

A method for artificially changing the base sequence of a gene can be suitably selected for use from various known methods. For example, the base sequence of a gene can be modified by the following techniques: cleaving a gene with appropriate restriction enzyme and subsequently ligating a new nucleic acid fragment to the cleavage site, designing a primer pair that is not completely complementary to a target gene and performing PCR, or using the above techniques in combination.

Most genes existing in nature are subject to repression of the translation of the mRNA into proteins when the genes are under environmental stresses such as heat stress or salt stress, compared to when the genes are under normal environment. The recombinant gene of the present invention can escape translational repression under environmental stresses (particularly heat stress and salt stress) by encoding a specific 5' UTR sequence. Specifically, because an mRNA molecule produced by transcription from the recombinant gene of the present invention (recombinant DNA molecule) contains the specific 5' UTR sequence, the mRNA molecule is capable of reducing environmental stress-induced repression of translation of the mRNA molecule into a protein, preferably capable of preventing translational repression, and more preferably capable of promoting translation.

The specific 5' UTR sequence is a 5' UTR sequence comprising a specific sequence of bases 1 to 7 from the 5' end and a specific base sequence from positions 12 to 32 from the 5' end. The base sequence from positions 8 to 11 from the 5' end in the specific 5' UTR sequence is not particularly limited. For example, each base from positions 8 to 11 from the 5' end can be any of adenine, uracil, guanine, and cytosine (A, U, G, and C). A preferable example is a base sequence from positions 8 to 11 from the 5' end of the 5' UTR contained in a naturally existing mRNA. A more preferable example is a base sequence from positions 8 to 11 from the 5' end of the 5' UTR contained in a naturally existing mRNA, wherein the mRNA encodes a protein that is expressed by allowing escape from environmental stress-induced translational repression by the recombinant gene of the present invention.

More specifically, the base sequences from positions 1 to 7 and positions 12 to 32 from the 5' end in the specific 5' UTR sequence are, respectively, the sequences from positions 1 to 7 and positions 12 to 32 of the base sequence of SEQ ID NO: 4, 6, 20, 36, or 60.

SEQ ID NO: 4 is a 5' UTR sequence of gene At4g14560, SEQ ID NO: 6 is a 5' UTR sequence of gene At1g77120, SEQ ID NO: 20 is a 5' UTR sequence of gene At3g15450, SEQ ID NO: 36 is a 5' UTR sequence of gene At4g12000, and SEQ ID NO: 60 is an optimal 5' UTR sequence predicted by the later-described method. Each 5' UTR sequence is as shown in Table 1. The bases from positions 8 to 11 in the predicted optimal sequence (SEQ ID NO: 60) are expressed by "n." The "n" indicates adenine, uracil, guanine, or cytosine (A, U, G, or C). In other words, n can be any of bases A, U, G, and C.

Further, the sequence of bases 1 to 7 and the sequence of bases 12 to 32 in each sequence are underlined in Table 1. In other words, the specific 5' UTR sequence is a 5' UTR sequence in which the sequence of bases 1 to 7 and the sequence of bases 12 to 32 from the 5' end are the base sequences indicated by the underlines in Table 1. Specifically, the specific 5' UTR is:

5' UTR in which bases 1 to 7 from the 5' end are acacaag (SEQ ID NO:1), and bases 12 to 32 from the 5' end are uucaaggauaucaaaucacaa (SEQ ID NO:85);

5' UTR in which bases 1 to 7 from the 5' end are uacauca (SEQ ID NO:3), and bases 12 to 32 from the 5' end are cacacaaacuaacaaaagau (SEQ ID NO:86);

5' UTR in which bases 1 to 7 from the 5' end are auaacac (SEQ ID NO:2), and bases 12 to 32 from the 5' end are caagcauuggauuaaucaaag (SEQ ID NO:87);

5' UTR in which bases 1 to 7 from the 5' end are auuaaca (SEQ ID NO:88), and bases 12 to 32 from the 5' end are aaccgaaaaaagaaaaaaacu (SEQ ID NO:89); or 5' UTR in which bases 1 to 7 from the 5' end are uuaaaaa (SEQ ID NO:7), and bases 12 to 32 from the 5' end are acaaaaaaaaaaaaaaaaaaa (SEQ ID NO:8).

TABLE 1

| AGI Code | 5' UTR Sequence | The Number of Bases in the 5' UTR | SEQ ID NO. |
|---|---|---|---|
| At4g14560 | acacaagcauuuucaaggauaucaaaucacaaucccaagaagagcaauaacaagagaagaagaaguaguuca agaauuaaggaagagagcuucuccguuaaaguauagugagagaau | 117 | 4 |
| At1g77120 | uacaucacaaucacacaaaacuaacaaaagaucaaaagcaaguucuucacuguugaua | 58 | 6 |
| At3g15450 | auaacacauuucaagcauuggauuaaucaaagacaaagaaaacgaaa | 47 | 20 |
| AT4g12000 | auuaacaaacaaaccgaaaaaagaaaaaaacucaucuuucuccaaaaucacacaaaucuucuuuauuuguuau ucucaauccuuccuucauccccagguuucuuucgauucguugagucauucaauuuuuccaucacugggauuuu cucucugaauccgaucggagaauccagucgauuacuaaucuagcgcucucuuuuuuucuacucg | 210 | 36 |
| Predicted Optimal Sequence | uuaaaaannnnacaaaaaaaaaaaaaaaaaaa | 32 | 60 |

Further, the length of the specific 5' UTR sequence is not particularly limited as long as the sequence comprises 32 bases or more. The sequence is preferably 32 to 250 bases long, more preferably 32 to 210 bases long, further more preferably 32 to 120 bases long, and still further preferably 32 to 60 bases long. Further, bases other than bases 1 to 7 and 12 to 32 from the 5' end are not particularly limited. Preferably, each base other than bases 1 to 7 and 12 to 32 from the 5' end is adenine, uracil, guanine, or cytosine (A, U, G, or C).

Further, the recombinant gene of the present invention encompasses a gene encoding 5' UTR that is obtained by replacing 1 or more (preferably 1 or more) bases in the above-described specific 5' UTR sequence, and that escapes translational repression induced by at least one environmental stress selected from the group consisting of heat stress and salt stress. Specifically, the recombinant gene of the present invention (recombinant DNA molecule) also encompasses a recombinant gene (recombinant DNA molecule) having the following features:

encoding mRNA comprising, as the 5' UTR, polynucleotides of a base sequence in which 1 or more (preferably 1 or more) bases in the above-described specific 5' UTR sequence are replaced, and escaping repression of translation of the mRNA into proteins, which is induced by at least one environmental stress selected from the group consisting of heat stress and salt stress.

The number of bases to be replaced in the 5' UTR sequence is preferably 1 to 9, more preferably 1 to 5, and further more preferably 1 to 3. Further, whether the recombinant gene can escape heat stress-induced and/or salt stress-induced translational repression can be determined by, for example, whether a protein encoded by the recombinant gene is produced in the same amount as when the protein is grown under normal conditions or in an amount greater than that when a vector obtained by ligating the recombinant gene to a site immediately downstream of the transcription initiation point of a promoter is introduced into a host (preferably a plant, more preferably dicotyledon, and further more preferably *Arabidopsis thaliana* or cell derived from these plants) to produce a transformant and the transformant is grown under heat stress and/or salt stress. In other words, when the protein can be produced in the same amount as when the protein is grown under normal conditions or in an amount greater than that, it can be determined that translational repression was prevented or promoted (see the Transformant section, described later, for each stress condition and normal condition). The amount of protein can be compared by, for example, polysome analysis, RT-PCR assay, and protein quantitation. These analyses can be performed in accordance with known methods. Further, protein quantitation can also be performed in accordance with a known method (for example, the Bradford method).

More specific and preferable examples of the specific 5' UTR sequence include a 5' UTR sequence comprising the sequence of SEQ ID NO: 4, 6, 20, 36, or 60 at the 5' end, and more preferable examples include a 5' UTR sequence comprising the sequence of SEQ ID NO: 4, 6, 20, 36, or 60.

As long as the recombinant gene of the present invention is a gene modified so as to encode the mRNA containing the specific 5' UTR sequence, the type of protein (including peptide) to be encoded by the gene is not particularly limited. Examples of proteins (including peptides) preferably include pharmacologically active proteins. Specific examples include enzymes, transcription factors, cytokine, membrane-binding protein, various peptide hormones (for example, insulin, growth hormone, and somatostatin), and proteins for medical use such as vaccines and antibodies, and the like. Further, the recombinant gene of the present invention may also be a gene prepared by ligating a reporter gene such as GFP or luciferase, or a peptide tag sequence such as a His tag or FLAG-tag (registered trademark) to a gene encoding the above-described protein, or may be an artificially designed chimeric gene.

A known gene (DNA molecule) can be used as a material for constructing the recombinant gene. Known gene sequences can be obtained, for example, from the database such as the sequence database GenBank managed by the National Center for Biotechnology Information (NCBI). Based on such sequence information, a gene (DNA molecule) can be isolated from various organisms by, for example, a common method such as PCR. Additionally, known genes are commercially available, for example, as a cDNA library or the like from various companies, and these genes can be purchased and used.

A gene to be used as a material for constructing the recombinant gene of the present invention is not particularly limited. However, a plant-derived gene is preferable, dicotyledon-derived gene is more preferable, and *Arabidopsis thaliana*-derived gene is further more preferable. Specifically, the protein encoded by the recombinant gene of the present invention (DNA molecule) is preferably a plant-derived protein, more preferably a dicotyledon-derived protein, and further more preferably an *Arabidopsis thaliana*-derived protein.

As described later, the recombinant gene of the present invention may be incorporated into a vector, and a transformant can be prepared by introducing the vector into a host. At this time, if the codon usage frequency in the host into which the vector is introduced is known, the base sequence of the ORF of the recombinant gene may be modified before introduction so as to match the codon usage frequency suitable for the host.

Vector

The vector of the present invention is a vector obtained by ligating the above-described recombinant gene of the present invention to a site immediately downstream of the transcription initiation point of a promoter. More specifically, the vector of the present invention is an expression vector obtained by ligating the recombinant gene of the present invention to a cloning vector containing a promoter sequence, at a position immediately downstream of the transcription initiation point of the promoter.

Examples of cloning vectors used include plasmid vectors, cosmid vectors, virus vectors, artificial chromosome vectors (for example, YAC, BAC, and PAC), and the like. Of these, plasmid vectors and virus vectors are preferable. Further, a cloning vector used can be suitably selected depending on the organism or cell (i.e., host) into which the vector is introduced so that the gene can express a protein. The vector of the present invention has features such that the expression of a protein encoded by the recombinant gene is not repressed under environmental stresses such as heat stress and/or salt stress, especially when the vector is introduced into a plant (including a plant cell). Therefore, of various cloning vectors, *Agrobacterium*-derived plasmid commonly used in plants is preferable, and *Agrobacterium*-derived plasmid containing T-DNA (Ti-plasmid) is more preferable.

A cloning vector containing a promoter sequence is used. The promoter sequence to be used can be suitably selected as needed depending on the type of the host. For example, when the host is an animal (including an animal cell), promoters such as a human cytomegalovirus-derived promoter (CMV promoter) and SV40 promoter can be used. Further, when the host is a plant (including a plant cell), promoters such as CaMV35S promoter, which is a cauliflower mosaic virus-derived promoter, and the like can be used. Additionally, when the host is a bacterium such as *Escherichia coli*, promoters such as T7 promoter, T3 promoter, SP6 promoter, tac promoter, lac promoter and the like can be used. When the host is yeast, promoters such as PGK promoter and the like can be used. When the host is an insect cell, promoters such as P10 promoter and the like can be used. The vector of the present invention has features such that the expression of a protein encoded by the recombinant gene is not repressed under environmental stresses such as heat stress and/or salt stress, especially when the vector is introduced into a plant (including a plant cell). Therefore, CaMV35S promoter is particularly preferable.

Further, the cloning vector preferably contains a group of genes that can be used as a selective marker such as a drug resistant gene.

A known cloning vector, particularly a cloning vector that can be purchased from various companies and prepared, can be used as the above-described cloning vector.

A known method can be used as a method for inserting and ligating the above-described recombinant gene to a cloning vector. For example, the above-described recombinant gene is amplified by PCR using a primer with restriction enzyme site, and the amplified gene is treated with restriction enzyme and ligated to a cloning vector treated with restriction enzyme to be introduced therein.

The vector of the present invention is obtained by ligating the above-described recombinant gene to a site immediately downstream of the transcription initiation point of a promoter. However, for example, when the above-described cloning technique that uses restriction enzyme is used, a restriction enzyme site will be present at a ligation site between the promoter sequence and the recombinant gene sequence. In such a case, inverse PCR is performed to remove the restriction enzyme site and the resulting amplification product is self-ligated, thereby obtaining a vector from which the restriction enzyme site at the ligation site is removed. In this case, a primer set used for the inverse PCR is preferably designed in such a manner that it allows a PCR amplification product to be self-ligated. Additionally, ligase, for example, may be used for self-ligation.

To "ligate the recombinant gene of the present invention to a site immediately downstream of the transcription initiation point of a promoter sequence" means to ligate the recombinant gene of the present invention to a promoter sequence so as to obtain a transcription product in which a base transcribed from the promoter sequence of 0, 1, 2, or 3 bases (preferably 0, 1, or 2 bases) is ligated to the 5' end (i.e., 5' UTR end) of the mRNA encoded by the recombinant gene of the present invention, when the recombinant gene of the present invention is expressed in the host. More specifically, it means to directly ligate the promoter sequence to the recombinant gene sequence of the present invention. In other words, it means to ligate the promoter sequence to the recombinant gene sequence of the present invention so that there are no extra base sequences therebetween. Even when the promoter sequence and the recombinant gene sequence of the present invention are directly ligated to each other as described above, there is a case where a small number of bases (for example, 1, 2, or 3 bases) in the promoter sequence are transcribed during gene expression. The vector of the present invention also encompasses a vector that allows such transcription to occur.

Transformant

The transformant of the present invention is a transformant comprising the vector of the present invention. More specifically, the transformant of the present invention is a transformant into which the vector of the present invention is introduced and thereby transformed by the vector of the present invention.

The organism or cell (host) into which the vector of the present invention is introduced is not particularly limited. However, because the vector of the present invention has features such that the expression of the recombinant gene is not repressed under environmental stresses such as heat stress and/or salt stress, especially when the vector is introduced into a plant (including a plant cell), the host is preferably a plant (including a plant cell). Additionally, in view of the storage and increased production of the vector and the like, the host is preferably a bacterium such as *Escherichia coli*.

Examples of plants include dicotyledon, more specifically, *Arabidopsis thaliana*, tobacco, soybeans, *chrysanthemum*, lettuce, and the like. Examples of plant cells include dicotyledon-derived cells, more specifically, *Arabidopsis thaliana*-derived cells, tobacco-derived cells, soybean-derived cells, *chrysanthemum*-derived cells, lettuce-derived cells, and the like. Further, a plant cell-derived protoplast is also included in plant cells used herein. Additionally, a plant body obtained by culturing a transformed plant cell is also included in the transformant of the present invention. Tumor tissues, shoots, hairy roots that resulted from transformation can be used as they are for cell culture, tissue culture, or organ culture. Further, they can be regenerated into plant bodies by administration of appropriate concentrations of plant hormones (auxin, cytokinin, gibberellin, abscisic acid, ethylene, brassinolide, etc.) by known plant tissue culture methods. Additionally, transformed plant bodies can be regenerated by the use of transformed plant cells. A method as follows is employed as a generation method: callus-like transformed cells are transferred to a medium having different hormones at different concentrations and cultured therein to form somatic embryos, thereby obtaining complete plant bodies. Examples of media used include LS and MS media.

Further, the method for introducing the vector of the present invention into a host is not particularly limited. Depending on the type of host and vector, a known method can be suitably selected as needed and used. Non-limiting examples of methods include electroporation, particle gun method, methods that use Ti plasmid (for example, binary vector method and leaf disc method) and the like.

Whether the vector has been incorporated into the host can be confirmed by the PCR method, the Southern hybridization method, the Northern hybridization method, or the like. For example, PCR is performed by preparing DNA from a transformant and designing DNA-specific primers. Then, the amplification product is subjected to agarose gel electrophoresis, polyacrylamide gel electrophoresis, capillary electrophoresis, or the like, and stained with ethidium bromide, a SYBR Green solution, or the like. Then, transformation can be confirmed by detecting the amplification product as one band. Furthermore, the amplification product can also be detected by performing PCR using primers labeled in advance with a fluorescent dye or the like. Furthermore, it is possible to employ methods in which the amplification product is bound to a solid phase such as a microplate and confirmed by fluorescence, enzymatic reaction, or the like.

The transformant of the present invention is transformed by the vector of the present invention. More specifically, in the transformant of the present invention, the recombinant gene of the present invention is transcribed from the vector of the present invention to produce mRNA, and a protein is translated from the mRNA. As described above, the recombinant gene of the present invention encodes the specific 5' UTR sequence and is capable of escaping or reducing translational repression under heat stress and/or salt stress. Therefore, the transformant of the present invention can preferentially produce a protein encoded by the recombinant gene of the present invention under heat stress and/or salt stress.

The heat stress described in the present description refers to the stress that is produced when a transformant is grown at a temperature higher than the normal temperature (room temperature: about 20 to 22° C.). However, preferably, it is a temperature that allows a transformant to survive. The temperature at which a transformant can survive can be suitably set according to the type of the protein to be expressed from the recombinant gene, the type of the host, and the like. More specifically, the temperature is preferably 25° C. or higher, more preferably 25 to 37° C., and further more preferably 25 to 32° C.

Further, the salt stress described in the present description refers to the stress that is produced when a transformant is grown at a salt concentration that is equal to or higher than that in the normal soil or medium (typically, sodium chloride (NaCl) concentration). However, preferably, it is a salt concentration that allows a transformant to survive. The salt concentration in the normal soil or medium is essentially 0 mM. The salt concentration that allows a transformant to survive can be suitably set according to the type of the protein to be expressed from the recombinant gene, the type of the host, and the like. More specifically, the salt concentration is preferably 50 mM NaCl or higher, more preferably 50 to 200 mM NaCl, and further more preferably 50 to 100 mM NaCl.

Method for Producing a Protein Using the Transformant

The present invention also encompasses a method for producing a protein encoded by the recombinant gene, the method comprising growing (culturing) the transformant of the present invention under at least one environmental stress selected from the group consisting of heat stress and salt stress. As a method for growing or culturing the transformant, the host may be grown or cultured under environmental stresses.

Under environmental stresses, expression of a protein is usually repressed at the translational level in most genes. Therefore, a protein encoded by the recombinant gene of the present invention can be efficiently expressed. Further, because expression of other proteins is repressed, the produced protein can be easily and efficiently purified. The produced protein can be purified in accordance with a known method such as, for example, chromatography. More specifically, for example, the produced protein can be purified by affinity chromatography that uses an antibody that recognizes the produced protein. Further, when the produced protein contains a tag sequence, the produced protein can be purified using the tag as a marker.

Further, when the host is a plant (including a plant cell), it is considered possible to preferentially produce a secondary metabolite, as the recombinant gene of the present invention encodes an enzyme necessary for the production of the secondary metabolite. Specifically, because plants produce various secondary metabolites, it may be possible to preferentially produce a desired secondary metabolite by modifying a site encoding 5' UTR in a gene of an enzyme necessary for the production of a secondary metabolite so as to obtain the recombinant gene of the present invention, producing a transformed plant comprising a vector obtained by ligating the recombinant gene to a site immediately downstream of the transcription initiation point of a promoter, and consequently supplying components used as materials for the secondary metabolite to the transformed plant under environmental stresses.

Still further, the present invention encompasses a method for producing a plant capable of escaping translational repression induced by at least one environmental stress selected from the group consisting of heat stress and salt stress, by introducing the above-described vector of the present invention into a plant (including a plant cell). The thus-produced plant can efficiently express a protein encoded by the recombinant gene of the present invention under the above-described environmental stresses. As described above, a known appropriate method can be selected and used as a method for introducing the vector.

Genetic Modification Method

The present invention also encompasses a method for preparing a recombinant gene (recombinant DNA molecule) capable of escaping or reducing repression of translation of a protein encoded under a stress environment (preferably under heat stress and/or salt stress), by modifying the base sequence of the region encoding the 5' UTR of a given gene so that the 5' UTR sequence encoded is converted to the specific 5' UTR sequence described above.

A gene whose base sequence of the region encoding the 5' UTR is modified is not particularly limited. Examples include a gene that encodes a protein that is similar to a protein encoded by the above-described recombinant gene. Further, such a gene can be obtained by a similar manner as the gene used as a material for the above-described recombinant gene.

The base sequence can be modified in accordance with a common method such as the above-described method, for example. In regard to other conditions, the conditions used for the preparation of the above-described recombinant DNA molecule can be similarly used.

Still further, the present invention also encompasses a method for escaping or reducing repression of translation of an encoded protein under a stress environment (preferably under heat stress and/or salt stress) by modifying the base sequence of the region encoding the 5' UTR of a given gene so that the 5' UTR sequence encoded is converted to the specific 5' UTR sequence described above.

A gene whose base sequence of the region encoding the 5' UTR is modified is not particularly limited. Examples include a gene that encodes a protein that is similar to a protein encoded by the above-described recombinant gene. Further, such a gene can be obtained by a similar manner as the gene used as a material for the above-described recombinant gene. The base sequence can be modified in accordance with a common method such as the above-described method, for example. In regard to other conditions, the conditions used for the preparation of the above-described recombinant DNA molecule can be similarly used.

Artificial mRNA Molecule

The present invention also encompasses the "mRNA containing a specific 5' UTR sequence molecule" described in the above section Recombinant Gene (Recombinant DNA Molecule). The mRNA molecule is an artificial construct (i.e., artificial mRNA molecule) and does not encompass an mRNA molecule existing in nature.

The artificial mRNA molecule may be obtained by the chemical synthesis or transcription of the recombinant DNA molecule of the present invention. For example, the above-described transformant is grown under environmental stresses (preferably under heat stress and/or salt stress), and mRNA is collected from transformant by a common method. In this way, the artificial mRNA molecule can be efficiently obtained.

As is the case with the above-described transformant, a protein encoded by the artificial mRNA molecule can be preferentially produced by introducing the artificial mRNA molecule into a cell (preferably plant cell or protoplast) by a common method and culturing the cell under environmental stresses (preferably under heat stress and/or salt stress). The transfection method and stress conditions may be the same as those described above, for example.

Method for Predicting Sequence Features of 5' UTR that Escape or Reduce Environmental Stress-Induced Translational Repression Still further, the present invention also provides a method for predicting sequence features of 5' UTR that escapes or reduces environmental stress-induced translational repression in plants, as well as providing a nucleic acid or the like containing the 5' UTR having the sequence features predicted by the prediction method. Specifically, the present invention encompasses, for example, the inventions according to Items A to F described below.

Item A. A method for predicting sequence features of a five prime untranslated region (5' UTR) that escapes or reduces environmental stress-induced translational repression in plants, the method comprising:

a step of determining the relative activity level of N number of genes naturally expressed in plants at the translational level of nucleic acid molecules each containing the 5' UTR under environmental stress conditions compared to that under control conditions;

a step of determining the appearance frequency of a base sequence consisting of t number of bases, which appears at least once in a sequence of length L from base positions k to k+L−1 from the 5' end of the 5' UTR;

a step of formulating an equation of correlation between the relative activity level and the appearance frequencies of the base sequences, and determining the regression coefficient for the appearance frequency of each base sequence by multivariate analysis;

a step of determining, using the regression coefficient, regression coefficient values corresponding to 4 bases, A, U, G, and C, at each base position in the region of length L from base positions k to k+L−1, and determining the degree of contribution of each base to the relative activity level at each base position;

a step of constructing a regression model by multivariate analysis, using the obtained degree of contribution and the relative activity level; and a step of selecting, from among the regression models constructed by varying k and L, a regression model between base position k' and length L' with the prediction accuracy for the relative activity level being equal to or higher than the set level, and predicting a specific sequence in the region from positions k' to k'+L'−1, using the selected regression model.

Item B. A nucleic acid sequence that escapes or reduces environmental stress-induced translational repression, the nucleic acid sequence comprising a 5' untranslated region derived from a gene that is naturally expressed in plants or its modified sequence, wherein the 5' untranslated region is a sequence in which the region from positions k' to k'+L'−1 specified in Item A in the 5' untranslated region derived from a gene that is naturally expressed in plants is the specific sequence defined in Item A;

and the modified sequence is a sequence in which the region from positions k' to k'+L'−1 specified in Item A in the 5' untranslated region derived from a gene that is naturally expressed in plants is replaced by the specific sequence defined in Item A.

Item C. A gene comprising the nucleic acid sequence defined in Item B

Item D. An expression vector comprising the nucleic acid sequence defined in Item B, wherein the nucleic acid sequence is ligated to a site immediately downstream of the transcription initiation point.

Item E. A transformant comprising the expression vector defined in Item D.

Item F. A transformed plant comprising the expression vector defined in Item D.

The sequence features of the five prime untranslated region (5' UTR) described herein means a specific sequence in the region from base positions k' to k'+L'−1 from the 5' end of the 5' UTR.

The present invention steps (1) to (6) described below provide a method for predicting sequence features of the 5' UTR that regulates translational control in response to environmental stresses (preferably heat stress and/or salt stress), using in silico analysis.

(1) First, the relative activity level of N number of genes that are naturally expressed in plants is determined at the translational level of nucleic acid molecules each containing the 5' UTR under environmental stress conditions compared to that under control conditions N indicates the number of gene samples and is an integer of 2 or greater.

Preferably, N number of genes includes several genes with different translational states. The translational state can be determined with reference to the results from the tests that exhaustively analyzed changes in the translational state of genes by, for example, polysome/microarray analysis or the like.

The nucleic acid molecule containing the 5' UTR is not particularly limited as long as the translational level can be measured. Examples thereof include synthetic mRNA into which a reporter gene such as f-luc gene is incorporated to the downstream of the 5' UTR.

The form of a nucleic acid molecule to be used for the measurement is also not particularly limited. For example, the above-described synthetic mRNA introduced into appropriate protoplasts may be used.

The environmental stress conditions refer to, for example, conditions with stress (preferably heat stress and/or salt stress) under an environment different from a normal environment, for example, an environment with high temperature, high osmotic pressure, high salt concentration, and the like. Further, in other words, control conditions refer to normal conditions similar to the environmental stress conditions except that environmental stresses are not imposed.

A technique to determine the relative activity level at the translational level is also not particularly limited and can be determined in accordance with a known technique. For example, a transient transformant is prepared using synthetic mRNA into which a reporter gene such as f-luc gene is incorporated in the downstream of the 5' UTR of a gene. The level of expression (the amount of translation) of the reporter gene is measured as the activity level when the transformant is placed under environmental stress conditions and when placed under control conditions, and the ratio can be regarded as the "relative activity level."

More specifically, the relative activity level can be determined by the method described in the Example.

(2) Next, the appearance frequency of a partial sequence consisting of t number of bases, which appears at least once in the sequence of length L from base positions k to k+L−1 from the 5' end of the 5' UTR, is determined.

The "k" is a variable that indicates the base position from the 5' end of the 5' UTR and is an integer of 1 to the total number of bases of the 5' UTR.

Further, "L" is a variable that indicates the base length from base position k and is an integer of 1 to the total number of bases of the 5' UTR.

Further, "t" is a value that indicates the number of consecutive bases in the partial sequence that appears at least once in the sequence of length L from k to k+L−1 and is an integer of 1 to L.

Using k, L, and t described above, sequences each consisting of t number of bases, which appear at least one in the sequence of length L from base positions k to k+L−1 in N number of samples, can be expressed as $R_1(t), R_2(t), \ldots, R_v(t), \ldots, R_V(t)$. Further, the appearance frequencies of these sequences can be expressed as $f_i^{(k, k+L-1)}(R_1(t)), \ldots, f_i^{(k, k+L-1)}(R_v(t)), \ldots f_i^{(k, k+L-1)}(R_V(t))$. The frequency of the $v^{th}$ sequence is expressed as variable $f_i^{(k,k+L-1)}(R_v(t))$.

(3) Next, an equation of correlation between the relative activity level and the appearance frequencies of the base sequences is developed, and a regression coefficient for the appearance frequency of each base sequence is formulated by multivariate analysis.

To formulate an equation of correlation is, in other words, to express the relative activity level as a function of the appearance frequencies of the base sequences. Consequently, a regression coefficient for the appearance frequency of each base sequence is determined.

As a method therefore, multivariate analysis such as partial least squares (PLS) is used.

As an example of multivariate analysis, partial least squares (PLS) analysis is described below, but methods are not limited thereto.

When the relative activity level is expressed as y, the equation of correlation between y and the variable of V number of sequence frequencies, $f^{(k, k+L-1)}(R_v(t))$, $(v=1, 2, \ldots, V)$ can be expressed by Equation (1).

$$y = a_{R_1(t)}^{(k,k+L-1)} f_i^{(k,k+L-1)}(R_1(t)) + a_{R_2(t)}^{(k,k+L-1)} f_i^{(k,k+L-1)}(R_2(t)) + \ldots + a_{R_v(t)}^{(k,k+L-1)} f_i^{(k,k+L-1)}(R_v(t)) + \ldots + a_{R_V(t)}^{(k,k+L-1)} f_i^{(k,k+L-1)}(R_V(t)) + a_{0(t)}^{(k,k+L-1)} \quad (1)$$

wherein $$a_{R_v(t)}^{(k,k+L-1)}$$

is a regression coefficient for the frequency of the $v^{th}$ base sequence.

The regression coefficient can be determined in the following manner by partial least squares (PLS).

For N number of samples, a sequence of length L from position k taken out from sample i is expressed as $Seq_i = s_{ik} s_{ik+1} \ldots s_{ik+L-1}$. Herein, the positions in the base sequence of sample i are expressed as $s_1, s_2, \ldots, s_k, \ldots, s_M$ in the direction from the 5' end to 3'.

The sequence of length t starting at position k+j in sample i is expressed as follows.

$$s_{ik+j} s_{ik+j+1}, \ldots, s_{ik+j+t-1} \equiv Seq_i(k+j, k+j+t-1)$$

$Seq_i(k+j, k+j+t-1)$ is compared with V number of sequences $R_v(t)$, $(v=1, 2, \ldots, V)$, and the identical sequence is expressed as $R_{(i, k+j)}$.

Herein, $R_{(i, k+j)}$ is expressed as follows.

$$R_{(i,k+j)} = r_{ik} r_{ik+1} r_{ik+2} \ldots r_{ik+j+t-1}$$

A PLS regression coefficient for $R_{(i, k+j)}$ is selected and expressed as follows.

$$a_{R_{(i,k+j)}}^{(k,k+L-1)}$$

In this way, the regression coefficient for the sequence can be determined.

(4) Next, using the regression coefficients, regression coefficient values corresponding to 4 bases (A, U, G, and C) at each position in the region of length L from base positions k to k+L−1 are determined, and the degree of contribution of each base at each base position to the relative activity level is determined.

Specifically, the following method is used.

A matrix is created by placing the regression coefficients obtained in step (3) in columns (k+j, k+j+1, . . . , k+j+t−1) of sample i. Consequently, averages of the regression coefficients with 4 bases (A, U, G, and C) at base position k+j and unbiased estimates of the variance are determined. Based on the average of each of the regression coefficients for the 4 bases (A, U, G, and C) at the position k+j and the unbiased estimate of the variance, a test is performed to determine whether the distribution of the regression coefficients corresponding to the 4 bases (A, U, G, and C) is considered to be statistically significantly positive or negative. Thereby, a base sequence that contributes to the relative activity level y either positively or negatively is extracted.

Examples of test methods include t-tests.

A base statistically significant to the relative activity level y is extracted for each base position. Thereby, it is possible to obtain information regarding what base at what position in the sequence of length L from base positions k to k+L−1 contributes to the relative activity level positively or negatively.

(5) Next, a regression model is constructed by multivariate analysis, using the obtained degree of contribution and the relative activity level.

In the PLS method, the factor X (N×V matrix) is linearly associated with the response y (N×1).

The factor X and the response Y can be expressed by the following Equations (5) and (6), using the degree of contribution of each base obtained in step (4) and the relative activity level obtained in step (1)

$$X = \sum_{k=1}^{D} t_k p_k^T + E \quad (5)$$

$$y = \sum_{k=1}^{D} t_k q_k + e \quad (6)$$

Herein, $p_k$ represents the weighted vector for the $k^{th}$ component in X, and $q_k$ represents the coefficient for the $k^{th}$ component in y. D is the number of components in PLS, $t_k$ is the $k^{th}$ latent variable, E is the residual of X, and e is the residual of y.

D representing the number of components in PLS is determined as the number of components when the prediction accuracy is the maximum, as the prediction accuracy is sequentially calculated by a leave-one-out cross-validation every time the number of components is increased.

The prediction accuracy can be calculated using indices, such as $Q^2$ value and the correlation coefficient between the predicted value and the actual value, which associate the predicted value based on leave-one-out cross-validation and the actual value.

$Q^2$ is a measure of the prediction accuracy of the model and can be expressed by the following Equation (7).

$$Q^2 = 1 - \frac{\sum (y_{obs} - \ddot{y}o_{pred})^2}{\sum y_{obs}^2} \quad (7)$$

Herein, $y_{obs}$ is the experimentally determined relative activity level, and $y_{pred}$ is the predicted value based on the constructed model.

Further, Equations (5) and (6) for PLS can be summarized into Equation (8).

$$y = Xa + f \quad (8)$$

At this time, a is the regression coefficient vector, and the elements of the vector are expressed as $a_j$ (j=1, 2, . . . , N). Additionally, f is the residual of y.

(6) Next, from among several regression models constructed by varying k and L, a regression model between base position k' and L' with the prediction accuracy for the relative activity level being equal to or higher than a set level is selected, and a specific sequence of the region from positions k' to k'+L'−1 is predicted, using the selected regression model.

In the regression model constructed in step (5), multiple regression models are constructed by changing the values of k and L. Then, a regression model between base position k' and L' with the prediction accuracy for the relative activity level being equal to or higher than the set level is selected from among the multiple regression models.

A known index can be used as the prediction accuracy. Examples thereof include $Q^2$ value. When the $Q^2$ value is used as the prediction accuracy, a region with a higher $Q^2$ value exhibits a higher prediction accuracy, and this region is considered to be directly influencing the translational state under environmental stress conditions. Therefore, base position k' and L' corresponding to a region that increases the prediction accuracy are selected, and a regression model between base position k' and L' is selected.

In other words, among variables k, k' is the constant with the prediction accuracy being equal to or higher than the set level. Among variables L, L' is the constant, with the prediction accuracy being equal to or higher than the set level. In other words, the region from k' to $k_1'+L_1'-1$ determined based on k' and L' is an important region for escaping or reducing environmental stress-induced translational repression in plants.

The set level can be suitably determined in accordance with the purpose. The set level is usually 0 or higher, preferably 0.5 or higher, more preferably 0.6 or higher, and particularly more preferably about 0.8 or higher.

It is possible to select several k's and L's in accordance with the prediction accuracy. Specifically, and $L_1'$ showing the highest prediction accuracy can be selected from k's and L's with the prediction accuracy being equal to or higher than the set level, and further, $k_2'$ and $L_2'$ showing the second-highest prediction accuracy can be selected.

Then, using and $L_1'$, it is possible to predict a specific sequence 1 in the region from base positions $k_1'$ to $k_1'+L_1'-1$, and further, using the $k_2'$ and $L_2'$, it is possible to predict a specific sequence 2 in the region from base positions $k_2'$ to $k_2'+L_2'-1$.

The "specific sequence" described herein refers to a base sequence determined by the selected regression model described above and is a base sequence with the prediction accuracy being equal to or higher than the set level. In other words, it is a base sequence having an excellent function of escaping or reducing environmental stress-induced translational repression in plants.

Figure 39:
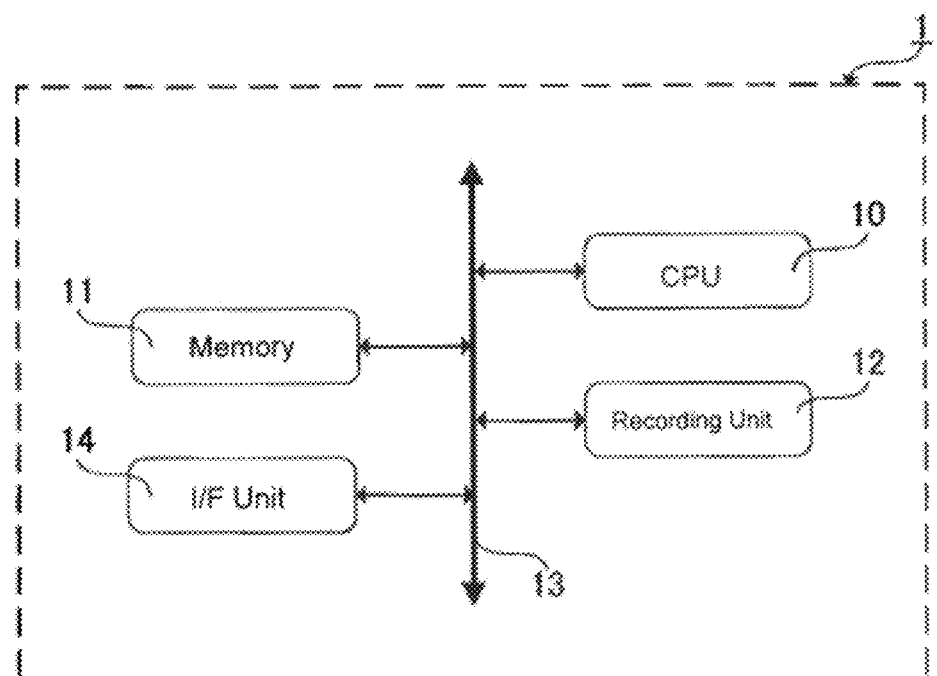
FIG. 39 shows a block diagram showing a schematic structure of a computer system that performs a process to achieve the prediction method of the present invention. A computer system 1 comprises a CPU 10 that calculates the data, a memory 11 used as a work area for calculation, a recording unit 12 that records calculation results, a bus 13 for transmitting data between each unit, and an interface unit 14 (shown as I/F units in the figure) that inputs and outputs data from and to an external device. Although not shown in the figure, the computer system also comprises operational devices (such as keyboard) and display units (such as display), with which a computer are commonly equipped. A process performed by the system 1 actually means the process performed by the CPU 10 of the system 1. The CPU 10 temporarily stores necessary data (such as interim data during the course of the process) using the memory 11 as the work area and suitably records data for long-term storage such as calculation results in the recording unit 12. Further, in the system 1, a program used to process each step of the prediction method of the present invention is recorded in advance in the recording unit 12 in, for example, an executable format (for example, a program converted from a programming language such as C by a compiler). The system 1 executes the process using the program recorded in the recording unit 12.

The prediction method of the present invention can be achieved, for example, by a computer system using a computer program. For example, it can be achieved by a calculator (computer system) shown in FIG. 39. In other words, the present invention also encompasses a prediction system for achieving the prediction method of the present invention. Specifically, the present invention includes a prediction system described below.

A system for predicting sequence features of a five prime untranslated region (5' UTR) that escapes or reduces environmental stress-induced translational repression in plants, the system comprising:

a means for determining the relative activity level of N number of genes naturally expressed in plants at the translational level of nucleic acid molecules each containing 5' UTR under environmental stress conditions compared to that under control conditions;

a means for determining the appearance frequency of a base sequence consisting of t number of bases, which appears at least once in the sequence of length L from base positions k to k+L−1 from the 5' end of the 5' UTR;

a means for formulating an equation of correlation between the relative activity level and the appearance frequencies of the base sequences, and obtaining a regression coefficient for the appearance frequency of each base sequence by multivariate analysis;

a means for determining, using the regression coefficient, regression coefficient values corresponding to 4 bases, A, U, G, and C at each position in the region of length L from base positions k to k+L−1, and determining the degree of contribution of each base to the relative activity level at each base position;

a means for constructing a regression model by multivariate analysis, using the obtained degree of contribution and the relative activity level; and a means for selecting, from among the regression models constructed by varying k and L, a regression model between base position k' and L' with the prediction accuracy for the relative activity level being equal to or higher than a set level, and predicting a specific sequence in the region from positions k' to k'+L'−1, using the selected regression model.

Further, the prediction method of the present invention can also include a step other than above-described steps (1) to (6) as long as the effect of the present invention is not impaired.

For example, it is possible to include a step of analyzing, by polysome/microarray analysis, changes in the translational state of a gene naturally expressed in plants between under control conditions and under environmental stress conditions.

The polysome/microarray analysis can be performed in accordance with a known technique. For example, plant cells under control conditions and under environmental stress conditions are subjected to polysome analysis using sucrose density gradient centrifugation, and RNA is extracted and purified from the polysome fraction and non-polysome fraction, followed by microarray analysis. Based on the obtained microarray analysis results, the ratio of the mRNA present in the polysome fraction to the total RNA or RNA present in the non-polysome fraction is determined. Thereby, the translational state of a gene in a plant can be exhaustively analyzed.

N number of genes to be used in step (1) can be selected based on the obtained results of the polysome/microarray analysis.

Further, the present invention can also include, if necessary, a known technique commonly used for in silico analysis and multivariate analysis.

Nucleic Acid Molecule Containing the Predicted 5' Untranslated Region or its Modified Sequence The present invention also encompasses a nucleic acid molecule containing the 5' untranslated region or its modified sequence having sequence features that can be determined by the prediction method. In other words, the present invention includes (1) a nucleic acid molecule containing the 5' untranslated region having the sequence features determined by the prediction method described in 1 above, and (2) a nucleic acid molecule containing a modified sequence of the 5' untranslated region having the sequence features determined by the prediction method described in 1 above.

The nucleic acid molecule of (1) is a nucleic acid molecule containing the 5' untranslated region derived from a gene naturally expressed in plants, and it is a nucleic acid molecule in which the region from positions k' to k'+L'−1 predicted by the above prediction method for the 5' untranslated region derived from a gene that is naturally expressed in plants contains the specific sequence predicted by the above prediction method.

Further, the nucleic acid molecule of (2) is a nucleic acid molecule containing a modified sequence of the 5' untranslated region derived from a gene naturally expressed in plants, and it is a nucleic acid molecule in which the modified sequence is a sequence whose region from positions k' to k'+L'−1 predicted by the above prediction method for the 5' untranslated region derived from a gene that is naturally expressed in plants is replaced by the specific sequence predicted by the above prediction method.

For example, in the case of *Arabidopsis thaliana*, in accordance with the prediction method of the present invention, the sequence of SEQ ID NO: 1 (acacaag) in the Sequence Listing, the sequence of SEQ ID NO: 2 (auaacac) in the Sequence Listing, or the sequence of SEQ ID NO: 3 (uacauca) in the Sequence Listing is predicted as the sequence of k=1 and L=7 in the 5' untranslated region, i.e., the specific sequence of bases 1 to 7 at the 5' end.

Based on the above, examples of sequences of the nucleic acid molecule of the present invention containing the predicted 5' untranslated region include sequences of a 5' UTR 1 (good (1)): the sequence of SEQ ID NO: 4 in the sequence listing acacaagcauuuucaaggauaucaaaucacaaucccaagaagagcaauaacaagagaagaagaag uaguucaagaauuaaggaagagagcuucuccguuaaaguauagugagagaau a 5' UTR 2 (good (2)): the sequence of SEQ ID NO: 5 in the sequence listing auaacacauuucaagcauuggauuaaucaaagacaaagaaaacgaaa, and a 5' UTR 3 (good (3)): the sequence of SEQ ID NO: 6 in the sequence listing uacaucacaaucacacaaaacuaacaaaagaucaaaagcaaguucuucacuguugaua.

Further, in the case of *Arabidopsis thaliana*, in accordance with the prediction method of the present invention, the sequence of SEQ ID NO: 7 (uuaaaaa) in the Sequence Listing is predicted as the sequence of k=1 and L=7 in the 5' untranslated region, i.e., one of the specific sequences of bases 1 to 7 at the 5' end.

Further, the sequence of SEQ ID NO: 8 (acaaaaaaaaaaaaaaaaaaa) in the Sequence Listing is predicted as the sequence of k=12 and L=21 in the 5' untranslated region, i.e., one of the specific sequences of bases 12 to 32 at the 5' end.

Based on the above, examples of the nucleic acid molecule of the present invention comprising a modified sequence of the predicted 5' untranslated region include a modified 5' UTR 1: a nucleic acid molecule in which the sequence of bases 1 to 7 from the 5' in the 5' untranslated region derived from a gene that is naturally expressed in plants is replaced by the sequence of SEQ ID NO: 7 (uuaaaaa) in the Sequence Listing;

a modified 5' UTR 2: a nucleic acid molecule in which the sequence of bases 12 to 32 from the 5' in the 5' untranslated region derived from a gene that is naturally expressed in plants is replaced by the sequence of SEQ ID NO: 8 (acaaaaaaaaaaaaaaaaaaa) in the Sequence Listing; and a modified 5' UTR 3: a nucleic acid molecule in which the sequence of bases 1 to 7 from the 5' in the 5' untranslated region derived from a gene that is naturally expressed in plants is replaced by the sequence of SEQ ID NO: 7 (uuaaaaa) in the Sequence Listing, and the sequence of bases 12 to 32 from the 5' is replaced by the sequence of SEQ ID NO: 8 (acaaaaaaaaaaaaaaaaaaa) in the Sequence Listing.

The nucleic acid molecule of the present invention containing the predicted 5' untranslated region or its modified sequence having the above-described sequence features is characterized in that it can escape or reduce environmental stress-induced translational repression in plants.

In normal plants, the translation of the majority of mRNAs to proteins is repressed under environmental stresses. However, when the nucleic acid molecule of the present invention containing the predicted 5' untranslated region or its modified sequence is introduced, it is possible to escape translational repression under environmental stress conditions and maintain protein synthesis.

The present invention also encompasses a gene comprising nucleic acid sequence comprising the 5' untranslated region predicted in the present invention or its modified sequence.

The gene of the present invention encompasses a coding sequence of a protein, in addition to the nucleic acid sequence comprising the predicted 5' untranslated region or its modified sequence.

The gene of the present invention comprises the nucleic acid sequence of comprising the 5' untranslated region predicted in the present invention or its modified sequence, and the gene thereby has the following characteristic: environmental stress-induced translational repression is escaped or reduced, and the protein synthesis ability is maintained also under environmental stress conditions.

The present invention also encompasses an expression vector into which the nucleic acid molecule is inserted. The type of the vector, method for inserting the nucleic acid molecule into the vector, form of ligation of the nucleic acid molecule and the vector, and the like are as described above.

The present invention also encompasses a transformant that can be obtained by introducing the expression vector into the host. The type of the host, method for introduction into the host, and the like are as described above.

A region important to the translational control under environmental stresses can be adequately predicted by the prediction method of the present invention.

The prediction method of the present invention is a method for predicting features of a sequence in the 5' UTR important to the translational control under environmental stresses. Experimental tests confirmed that the method can highly accurately predict an important region in the 5' UTR that escapes environmental stresses-induced translational repression (Examples).

EXAMPLES

The present invention is described in detail below, but is not limited to the following Examples. Among the genes used, the sequences of the genes identified by AGI codes can be obtained, for example, from the website of the *Arabidopsis thaliana* Information Resource (TAIR).

1. Materials and Method 1-1. Cultured Cells Used

*Arabidopsis thaliana* cultured cells (*Arabidopsis thaliana* T87) were supplied from the Plant Cell Bank in Riken Gene Bank. 95 mL of modified LS medium (Nagata, T. et al., 1992. Int. Rev. Cytol. 132: 1-30) was placed in a 300-mL Erlenmeyer flask, and cultivation was performed under the following conditions: 22° C., 18-hour light period/6-hour dark period, and a stirring rate at 120 rpm. Every week, 4 mL of cells that entered stationary phase were transplanted onto 95 mL of fresh medium and subcultured. 8 mL of transplanted cells cultured for 3 days were used for the experiment. Additionally, cells obtained by subculturing 2 mL of cells that entered stationary phase and by culturing the cells for 3 to 4 days were used as cultured cells to create stably transformed cells, which are described later.

1-2. Genetic Operation

Genetic operation using *Escherichia coli* was performed in accordance with a known method (for example, a method described in Molecular Cloning (Sambrook et al., 2001)).

1-3. Plasmid Construction pT3-FL-pA vector as template for a vector for firefly luciferase (hereinafter referred to as "f-luc") and pT3-RL-pA vector as a template for a vector for *renilla luciferase* (hereinafter referred to as "r-luc") were prepared by the following method.

Forward primers for both f-luc and r-luc were designed so as to contain the restriction enzyme sites and sequence for T3 promoter at the upstream of ATG corresponding to the initiation codon, which are described below.

(SEQ ID NO: 9)
5' GCGCGCAATTAACCCTCACTAAAGGTCTAGAGGATCCATG---3'
   BssHII      T3 promoter       XbaI BamHI Further, backward primers for both f-luc and r-luc were also designed so as to contain restriction enzyme sequences shown below at the downstream of TAA corresponding to the termination codon.

(SEQ ID NO: 10)
5' GCGCGCATCGATGAATTCACTAGTTTA---3'
   BssHII BamIII EcoRI SpeI

PCR products of these primers were inserted into the gap of BssHII sites in pBluescript II SK(-) (Stratagene), thereby obtaining templates for in vitro synthesis containing a T3 promoter sequence, i.e., plasmid pT3-FL (for f-luc mRNA) and pT3-RL (for r-luc mRNA). Further, as for the plasmid to synthesize mRNA containing a poly-A sequence at the 3' end, a double-strand fragment produced by annealing the following synthetic oligonucleotide (SEQ ID NO: 11)
5' AATTCAAAAAAAAAAAAAAAAAAAAAAAAAAAAAAAAAAAAAAAAAAAAAATATTAT 3'
   EcoRI                                              SspI BanIII (SEQ ID NO: 12)
5' CGATAATATTTTTTTTTTTTTTTTTTTTTTTTTTTTTTTTTTTTTTTTTTTTTTTTG 3'
   BanIII SspI                                              EcoRI was inserted into the EcoRI and BanIII sites of pT3-FL and pT3-RL. The thus-obtained plasmids were regarded as pT3-FL-pA and pT3-RL-pA.

The coding region in firefly luciferase was amplified by PCR reaction using the above-described pT3-FL-pA as a template.

The forward primer was designed so as to contain the BssHII and NcoI restriction enzyme sites at the upstream of ATC corresponding to the initiation codon. Additionally, the downstream sequence of the initiation codon was partially mutated (GACGCC→GACGTC) so as to generate the AatII site. Because of the mutation, the 3rd alanine in f-luc will be converted to valine.

The backward primer was designed to be located at positions 602 to 626 in the coding region so as to contain the NspV site located in the f-luc coding sequence.

Each PCR product was digested with BssHII and NspV and inserted into the BssHII and NspV sites of pT3-FL-pA vector, thereby obtaining plasmid pFL-pA as a template for in vitro synthesis.

NspV was partially degraded.

For the 5' UTR sequence to be tested, a primer was designed to have NcoI site and T3 promoter at the 5' end and AatII site at the 3' end and was prepared based on the sequence information organized by Kawaguchi et al. (NPL 4). Then, a fragment was amplified.

Further, the sequence with a partially replaced 5' UTR sequence was prepared as a PCR-amplified fragment or a synthetic oligonucleotide, using a primer for introducing mutation, and inserted into the NcoI and AatII sites of pFL-pA. As a result, plasmids (pT3-5' UTR-FL-pA) for in vitro transcription, to which various types of 5' UTR sequences are individually connected, were obtained.

FIG. 1 shows a schematic diagram of plasmid construction. As shown in FIG. 1, a DNA fragment in which the 5' UTR sequence to be tested is ligated to the downstream of the T3 promoter was inserted into the plasmid for f-luc mRNA synthesis, using the NcoI and AatII sites. In the in vitro synthesized f-luc mRNA, GG derived from the T3 promoter is added to the 5' end of the 5' UTR to be tested.

1-4. Synthesis of mRNA

Prior to in vitro transcription reaction, each of the plasmids (pT3-5' UTR-FL-pA and pT3-RL-pA) for in vitro transcription comprising a poly-A sequence was converted to a linear form by cutting the end portion of the poly-A sequence with SspI (AATATT). Accordingly, the 3' end of mRNA to be synthesized includes 1 thymine residue, in addition to 49 adenine residues (poly-A sequence). The SspI-treated DNA fragment was purified using a QIAquick PCR Purification Kit (Qiagen). Using the purified DNA fragment as a template, uncapped mRNA was synthesized using a Megascript T3 transcription kit (Ambion). Synthesis was performed following the protocol accompanying the kit. The synthesized RNA was treated with DNaseI supplied in the kit, purified by LiCl precipitation, and then dissolved in RNase-free water supplied in the kit. A cap structure was added using a ScriptCap $m^7G$ Capping System (Epicentre). The operation was performed following the protocol accompanying the kit. The capped RNA was purified using an RNeasy kit (Qiagen) and dissolved in RNase-free water. The RNA concentration was measured using a spectrophotometer. The RNA quality was tested by 1.5% denaturing agarose gel electrophoresis.

1-5. Protoplast Preparation from *Arabidopsis thaliana* Cultured Cells

Protoplast preparation from *Arabidopsis thaliana* cultured cells (T87) was performed by adding slight modifications to the method of Satoh et al. (Satoh J. et al., 2004, J. Biosci. Bioeng. 1: 1-8).

After the cultured cells were washed with 0.4 M mannitol, an enzyme solution (0.4 M mannitol, 10% cellulase RS (Yakult Honsha), 0.1% pectolyase (Kikkoman), pH 5.5) was added to the cells, followed by gentle stirring at 25° C. for 2 hours. After filtration through 40-μm nylon mesh (cell strainer; BD Falcon), centrifugation was performed (800 rpm, 5 min., 4° C.), thereby collecting a precipitate. 0.4 M mannitol was added to the collected precipitate, followed by recentrifugation (800 rpm, 5 min., 4° C.), thereby obtaining protoplasts. Further, after washing with 0.4 M mannitol, protoplasts were resuspended in W5 solution (154 mM NaCl, 125 mM $CaCl_2$, 5 mM KCl, 2 mM Mes-KOH, pH 5.6) and allowed to stand for 30 minutes in ice. The number of cells was counted using a hemocytometer. Protoplasts were collected by recentrifugation and suspended in MMg solution (0.4 M mannitol, 15 mM $MgCl_2$, 4 mM Mes-KOH, pH 5.7) to obtain a cell concentration of $1 \times 10^4$ cells/μL.

1-6. Introduction of mRNA into Protoplasts

Introduction of mRNA into protoplasts was performed essentially in accordance with the method using polyethylene glycol (PEG) of Kovtun (Kovtun et al., 2000, Proc. Natl. Acad. Sci. U.S.A. 6: 2940-2945). Typically, after adding $1 \times 10^4$ cells/μL of protoplasts to mRNA (about 5 μL), PEG solution (40% PEG 4000, 0.2 M mannitol, 0.1 M Ca $(NO_3)_2$) (Sheen J., 2001, Plant Physiol. 127: 1466-1475) of the same amount as that of the mixture solution was added to the mixture and slowly mixed. After allowing to stand for 5 minutes at room temperature, W5 solution was added thereto, followed by upside-down mixing. Cells collected by centrifugation were resuspended in protoplast medium (Dansako et al., 2003. J. Biosci. Bioeng. 95: 52-58). The resuspended cells were allowed to stand for a certain period of time at a test temperature, and centrifugation was performed using a microcentrifuge to remove the supernatant. Subsequently, the resulting product was frozen in liquid nitrogen and stored at −80° C.

1-7. Measurement of Luciferase Enzyme Activity

Cells were dissolved using 75 μL of passive lysis buffer (Promega) per $5 \times 10^5$ protoplasts, with a mixer for 15 minutes at room temperature. The f-luc and r-luc activities in the lysate were measured using a dual-luciferase reporter assay system (Promega) and a luminometer (Lumat LB 9501; Berthold), following the accompanying protocol.

2 Extraction of Sequence Information Associated with the Relative Activity Level 2-1 Definition of Sequence Information and Activity Information Hereinafter, the term "relative activity level" is used to express the relative f-luc activity level of protoplasts between when the protoplasts were allowed to stand under normal temperature (22° C.) and when the protoplasts were allowed to stand under heat stress conditions (37° C.) (specifically, the f-luc activity level of protoplast allowed to stand under temperature (22° C.) relative to the f-luc activity level of protoplast allowed to stand under heat stress conditions (37° C.)), which is determined in the experiments in accordance with methods 1-1 to 1-7 described above. (In other words, the transient expression experiment in which several genes with a different translational state are extracted, and reporter mRNAs carrying the 5' UTRs of these genes are introduced into cultured cell protoplasts.)

The relationship between the sequence of length L from base positions k to k+L−1 and the relative activity level y in N number of samples was expressed by a mathematical model, and a base sequence feature that is most associated with the relative activity level was extracted from the mathematical model.

First, a sequence of length L from position k taken out from sample i was expressed as $Seq_i = s_{ik} s_{ik+1} \ldots s_{ik+L-1}$. Herein, the positions in the base sequence of sample i were expressed as $s_1, s_2, \ldots, s_k, \ldots, s_M$ in the direction from the 5' end to 3'. Further, the relative activity level of sample i was expressed as $y_i$.

FIG. 2 shows the relationship between the sequence information and the definition of the relative activity level.

2-2 Construction of Regression Equations to Explain the Relative Activity Level Based on the Frequency of Consecutive Bases Sequences each consisting of t number of bases, which appear at least once in the sequence of length L from base positions k to k+L−1 in N number of samples, were expressed as $R_1(t), R_2(t), \ldots, R_v(t), R_V(t)$. In this experiment, t=3.

Further, the appearance frequencies of these sequences were expressed as $f_i^{(k, k+L-1)}(R_1(t)), \ldots, f_i^{(k, k+L-1)}(R_v(t)), \ldots, f_{i(k, k+L-1)}(R_V(t))$.

Herein, the frequency of the $v^{th}$ sequence was expressed as variable $f^{(k, k+L-1)}(R_v(t))$ FIG. 3 shows the frequencies of sequences consisting of t number of consecutive bases $(R_1(t), R_2(t), \ldots, R_v(t))$ in the sequence of a range [k,k+L−1] having a length L in N number of samples.

Next, the linear relationship between relative activity, y, and V sequence frequency variables $f^{(k, k+L-1)}(R_v(t))$, $(v=1, 2 \ldots, V)$ is expressed in Equation (1).

$$y = a_{R_1(t)}^{(k,k+L-1)} f^{(k,k+L-1)}(R_1(t)) + a_{R_2(t)}^{(k,k+L-1)} f^{(k,k+L-1)}(R_2(t)) + \ldots + a_{R_v(t)}^{(k,k+L-1)} f^{(k,k+L-1)}(R_v(t)) + \ldots + a_{R_V(t)}^{(k,k+L-1)} f^{(k,k+L-1)}(R_V(t)) + a_{0(t)}^{(k,k+L-1)} \quad (1)$$

Herein, $$a_{R_v(t)}^{(k,k+L-1)}$$

is the regression coefficient for the frequency of the $v^{th}$ base. Further, the contribution to the relative activity level in the sequence region was compared based on $Q^2$ determined by the calculation of the regression coefficient, which is described in section 2-4.

2-3 Extraction of Base Information, Using the Equation of Correlation between the Sequence Frequency and the Relative Activity A sequence of length t starting at k+j in sample i was expressed as follows.

$$s_{ik+j} s_{ik+j+1}, \ldots, s_{ik+j+t-1} \equiv \text{Seq}_i(k+j, k+j+t-1)$$

$\text{Seq}_i(k+j, k+j+t-1)$ was compared with V number of sequences $R_v(t)$, $(v=1, 2, \ldots, V)$, and the identical sequence was expressed as $R_{(i, k+j)}$. Herein, $$R_{(i,k+j)} = r_{ik} r_{ik+1} r_{ik+2} \ldots r_{ik+j+t-1}$$

Further, a PLS regression coefficient for $R_{(i, k+j)}$ was selected and expressed as follows.

$$a_{R_{(i,k+j)}}^{(k,k+L-1)}$$

Figure 4:
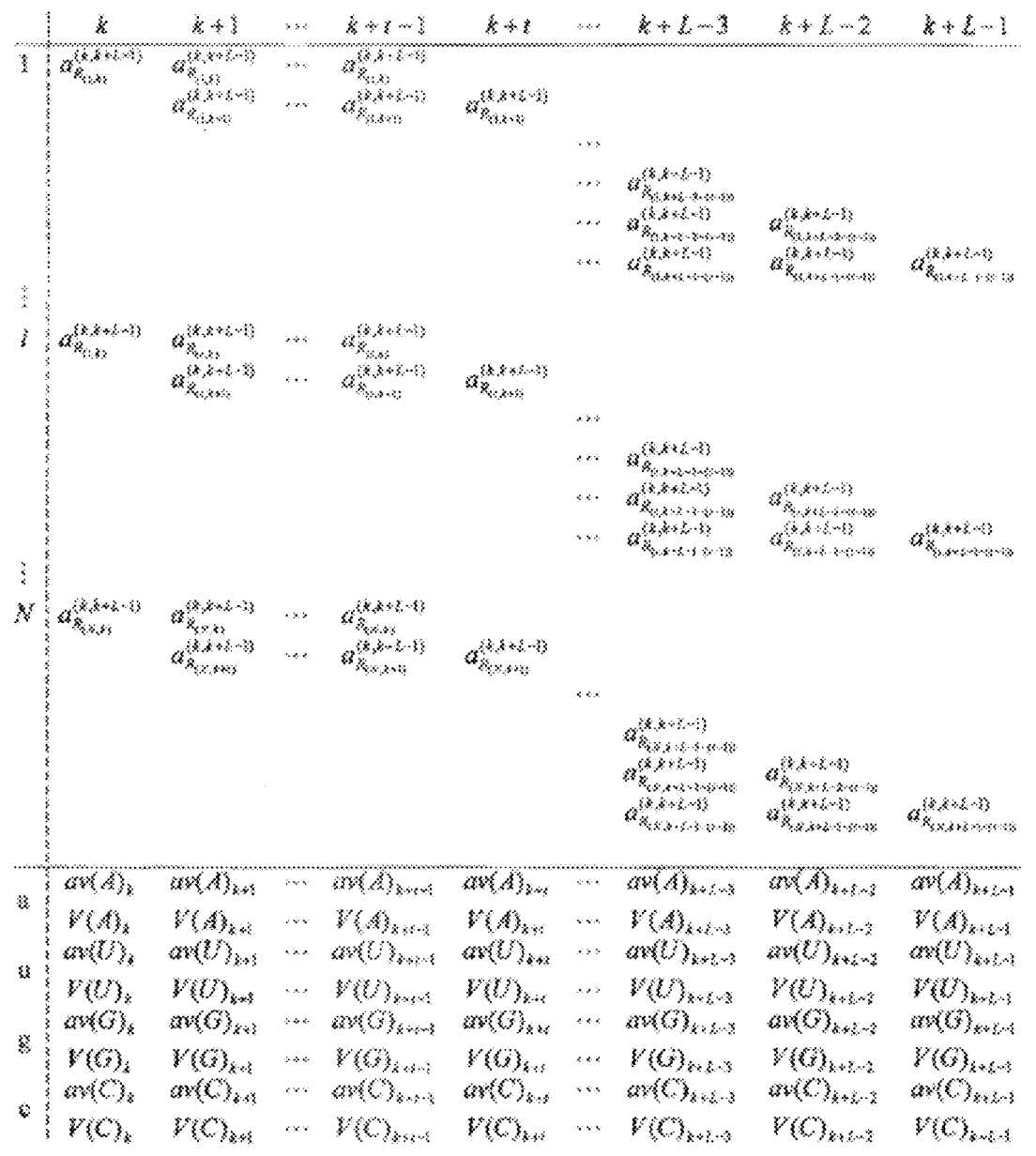

A matrix was created by placing these regression coefficients into columns (k+j, k+j+1, . . . k+j+t−1) in sample i (see the upper column in FIG. 4).

Consequently, averages of the regression coefficients with 4 bases (A, U, G, and C) at base position k+j and unbiased estimates of the variance were respectively expressed as $av(A)_{k+j}$, $av(U)_{k+j}$, $av(G)_{k+j}$, $av(C)_{k+j}$, and $V(A)_{k+j}$, $V(U)_{k+j}$, $V(G)_{k+j}$, and $V(C)_{k+j}$. Specifically, they were expressed as follows.

$$av(A)_{k+j} = \frac{\sum_{\substack{r_{ik+j}=A \\ i=1,2,\ldots,N}} a_{R_{(i,k+j)}}^{(k,k+L-1)}}{n(s_{ik+j} = A)} \quad (2.1)$$

$$av(U)_{k+j} = \frac{\sum_{\substack{r_{ik+j}=U \\ i=1,2,\ldots,N}} a_{R_{(i,k+j)}}^{(k,k+L-1)}}{n(s_{ik+j} = U)} \quad (2.2)$$

$$av(G)_{k+j} = \frac{\sum_{\substack{r_{ik+j}=G \\ i=1,2,\ldots,N}} a_{R_{(i,k+j)}}^{(k,k+L-1)}}{n(s_{ik+j} = G)} \quad (2.3)$$

$$av(C)_{k+j} = \frac{\sum_{\substack{r_{a+j}=C \\ i=1,2,\ldots,N}} a_{R_{(i,k+j)}}^{(k,k+L-1)}}{n(s_{ik+j} = C)} \quad (2.4)$$

and $$V(A)_{k+j} = \frac{\sum_{\substack{r_{a+j}=A \\ i=1,2,\ldots,N}} \{a_{R_{(i,k+j)}}^{(k,k+L-1)} - av(A)\}}{n(s_{ik+j} = A) - 1} \quad (3.1)$$

$$V(U)_{k+j} = \frac{\sum_{\substack{r_{a+j}=U \\ i=1,2,\ldots,N}} \{a_{R_{(i,k+j)}}^{(k,k+L-1)} - av(U)\}}{n(s_{ik+j} = U) - 1} \quad (3.2)$$

$$V(G)_{k+j} = \frac{\sum_{\substack{r_{a+j}=G \\ i=1,2,\ldots,N}} \{a_{R_{(i,k+j)}}^{(k,k+L-1)} - av(G)\}}{n(s_{ik+j} = G) - 1} \quad (3.3)$$

$$V(C)_{k+j} = \frac{\sum_{\substack{r_{a+j}=C \\ i=1,2,\ldots,N}} \{a_{R_{(i,k+j)}}^{(k,k+L-1)} - av(C)\}}{n(s_{ik+j} = C) - 1} \quad (3.4)$$

Based on the averages (Equations (2.1-2.4)) of the regression coefficients corresponding to the 4 bases (A, U, G, and C) at position k+j and the unbiased estimates of the variance (Equations (3.1-3.4)), a test was performed to determine whether the distribution of the regression coefficients corresponding to the 4 bases (A, U, G, and C) is considered to be statistically significantly positive or negative. Thereby, a base sequence that contributes to the relative activity level y either positively or negatively was extracted.

In this analysis, a t-test was performed to extract a base statistically significant to the relative activity level y at each base position. The t-statistic was expressed by Equation (4).

$$t(\text{base})_{k+j} = \frac{|av(\text{base})_{k+j}|}{\sqrt{\frac{V(\text{base})_{k+j}}{n(s_{ik+j} = \text{base})}}} \quad (4)$$

Herein, the base corresponds to each of A, U, G, and C.

Herein, $t(\text{base})_{k+j}$ usually follows a t-distribution with degree of freedom $\phi=n-1$ ($s_{ik+j}$=base). Accordingly, the significance level $p(\text{base})_{k+j}$ corresponding to $t(\text{base})_{ik+j}$ was obtained from the t-distribution of $\phi=n-1$ ($s_{ik+j}$=base). This $p(\text{base})_{k+j}$ is the probability that the regression coefficient for the base corresponding to at k+j is considered to be 0 by chance. Accordingly, it is possible to obtain information regarding what base at what position in the sequence of length L from base positions k to k+L−1 contributes to the relative activity level positively or negatively.

FIG. 4 shows the regression coefficients at base position j+k as well as the averages of the regression coefficients corresponding to the 4 bases and unbiased estimates of the variance.

2-4 Calculation of Regression Coefficients by PLS

Based on the obtained sequence information and the relative activity level, a regression model was constructed by the partial least squares (PLS) method. The PLS method is a method in which the factor X (N×V matrix) is linearly associated with the response y (N×1).

PLS was expressed by the following Equations (5) and (6).

$$X = \sum_{k=1}^{D} t_k p_k^T + E \qquad (5)$$

$$y = \sum_{k=1}^{D} t_k q_k + e \qquad (6)$$

Herein, $p_k$ represents the weighted vector for the $k^{th}$ component in X, and $q_k$ represents the coefficient for the $k^{th}$ component in y. D is the number of components in PLS, $t_k$ is the $k^{th}$ latent variable, E is the residual of X, and e is the residual of y. D representing the number of components in PLS is determined as the number of components when the value of $Q^2$ is the maximum, as the value of $Q^2$ is sequentially calculated by a leave-one-out cross-validation every time the number of components is increased. $Q^2$ is a measure of the prediction accuracy of the model, and was expressed by the following Equation (7).

$$Q^2 = 1 - \frac{\sum (y_{obs} - \ddot{y}o_{pred})^2}{\sum y_{obs}^2} \qquad (7)$$

Herein, $y_{obs}$ is the experimentally determined measured value, and $y_{pred}$ is the predicted value based on the constructed model. Further, Equations (5) and (6) for PLS can be summarized into Equation (8).

$$y = =Xa+f \qquad (8)$$

At this time, a is the regression coefficient vector, and the elements of the vector are expressed as $a_j (j=1, 2, \ldots, N)$. Additionally, f is the residual of y.

3. Relationship between Selective Translation under Heat Stress and the 5' UTR 3-1. Selection of 39 Genes Used for the Test In order to perform genome-wide analysis of environmental stress-induced changes in the translational state in plants, 19,099 genes derived from normal cells and stress-treated cells of *Arabidopsis thaliana* were subjected to polysome/microarray analysis.

First, normal cells and heat stress-treated (37° C., 10 min.) cells obtained by dividing cultured cells obtained by culturing under the same conditions were subjected to polysome analysis using sucrose density gradient centrifugation. It was confirmed based on the absorbance profile that heat stress treatment causes a decrease in the polysome fractions simultaneously with an increase in the non-polysome fraction. RNA was extracted and purified from the polysome fraction and non-polysome fraction. Using the purified RNA as a template, antisense RNA (aRNA) fluorescently labeled with Cy3 (polysome fraction) or Cy5 (non-polysome fraction) was prepared and subjected to competitive hybridization with probes on Agilent oligoarray (*Arabidopsis thaliana* 3 oligo microarray 44K; Agilent Technologies). Based on the thus-obtained microarray data, the polysome score (log ratio of polysome fraction [Cy3]/non-polysome fraction [Cy5]) and the polysome ratio (corresponding to Cy3/[Cy3+Cy5]) that indicates the percentage (%) of the mRNA present in the polysome fraction were calculated as indices indicating the translational state (state of polysome formation) of each mRNA species.

The polysome score of normal cells was determined by the following equation.

$$PS_{con} = \text{Log}(\text{poly}_{con}/\text{nonpoly}_{con})$$

In the above equation, $\text{poly}_{con}$, con represents the cyanine 3 (Cy3) signal value in microarray data derived from normal cells, in other words, the amount of mRNA present in the polysome fraction in normal cells. Further, $\text{nonpoly}_{con}$, con represents the cyanine 5 (Cy5) signal value in microarray data derived from normal cells, in other words, the amount of mRNA present in the non-polysome fraction in normal cells.

Additionally, the polysome score of heat stress-treated cells was determined by the following equation.

$$PS_{heat} = \text{Log}(\text{poly}_{heat}/\text{nonpoly}_{heat})$$

In the above equation, $\text{poly}_{heat}$ represents the Cy3 signal value derived from high-temperature stress-treated cells, in other words, the amount of mRNA present in the polysome fraction in heat stress-treated cells. Further, $\text{nonpoly}_{heat}$ represents the Cy5 signal value derived from high-temperature stress-treated cells, in other words, the amount of mRNA present in the non-polysome fraction in heat stress-treated cells.

Further, as an index for evaluating changes in the translational state caused by heat stress treatment, $\Delta PS$ expressed by the following equation was determined for each gene.

$$\Delta PS = PS_{heat} - PS_{con}$$

Further, mRNAs of 19,099 genes were ranked according to the size of $\Delta PS$.

Specifically, the greater the $\Delta PS$ value is, the higher the ranking is, and the smaller the value is, the lower the ranking is. A greater $\Delta PS$ value indicates that the translational state is less affected. A smaller $\Delta PS$ value indicates that the translation is more significantly inhibited.

FIG. 5 shows a $\Delta PS$ histogram of 19,099 types of mRNA. $\Delta PS$ is an index that indicates heat stress-induced changes in the state of polysome formation. The ordinate shows the number of genes.

Based on the results of the polysome/microarray analysis, 17 genes were selected at every given value so as to contain high-ranking to low-ranking genes in the $\Delta PS$ ranking. At this time, only the genes whose total length of the 5' UTR has been identified were selected based on the information provided by Kawaguchi et al. (NPL 4).

FIG. 7A shows a $\Delta PS$ histogram showing the $\Delta PS$ values of the 17 selected genes with circles.

Further, 22 high-ranking genes whose translational state is predicted to be free from repression even under heat stress were selected. FIG. 8A shows a $\Delta PS$ histogram showing the APS values of the 22 genes with circles.

The total of 39 genes of the 17 and 22 selected genes were used for the test.

3-2 Influence on the Translation of Capped mRNA by the 5' UTR Derived from the 39 Selected Genes In order to examine the contribution of the 5' UTRs of the 39 selected genes to the translation under heat stress, in vitro synthesized reporter mRNA containing the 5' UTR to be tested was introduced into protoplasts, and a transient expression experiment for evaluating the expression of the reporter was performed.

Figure 6:
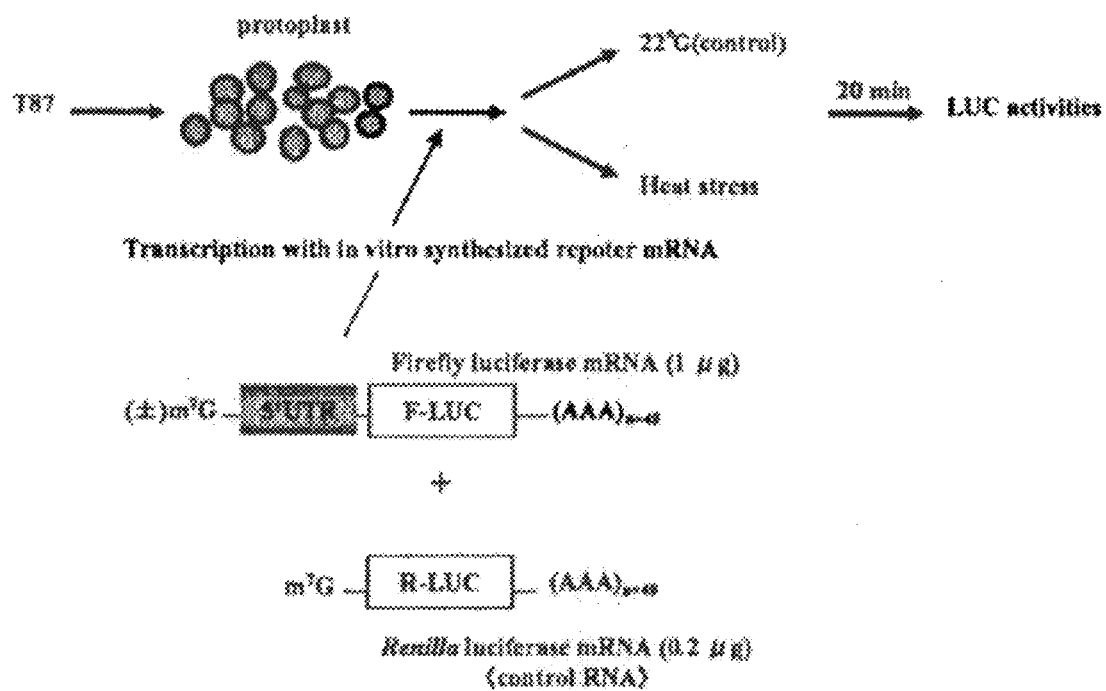
FIG. 6 summarizes a protoplast transient expression experiment. in vitro synthesized firefly luciferase (f-luc) mRNA and *Renilla luciferase* (r-luc) mRNA are introduced into protoplasts prepared from *Arabidopsis thaliana* cultured cells (T87) by PEG method. Subsequently, the protoplasts are divided and are allowed to stand under normal temperature (22° C.) or heat stress for 20 minutes. Thereafter, the protoplasts are collected, and luciferase activity (LUC activity) is measured. $m^7G$ indicates the cap structure, and "n=49" indicates the length of a poly-A sequence.

FIG. 6 summarizes a transient expression experiment. in vitro synthesized firefly luciferase (f-luc) mRNA and *Renilla luciferase* (r-luc) mRNA were introduced by PEG method into protoplasts prepared from *Arabidopsis thaliana* cultured cells (T87), and subsequently, the protoplasts were divided into two samples. Protoplast sample 1 was allowed to stand under normal temperature (22° C.) for 20 minutes and protoplast sample 2 was allowed to stand under heat stress for 20 minutes. Subsequently, both protoplast samples were collected, and the f-luc and r-luc activities were measured. m$^7$G indicates the cap structure, and n=49 indicates the length of a poly-A sequence.

Each firefly luciferase mRNA (f-luc mRNA) has a cap structure to which the 5' UTR of each gene is individually connected, contains a poly-A sequence, and is also expressed as +cap__5' UTR_f-luc_pA mRNA. Further, *renilla luciferase* (r-luc) mRNA is a control RNA having a cap structure and poly-A sequence, and is also expressed as +cap_r-luc_pA mRNA.

FIG. 7B shows the result of the test of the 17 genes selected at every given value from the higher to lower ranking genes in the ΔPS ranking. Equal amounts of +cap__5' UTR_f-luc_pA mRNAs to which the 5' UTRs of the selected genes have been individually connected were separately introduced into protoplasts with +cap_r-luc_pA mRNA as a control. The protoplasts transfected with the mRNA were divided into two samples. Subsequently, one sample was allowed to stand under normal temperature (22° C.) for 20 minutes and the other sample under heat stress (37° C.) for 20 minutes. Then, protoplasts were collected from each sample, and the f-luc and r-luc activities were measured. The ordinate shows the AGI code of each selected gene with a ΔPS value in the parentheses. The abscissa shows the relative f-luc activity level (a) or r-luc activity level (b) when the activity level of each construct at 22° C. was assumed to be 1. The results are averages and standard errors from three independent experiments.

Further, FIG. 8B shows the results of the test of the 22 genes selected mainly from the high-ranking genes. Equal amounts of +cap__5' UTR_f-luc_pA mRNAs to which the 5' UTRs of the selected genes have been individually connected were separately introduced into protoplasts with +cap_r-luc_pA mRNA as a control. The protoplasts transfected with the mRNA were divided into two samples. Subsequently, one sample was allowed to stand under normal temperature (22° C.) for 20 minutes and the other sample under heat stress (37° C.) for 20 minutes. Then, protoplasts were collected from each sample, and the f-luc and r-luc activities were measured. The ordinate shows the AGI code of each selected gene with a ΔPS value in the parentheses. The abscissa shows the relative f-luc activity level (a) or r-luc activity level (b) when the activity level of each construct at 22° C. was assumed to be 1. The results are averages and standard errors from three independent experiments.

As shown in data of At3g47610, At3g51860, At5g39740, and the like in FIG. 7B-(a), the relative activity level was reduced by heat stress treatment at 37° C. when the 5' UTRs of the middle-ranking or lower-ranking genes were used.

On the other hand, as shown in data of At4g14560 in FIG. 7B-(a), and At1g55330, At1g77120 and the like in FIG. 8B-(a), such a decrease in the relative activity level was not observed in the case of the 5' UTRs of higher-ranking genes.

In contrast, as shown in FIGS. 7B-(b) and 8B-(b), the expression level of +cap_r-luc_pA mRNA used for co-transfection as a control was uniformly reduced by heat stress treatment regardless of the type of +cap__5' UTR_f-luc_pA mRNA.

Figure 7:
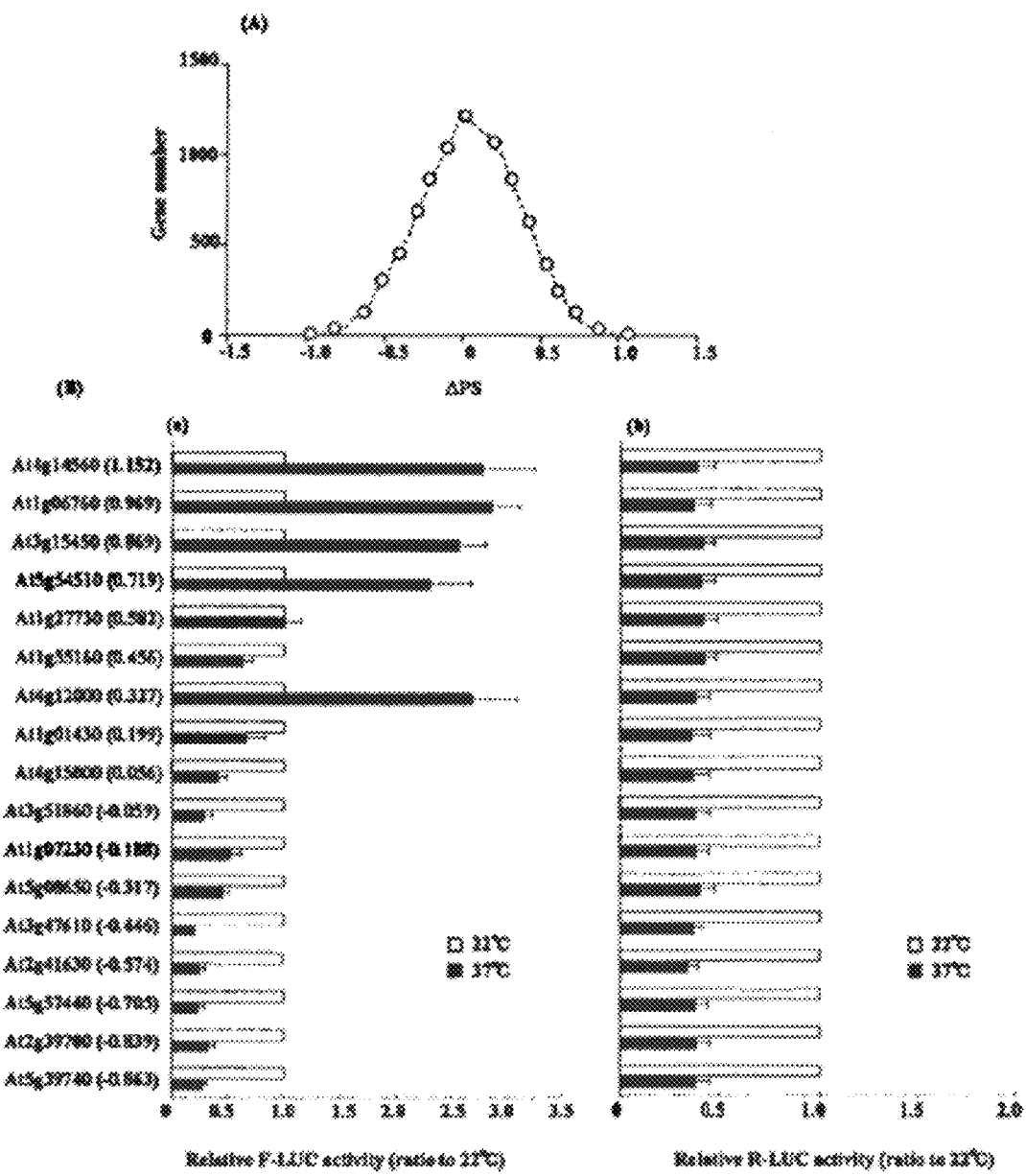
FIG. 7A shows a ΔPS histogram (n=19099) on which the ΔPS values of 17 genes selected on a certain ΔPS value basis are indicated by a circle. For FIG. 7B, equal amounts of +cap__5' UTR_f-luc_pA mRNAs to which the 5' UTRs of the selected genes have been individually connected are separately introduced into protoplasts with +cap_r-luc_pA mRNA as a control. The protoplasts transfected with the mRNA are divided, and then allowed to stand under normal temperature (22° C.) or heat stress (37° C.) for 20 minutes. Then, the protoplasts are collected, and the f-luc and r-luc activities are measured.
FIG. 7B shows the results thereof. The ordinate shows the AGI code of each selected gene with a ΔPS value in the parentheses. The abscissa shows the relative activity value when the activity level of each construct at 22° C. is assumed to be 1. (a) is the relative f-luc activity level, and (b) is the relative r-luc activity level. The values are expressed as averages and standard errors from three independent experiments.
Figure 8:
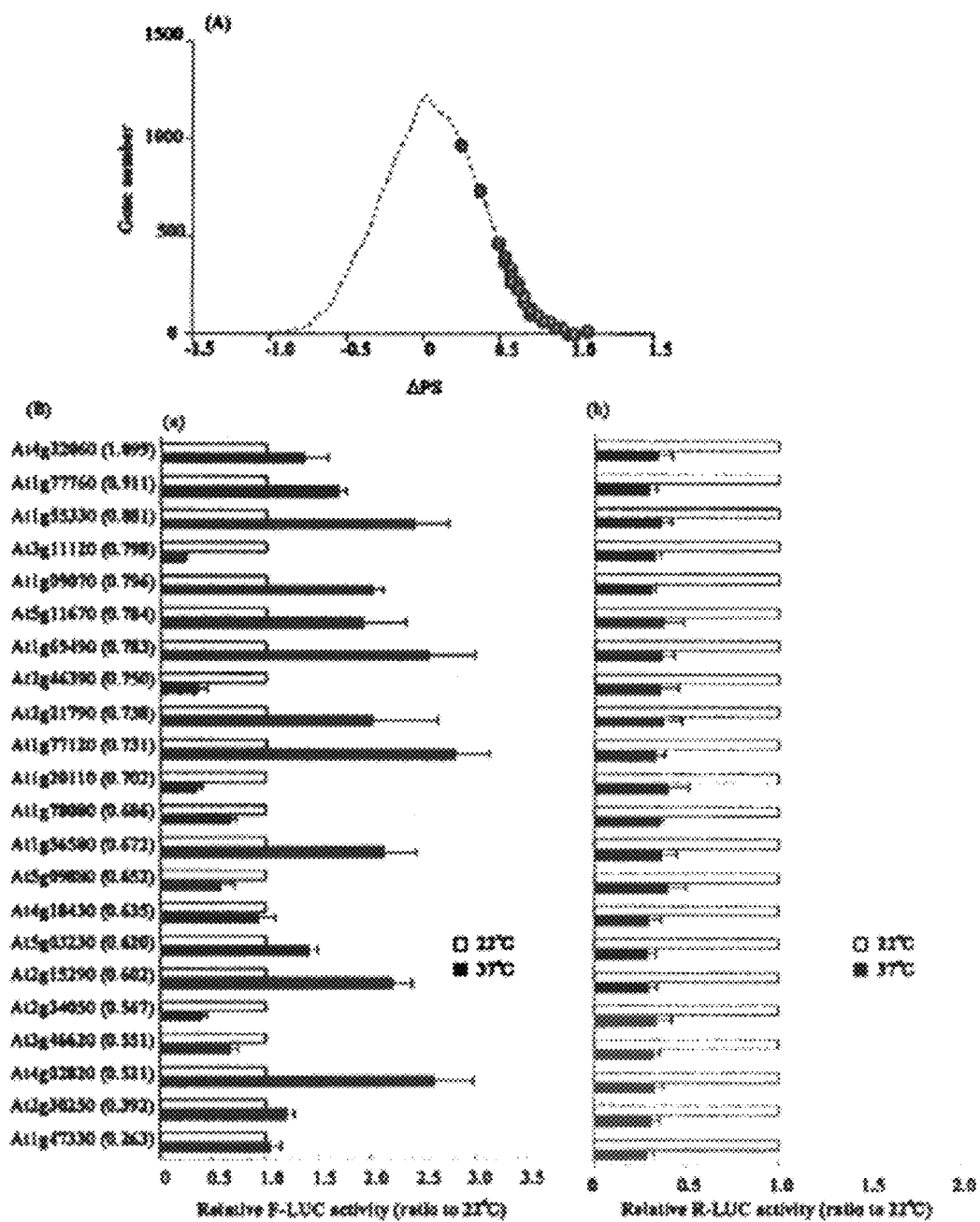
FIG. 8A shows a ΔPS histogram on which the ΔPS values of 22 genes selected mainly from the higher-ranking genes are indicated by a circle. For FIG. 8B, equal amounts of +cap__5' UTR_f-luc_pA mRNAs to which the 5' UTRs of the selected genes have been individually connected are separately introduced into protoplasts with +cap_r-luc_pA mRNA as a control. The protoplasts transfected with the mRNA are divided, and then allowed to stand under normal temperature (22° C.) or heat stress (37° C.) for 20 minutes. Then, the protoplasts are collected, and the f-luc and r-luc activities are measured.
FIG. 8B shows the results thereof. The ordinate shows the AGI code of each selected gene with a ΔPS value in the parentheses. The abscissa shows the relative activity value when the activity level of each construct at 22° C. is assumed to be 1. (a) is the relative f-luc activity level, and (b) is the relative r-luc activity level. The values are expressed as averages and standard errors from three independent experiments.
Figure 9:
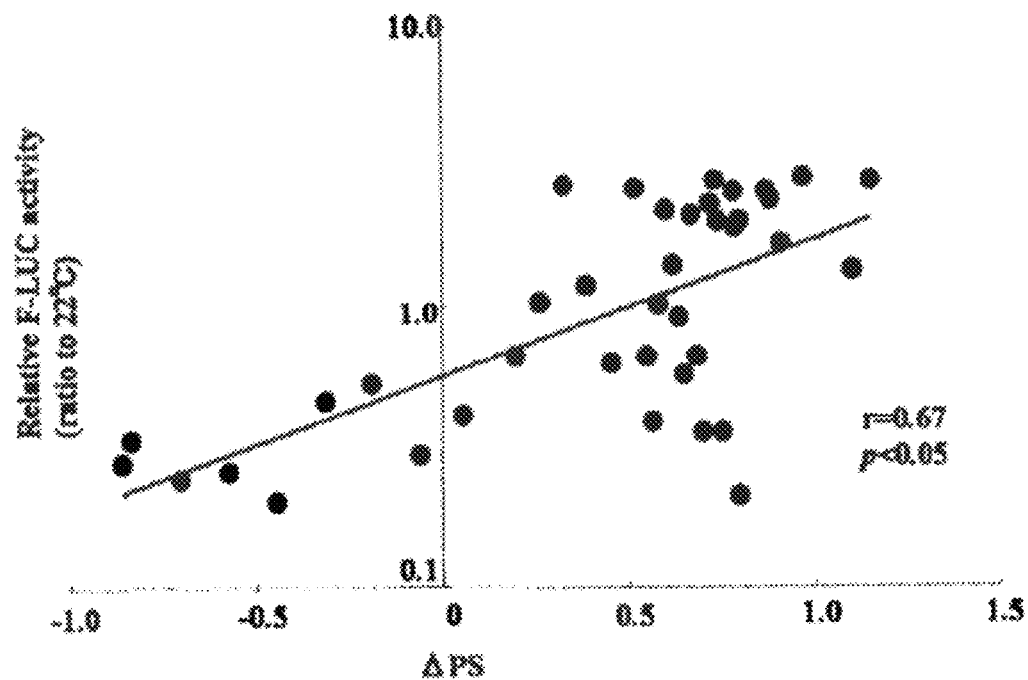
FIG. 9 shows the correlation between the relative activity level at 37° C. with respect to that at 22° C. and the ΔPS value, which are shown in FIGS. 7 and 8, for the total of 39 genes tested. The ordinate shows the logarithm, and r indicates the Pearson correlation coefficient. The presence or absence of the correlation is statistically tested (p).

Further, FIG. 9 shows the correlation between the relative activity level at 37° C. with respect to that at 22° C. and the ΔPS value, which are shown in FIGS. 7 and 8, for the total of 39 genes tested. The ordinate shows the logarithm, and r indicates the Pearson correlation coefficient. The presence or absence of the correlation was statistically tested (p).

As shown in FIG. 9, a positive correlation was observed between the relative activity level at 37° C. with respect to that at 22° C. and the ΔPS value, which were obtained for the 5' UTRs of the 39 genes (r=0.67, p<0.05).

The results show the importance of the 5' UTR as a factor that determines the translational state under heat stress.

4. In Silico Analysis Using PLS to Extract Sequence Information of the 5' UTR That Regulates the Translational Control in Response to Heat Stress, and Examination Thereof The above section 3 showed that the 5' UTR is an important factor that determines the response to heat stress at the mRNA translational level.

Consequently, further, an attempt was made to extract information on the sequences in the 5' UTR, which is related to the translational state under heat stress, by in silico analysis using PLS analysis based on the base position from the 5' side.

4-1 Construction of a Prediction Model Using PLS, Which Associates the Response at the Translational level with 5' UTR Sequence Information Based on the 5' UTR sequence information and the information of the relative activity level at 37° C. with respect to that at 22° C. of the total of 39 genes used for the transient expression experiment described previously, a regression model was constructed by multivariate analysis (PLS) that determines a coefficient of the variable (partial base sequence) with respect to the actual relative activity level. FIG. 10 shows a conceptual diagram.

First, the relative activity level at 37° C. with respect to that at 22° C. (relative activity level) of the 5' UTRs of the 39 genes tested in the above section 3 was extracted, and sequence information of each 5' UTR was extracted (FIG. 10A).

Next, a sequence of length of L was taken out from a given position k in the 5' UTR (for example, 10 bases from the 5' end or 20 bases from base 10) (FIG. 10B). The frequency of a partial sequence comprising 3 bases (for example, AAA, AUG, UUC, and the like) contained in the extracted region was counted (FIG. 10C). A regression model was constructed for the specified region using PLS, and regression coefficients for the sequences comprising 3 bases were obtained (FIG. 10D).

Then, regression models and regression coefficients for various regions were calculated, and $Q^2$ was determined as a measure of the prediction accuracy of a model for the actual relative activity level.

Figure 11:
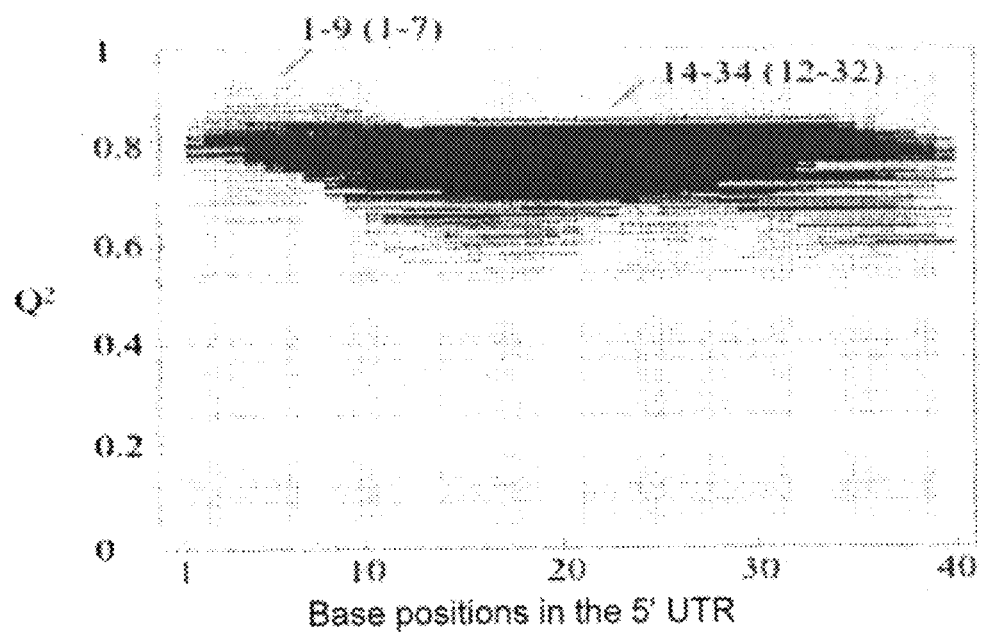
FIG. 11 shows regions that affect translation in the 5' UTR under heat stress, which are determined by in silico analysis using the sequence information on the 5' UTRs of the 39 genes used in the test and the relative activity level obtained by a transient expression experiment. The abscissa shows the distance (or base positions) from the 5' end, within the 5' UTR. 1 to 9 (1 to 7) indicate the $1^{st}$ to $9^{th}$ bases from the 5' end (the actual region of the 5' UTR consists of the $1^{st}$ to $7^{th}$ bases, which is determined by subtracting 2 from the value of the above-described region). 14 to 34 (12 to 32) indicate the $14^{th}$ to $34^{th}$ bases from the 5' end (the actual region of the 5' UTR consists of the $12^{nd}$ to $34^{th}$ bases and is determined by subtracting 2 from the values of the above-described region). The ordinate shows the $Q^2$ value obtained by in silico analysis, which indicates the prediction accuracy. A region with a higher $Q^2$ value exhibits higher prediction accuracy, and the constructed model can be explained based on that region alone. Specifically, this indicates that the region directly influences the selective translation of the reporter mRNA under heat stress. Each mRNA used in the transient expression experiment contains GG added to the 5' end after transcription from the promoter, and a sequence containing these (GG+5' UTR sequence) is used for in silico analysis. Accordingly, the actual 5' UTR region is obtained by subtracting 2 from the value of the region.

FIG. 11 shows the analysis results of the regions that influence the translation in the 5' UTR under heat stress, which were determined by in silico analysis using the 5' UTR sequence information of the 39 genes used in the test and the relative activity level obtained from the transient expression experiment.

The abscissa in FIG. 11 shows the distance from the 5' end, within the 5' UTR. The ordinate shows $Q^2$ values that indicate the prediction accuracy, which were obtained by in silico analysis. A region with a higher $Q^2$ value has a higher prediction accuracy, and it is possible to explain the constructed model based on that region alone. Specifically, this indicates that the region directly influences the selective translation of the reporter mRNA under heat stress. Each mRNA used in the transient expression experiment contains GG added at the 5' end after transcription from the promoter, and a sequence comprising that (GG+5' UTR sequence) was used for in silico analysis. Accordingly, the actual 5' UTR region is obtained by subtracting 2 from the value of the region.

The results show that $Q^2$ greatly differs depending on the region used for the model construction, and it was inferred that 9 bases at the 5' end having the highest $Q^2$, i.e., 7 bases excluding GG derived from the T3 promoter in the actual 5' UTR, are very important.

Figure 12:
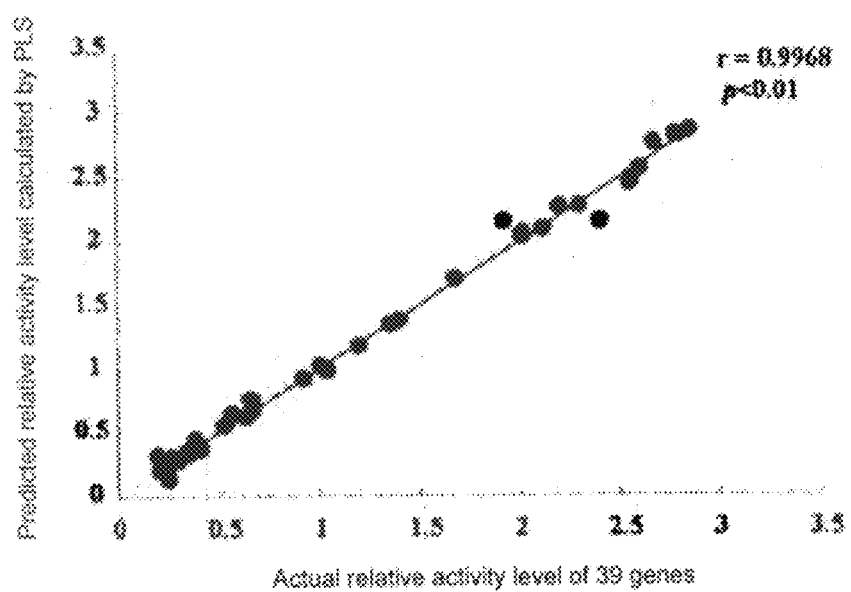
FIG. 12 shows the correlation between the relative activity level predicted by PLS method based on bases 1 to 7, and the actual relative activity level. The ordinate shows the relative activity level predicted by PLS from the regression model based on the 9 bases (actually, 7 bases) at the 5' end, and the abscissa shows the actual relative activity level of the 39 genes. Herein, r indicates the Pearson correlation coefficient, and p<0.01 shows the results from the test for non-correlation.

In regard to the 9 bases at the 5' (actually 7 bases) having the highest $Q^2$ value, FIG. 12 shows the correlation between the predicted value of the relative activity level obtained from the regression model and the regression coefficients based on the region, and the actual relative activity level of the 39 genes that were actually tested. Herein, r indicates the Pearson correlation coefficient, and p<0.01 shows the results from the test for non-correlation.

As a result, a very high correlation was observed, and a model with high accuracy is considered to have been constructed.

4-2 7 Bases at the 5' End of the 5' UTR Play a Very Important Role in the Escape from Translational Repression under Heat Stress The importance of 7 bases at the 5' end of the 5' UTR predicted by in silico analysis, i.e., the 7 bases excluding GG derived from the T3 promoter from the 9 bases predicted by in silico analysis, was examined in a transient expression experiment.

Among the 5' UTRs of the 39 genes used in the transient expression experiment, 7 bases at the end 5' of the genes (At4g14560, At3g15450, and At1g77120) whose relative activity level at 37° C. with respect to that at 22° C. was high were replaced by 7 bases at the end 5' of the genes (At3g47610 and At5g57440) with a low relative activity level. Then, the reporter activity at 22° C. and 37° C. was measured in the same manner as in the previous transient expression experiment.

In regard to the 5' UTRs of the genes with a high relative activity level, At4g14560 was shown as good (1), At3g15450 was shown as good (2), and At1g77120 was shown as good (3). In contrast, in regard to the 5' UTRs of the genes with a low relative activity level, At3g47610 was shown as bad (1), and At5g57440 was shown as bad (2).

Figure 13:
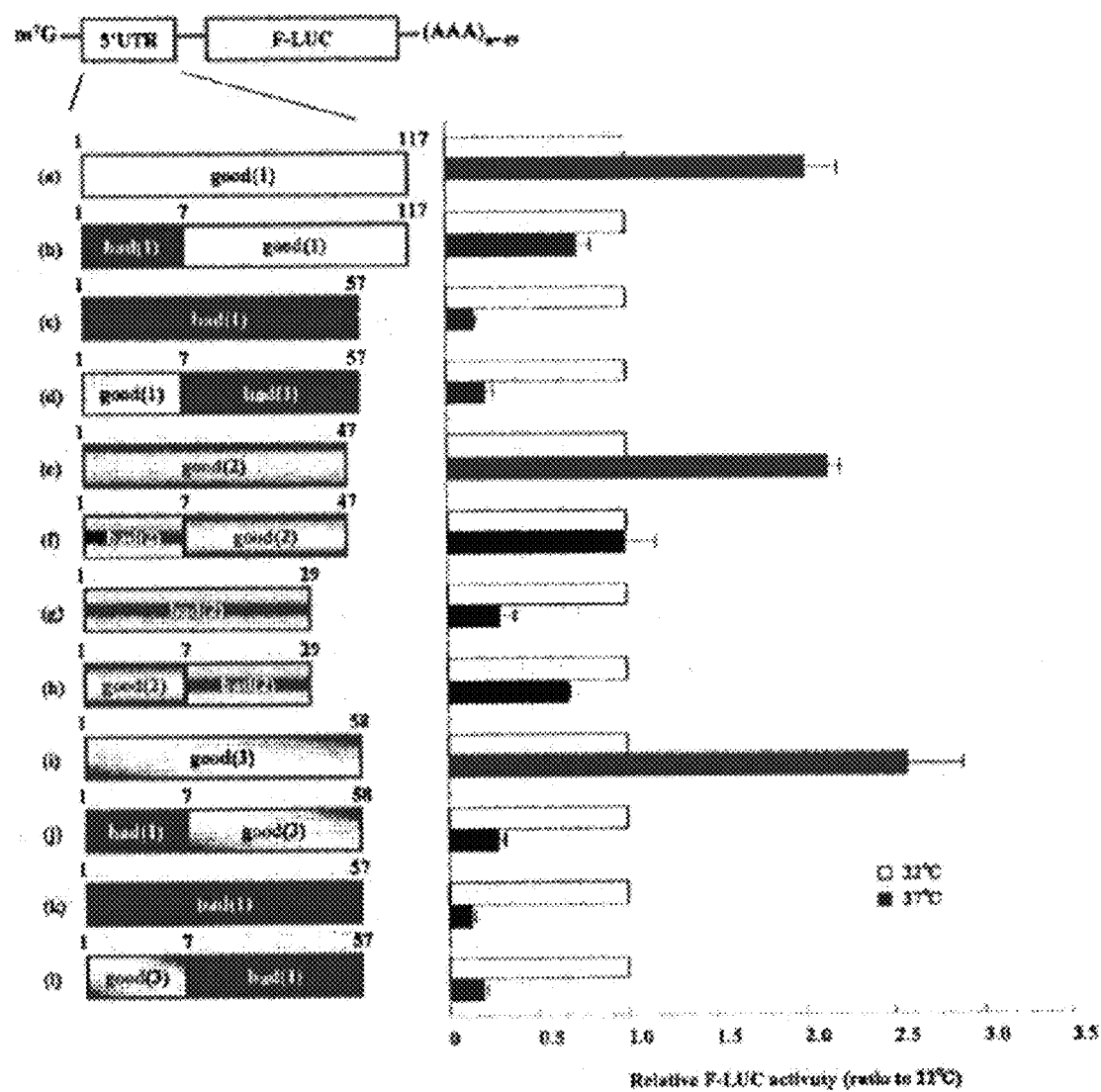
FIG. 13 shows the influence of 7 bases at the 5' end of the 5' UTR on reporter mRNA translation under heat stress. The examination is carried out to investigate the influence on reporter mRNA translation by the replacement of 7 bases at the 5' end between the 5' UTR with a high relative activity level (good (1): At4g14560; good (2): At3g15450; good (3): At1g77120, black characters) and the 5' UTR with a low relative activity level (bad (1): At3g47610; bad (2): At5g57440, white characters). (a), (c), (e), (g), (i), and (k) each show mRNA of the full length 5' UTR. In (b), (d), (f), (h), (j), and (l), bases 1 to 7 in these 5' UTRs are replaced by the bases in the 5' UTRs shown in the figure. Further, for the right side of the figure, +cap_5' UTR_f-luc_pA mRNAs to which the 5' UTRs shown in the figure have been individually added are separately introduced into protoplasts with +cap_r-luc_pA mRNA as a control. The protoplasts transfected with the mRNA are divided, and then allowed to stand under normal temperature (22° C.) or heat stress (37° C.) for 20 minutes. The protoplasts are then collected, and the f-luc and r-luc activities are measured. The right side of the figure shows the f-luc activity level when the activity level at 22° C. is assumed to be 1. The values are expressed as averages and standard errors from three independent experiments.

The left side in FIG. 13 shows the total length of the 5' UTR of the genes used and the structures obtained by replacing bases 1 to 7 in the 5' UTR by bases 1 to 7 of a different 5' UTR.

(a), (c), (e), (g), (i), and (k) show the total length of the 5' UTRs of the genes used. (b), (d), (f), (h), (j), and (l) show constructs obtained by replacing bases 1 to 7 in the 5' UTRs of these genes by the 5' UTR shown in the figure.

Further, Table 2 shows the AGI codes, sequences, and the total number of nucleotides in the 5' UTRs (a) to (l) used for the analysis in FIG. 13. The bold and underlined portions are sequences of 7 bases at the 5' end after replacement.

+cap__5' UTR_f-luc_pA mRNA to which (a) to (l) have been individually added were separately introduced into protoplasts with +cap_r-luc_pA mRNA as a control. The protoplasts transfected with the mRNA were divided into two samples. Subsequently, one sample was allowed to stand under normal temperature (22° C.) for 20 minutes and the other sample under heat stress (37° C.) for 20 minutes. Then, protoplasts were collected from each sample, and the f-luc and r-luc activities were measured.

The right side in FIG. 13 shows the f-luc activity level of each construct when the activity level at 22° C. was assumed to be 1. The results are averages and standard errors from three independent experiments.

Regardless of the type of +cap__5' UTR_f-luc_pA mRNA tested, the expression from +cap_r-luc_pA mRNA was reduced by a similar amount.

As shown in the comparison between (a) and (b), (e) and (f), and (i) and (j) in FIG. 13, when 7 bases at the 5' end of the 5' UTR with a high relative activity level were replaced by 7 bases at the 5' end of the 5' UTR with a low relative activity level, a decrease in the relative activity level was observed in every 5' UTR.

On the other hand, as shown in the comparison between (c) and (d), (g) and (h), and (k) and (l) in FIG. 13, when 7 bases at the 5' end of the 5' UTR of a gene with a low relative activity level were replaced by 7 bases at the 5' end of the 5' UTR of a gene with a high relative activity level, although no significant changes were observed, a slight increase in the relative activity level was recognized. However, in regard to (l), because a new initiation codon AUG would be created as a result of the replacement by 7 bases at the 5' end of the 5' UTR of a gene with a high relative activity level (see the sequence (l) in Table 2), it is not considered to reflect the true reporter activity.

These results indicate that 7 bases at the 5' end of the 5' UTR greatly influence the selective translation induced by heat stress.

However, the increase in the relative activity level was small when 7 bases at the 5' end of the 5' UTR with a low relative activity level were replaced by 7 bases at the 5' end of the 5' UTR with a high relative activity level. This suggested the presence of another region in the 5' UTR other than 7 bases at the 5' end, which is important to the escape from translational repression.

TABLE 2

| Sample name | AGI code | Sequence | 5'UTR (nt) |
|---|---|---|---|
| a | At4g14560 | (SEQ ID NO: 16)<br>acacaagcauuuucaaggauaucaaaucacaaucccaagaagagcaauaacaa gagaagaagaaguaguucaagaauuaaggaagagagcuucuccguuaaaguau agugagagaau | 117 |
| b | — | (SEQ ID NO: 17)<br><u>ccuuucu</u>cauuuucaaggauaucaaaucacaaucccaagaagagcaauaacaagagaaga agaaguaguucaagaauuaaggaagagagcuucuccguuaaaguauagugagagaau | 117 |
| c | At3g47610 | (SEQ ID NO: 18)<br>ccuuucuugucgucguuucgaagagacuaaaggcgacggagaguucggaguagaug | 57 |
| d | — | (SEQ ID NO: 19)<br><u>acacaag</u>ugucgucguuucgaagagacuaaaggcgacggagagaaucggagaagaag | 57 |
| e | At3g15450 | (SEQ ID NO: 20)<br>auaacacauuucaagcauuggauuaaucaaagacaaagaaaacqaaa | 47 |

TABLE 2-continued

| Sample name | AGI code | Sequence | 5'UTR (nt) |
|---|---|---|---|
| f | — | gguucguauuucaagcauuggauuaaucaaagacaaagaaaacgaaa (SEQ ID NO: 21) | 47 |
| g | At5g57440 | gguucgucguuaucgguaucgaaucaaca (SEQ ID NO: 22) | 29 |
| h | — | auaacaccguuaucgguaucgaaucaaca (SEQ ID NO: 23) | 29 |
| i | At1g77120 | uacaucacaaucacacaaaacuaacaaaagaucaaaagcaaguucuucacuguugaua (SEQ ID NO: 24) | 88 |
| j | — | ccuuucucaaucacacaaaacuaacaaaagaucaaaagcaaguucuucacuguugaua (SEQ ID NO: 25) | 88 |
| k | At3g47610 | ccuuucuugucgucguuucgaagagacuaaaggcgacggagagaaucggagaagaag (SEQ ID NO: 26) | 57 |
| l | — | uacaucaugucgucguuucgaagagacuaaaggcgacggagagaaucggagaagaag (SEQ ID NO: 27) | 57 |

5' UTRs Used for the Analysis in FIG. 13, and the Sequence Information of the 5' UTRs after Replacement

4-3 Bases 12 to 32 in the 5' UTR Also Contribute to the Escape from Translational Repression under Heat Stress Section 4-2 suggested a possibility of a region other than the region of 7 bases at the 5' end of the 5' UTR, which contributes to the escape from heat stress-induced translational repression.

Based on the above-described model constructed using PLS and $Q^2$ analysis shown in FIG. 11, the base region form positions 12 to 32, i.e., the region excluding GG derived from the T3 promoter from bases 14 to 34 predicted by in silico analysis, was presumed to be a possible region that contributes to the escape from heat stress-induced translational repression, other than 7 bases at the 5' end of the 5' UTR.

Consequently, in regard to bases 12 to 32 with the second-highest $Q^2$ value, the correlation was examined between the predicted value of the relative activity level obtained from the regression model and the regression coefficient based on that region, and the actual relative activity level of the 39 genes that were actually tested.

Figure 14:
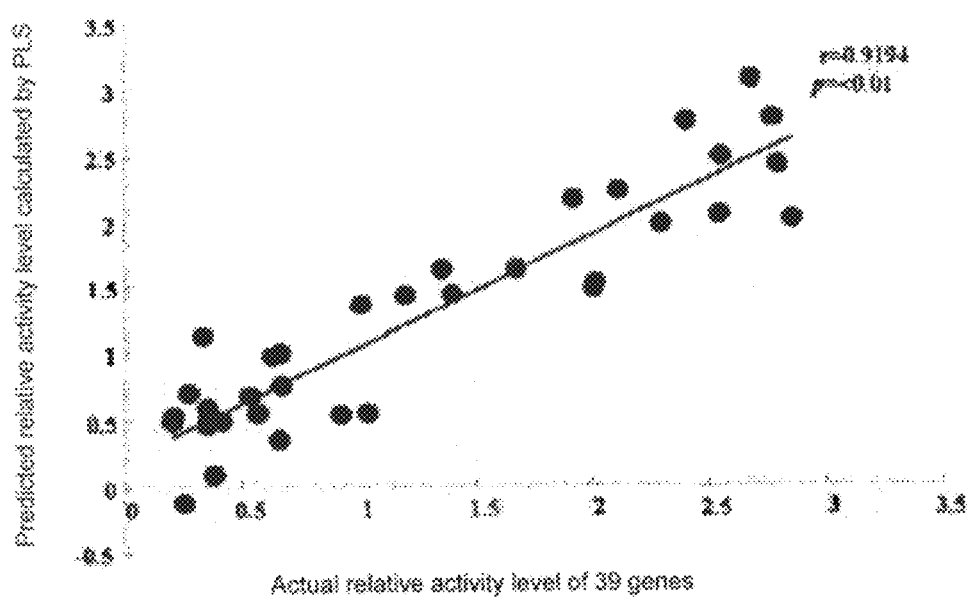
FIG. 14 shows the correlation between the relative activity level predicted from a regression model constructed by PLS based on bases 12 to 32, and the actual relative activity level. The ordinate shows the relative activity level predicted by PLS method from the regression model based on bases 12 to 32, and the abscissa shows the actual relative activity level of the 39 genes. Herein, r indicates the Pearson correlation coefficient, and p<0.01 shows the results from the test for non-correlation.

FIG. 14 shows the results. The ordinate in FIG. 14 shows the relative activity level predicted from the regression model created based on bases 12 to 32 by PLS. The abscissa shows the actual relative activity levels of the 39 genes. Herein, r indicates the Pearson correlation coefficient, and $p<0.01$ shows the results from the test for non-correlation.

As a result, a high correlation was indeed observed, although it was lower compared to the results of bases 1 to 7 at the 5' end shown in FIG. 12. It is presumed to be possible to construct a model with high accuracy also from this region.

Consequently, bases 12 to 32 were also evaluated by a transient expression experiment in a similar manner as 7 bases at the 5 end described above.

Herein, in order to eliminate the influence by the difference in the total number of nucleotides in the 5' UTR, genes whose 5' UTR lengths are as similar to each other as possible were selected as a pair of genes to be replaced, and the replacement was performed between genes (47 nt and 42 nt) of a short pair and between genes (210 nt and 198 nt) of a long pair.

Figure 15:
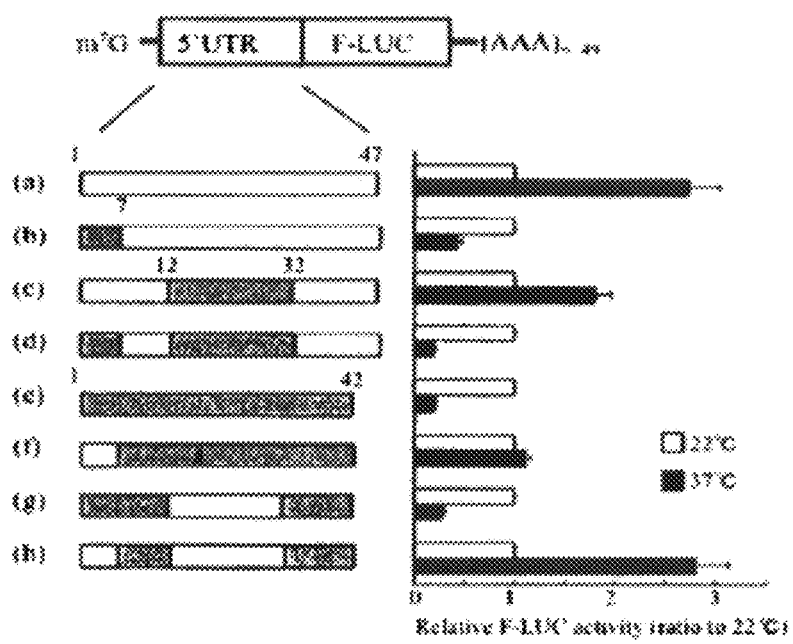
FIG. 15 shows the results from the examination of the influence of 7 bases and bases 12 to 32 at the 5' end of the 5' UTR on reporter mRNA translation under heat stress, by the replacement in a pair of short bases (47 bp and 42 bp). The examination is carried out to investigate the influence on reporter mRNA translation by the replacement of 7 bases and/or bases 12 to 32 at the 5' end between the 5' UTR (At3g15450) with a high relative activity level and the 5' UTR (At5g39740) with a low relative activity level. (a) and (e) each show the full length? sequence of the 5' UTR. (b), (c), (d), (f), (g), and (h) show constructs obtained by replacing the base regions (indicated by the number) in the 5' UTR between (a) and (e). Further, for the right side of the figure, +cap_5' UTR_f-luc_pA mRNAs to which the 5' UTRs shown in the figure have been individually added are separately introduced into protoplasts with +cap_r-luc_pA mRNA as a control. The protoplasts transfected with the mRNA are divided, and then allowed to stand under normal temperature (22° C.) or heat stress (37° C.) for 20 minutes. The protoplasts are then collected, and the f-luc and r-luc activities are measured. The right side of the figure shows the f-luc activity level when the activity level at 22° C. is assumed to be 1. The values are expressed as averages and standard errors from three independent experiments.

FIG. 15 shows the results of the replacement test of the short pair.

FIG. 15 shows the examination of the influence on reporter mRNA translation by the replacement of 7 bases and/or bases 12 to 32 at the 5' end between the 5' UTR (white box) of gene At3g15450 with a high relative activity level and the 5' UTR (gray box) of gene At5g39740 with a low relative activity level.

In FIG. 15, (a) and (e) each show the full length sequence of the 5' UTR. (b), (c), (d), (f), (g), and (h) show constructs obtained by replacing the base regions (indicated by the number) in the 5' UTR between (a) and (e).

Further, Table 3 shows the AGI codes, sequences, and the total number of nucleotides in the 5' UTRs (a) to (h) used for the analysis in FIG. 15. The bold and underlined portions are sequences of 7 bases and/or bases 12 to 32 at the 5' end after replacement.

+cap__5' UTR_f-luc_pA mRNAs to which the 5' UTRs shown in (a) to (h) have been individually added were separately introduced into protoplasts with +cap_r-luc_pA mRNA as a control. The protoplasts transfected with the mRNA were divided into two samples. Subsequently, one sample was allowed to stand under normal temperature (22° C.) for 20 minutes and the other sample under heat stress (37° C.) for 20 minutes. Then, protoplasts were collected from each sample, and the f-luc and r-luc activities were measured.

The right side in FIG. 15 shows the f-luc activity level of each construct when the activity level at 22° C. was assumed to be 1. The results are averages and standard errors from three independent experiments. Regardless of the type of +cap__5' UTR_f-luc_pA mRNA tested, the expression from +cap_r-luc pA mRNA was reduced by a similar amount.

TABLE 3

| Sample name | AGI code | Sequence | 5'UTR (nt) |
|---|---|---|---|
| a | At3G15450 | (SEQ ID NO: 28)<br>auaacacauuucaagcauuggauuaaucaaagacaaagaaaacgaaa | 47 |
| b | — | (SEQ ID NO: 29)<br>gguucguauuucaagcauuggauuaacaaagacaaagaaaacgaaa | 47 |
| c | — | (SEQ ID NO: 30)<br>auaacacauuucaucuggugucacucaucuugacaaagaaaacgaaa | 47 |
| d | — | (SEQ ID NO: 31)<br>gcgccucauuucaucuuuugucacucaucuugacaaagaaaacgaaa | 47 |
| e | At5g39740 | (SEQ ID NO: 32)<br>gcgccucuugccaucuuuugucacucaucuucacaggaaaca | 42 |
| f | — | (SEQ ID NO: 33)<br>auaacacuugccaucuuuugucacucaucuucacaggaaaca | 42 |
| g | — | (SEQ ID NO: 34)<br>gcgccucuugccaggcauuggauuaaucaaagacagaaaaca | 42 |
| h | — | (SEQ ID NO: 35)<br>auaacacuugcgaagcauuggauuaaucaaugacagaaaca | 42 |

5' UTRs Used for the Analysis in FIG. 15, and the Sequence Information of the 5' UTRs after Replacement In the case of a short pair, the activity level was reduced by the replacement of 7 bases at the 5' end of the 5' UTR (white box) with a high relative activity level by 7 bases at the 5' end of the 5' UTR (gray box) with a low relative activity level (FIG. 15-b). Further, a decrease was observed when bases 12 to 32 from the 5' end were replaced, although not as much as when 7 bases at the 5' end were replaced (FIG. 15-c).

When both regions were simultaneously replaced, the activity level was more significantly reduced compared to when only 7 bases were replaced (FIG. 15-d). In contrast, an increase in the relative activity level was observed when 7 bases at the 5' end of the 5' UTR (gray box) with a low relative activity level were replaced by 7 bases at the 5' end of the 5' UTR (white box) with a high relative activity level (FIG. 15-f). An increase was observed also when bases 12 to 32 were replaced, although not as high as when 7 bases were replaced (FIG. 15-g). When both regions were simultaneously replaced, the activity level was more significantly increased compared to when only 7 bases were replaced (FIG. 15-h). When looking at (a) and (h) or (d) and (e) in FIG. 15, (d) and (h) can be hypothetically considered to be obtained by replacing regions other than 7 bases and bases 12 to 32 at the 5' end in (e) and (a), respectively, by other regions, and it is suggested that the regions other than 7 bases and bases 12 to 32 at the 5' end have almost no influence on the relative activity level.

The above results indicate that 7 bases at the 5' end are important to reporter mRNA translation under heat stress, and that although the influence by the region of bases 12 to 32 is less, the presence thereof together with 7 bases at the 5' end provides greater influence.

Figure 16:
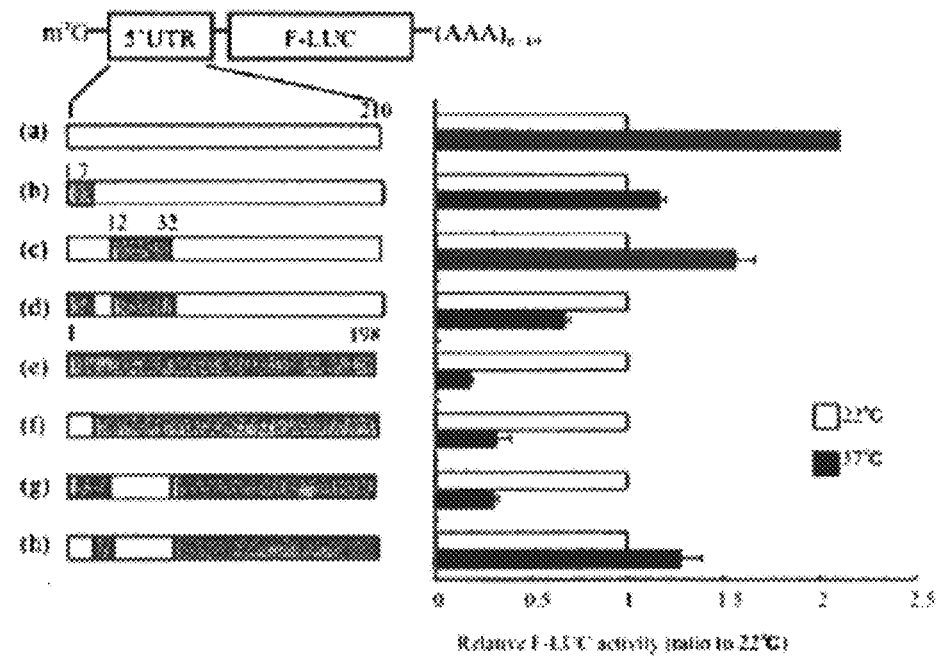
FIG. 16 shows the results from the examination of the influence of 7 bases and bases 12 to 32 at the 5' end of the 5' UTR on reporter mRNA translation under heat stress by the replacement in a pair of long bases (210 bp and 198 bp). The examination is carried out to investigate the influence on the expression of reporter mRNA by the replacement of 7 bases and/or bases 12 to 32 at the 5' end between the 5' UTR (At4g12000) with a high relative activity level and the 5' UTR (At2g41630) with a low relative activity level. (a) and (e) each show the full length sequence of the 5' UTR. (b), (c), (d), (f), (g), and (h) show constructs obtained by replacing the base regions (indicated by the number) in the 5' UTR between (a) and (e). Further, for the right side of the figure, +cap_5' UTR_f-luc_pA mRNAs to which the 5' UTRs shown in the figure have been individually added, are separately introduced into protoplasts with +cap_r-luc_pA mRNA as a control. The protoplasts transfected with the mRNA are divided, and then allowed to stand under normal temperature (22° C.) or heat stress (37° C.) for 20 minutes. The protoplasts are then collected, and the f-luc and r-luc activities are measured. The right side of the figure shows the f-luc activity level when the activity level at 22° C. is assumed to be 1. The values are expressed as averages and standard errors from three independent experiments.

Further, FIG. 16 shows the results of the replacement test of the long pair.

FIG. 16 shows the examination of the influence on reporter mRNA translation by the replacement of 7 bases and/or bases 12 to 32 at the 5' end between the 5' UTR (white box) of gene At4g12000 with a high relative activity level and the 5' UTR (gray box) of gene At2g41630 with a low relative activity level.

(a) and (e) each show the full length sequence of the 5' UTR. (b), (c), (d), (f), (g), and (h) show constructs obtained by replacing the base regions (indicated by the number) in the 5' UTR between (a) and (e).

Further, Table 4 shows the AGI codes, sequences, and the total number of nucleotides in the 5' UTRs (a) to (h) used for the analysis in FIG. 16. The bold and underlined portions are sequences of 7 bases and/or bases 12 to 32 at the 5' end after replacement.

+cap_5' UTR_f-luc_pA mRNAs to which the 5' UTRs shown in (a) to (h) have been individually added were separately introduced into protoplasts with +cap_r-luc_pA mRNA as a control. The protoplasts transfected with the mRNA were divided into two samples. Subsequently, one sample was allowed to stand under normal temperature (22° C.) for 20 minutes and the other sample under heat stress (37° C.) for 20 minutes. Then, protoplasts were collected from each sample, and the f-luc and r-luc activities were measured.

The right side in FIG. 16 shows the f-luc activity level of each construct when the activity level at 22° C. was assumed to be 1. The results are averages and standard errors from three independent experiments. Regardless of the type of +cap_5' UTR_f-luc_pA mRNA tested, the expression from +cap_r-luc pA mRNA was reduced by a similar amount.

TABLE 4

| Sample name | AGI code | Sequence | 5'UTR (nt) |
|---|---|---|---|
| a | At1g12000 | (SEQ ID NO: 36)<br>auuaacaaacaaaccgaaaaaagaaaaaaacucaucuuucuccaaaaucacacaaauc<br>uucuuuauuuguuauucucaauccuuccuucaucccccagguuucuuucgauucguuga | 210 |

TABLE 4-continued

| Sample name | AGI code | Sequence | 5'UTR (nt) |
|---|---|---|---|
| | | gucauucaauuuuuccaucacuggguuuuucucucugaauccgaucggagaauccagu cgauuacuaaucuagcgcucucuuuuuuucuacucg | |
| | | (SEQ ID NO: 37) | |
| b | — | ccuucucaacaaaccgaaaaaagaaaaaaacucaucuuucuccaaaaucacacaaaug cuucuuuauuuguuauucucaauccuuccuucauccccagguuucuuucgauucguua gucauucaauuuuuccaucacugggguuuuucucucugaauccgaucggagaauccagu cgauuacuaaucuagcgcucucuuuuuuucuacucg | 210 |
| | | (SEQ ID NO: 38) | |
| c | — | auuaacaaacauaaguuacaucucucguguuucaucuuucuccaaaaucacacaaauc uucuuuauuuguuauucucaauccuuccuucaucccagguaucuugcgauucguugag ucauucaaucuuccaucacugggguuuuucucucugaauccgaucggagaauccaguc gauuacuaaccuagcgcucucucuuuuucuacucg | 210 |
| | | (SEQ ID NO: 39) | |
| d | — | ccuucucaacauaaguuacaucucucgugguucaucuuucuccaaaaucacacaaauc uucuuuauuuguuauucucaauccuuccuucauccccagguuucuuacgauucguuga gucauucaauuuuuccaucacugggguuuuucucucugaauccgaccggagaauccagu cgauuacuaaucuagcgcucucuuuuuuucuacucg | 210 |
| | | (SEQ ID NO: 40) | |
| e | At2g41630 | ccuucuuuacauaaguuacaucucucguguuuuguuuucuuugucuccgacuuuuuac gcgacgaagaagaagacgagagauagagagagaaguagagaaaucgaaggaaucugua accgauuuuaacaucucaauuuucagggugguugauuuuucaauuucuggguuaauuu uuuuuaggguuuucauuuggaauc | 198 |
| | | (SEQ ID NO: 41) | |
| f | — | auuaacacacauaaguuacaucucucguguuuuguuuucuuugucuccgauuuuuu cgcgacgaagaagaagacgagagauagagagagaaguagagaaaucgaaggaaucugu aaccgauuuuaagaucucaauuuuuaggguugugauuuuucaauuuaugggguuauuu uuuuuaggguuuucauuuggaauc | 198 |
| | | (SEQ ID NO: 42) | |
| g | — | ccuucuccacaaaccgaaaaagaaaaaaacuuguuuucuuugucuccgauuuuuuc gcgacgaagaagaagacgagagauagagagagaaguagagaaaucgaaggaaucugua accgauuuuaagaucucaauuuuuaggguugugauuuuucaauuucuggguuaauuu uuuuuaggguuuucauuuggaauc | 198 |
| | | (SEQ ID NO: 43) | |
| h | — | auuaacacacaaaccgaaaagacgaagaagaagacgagagauuuaagaucucaauuu uuggguuuucauuuggaaucaagaaaaaaacuuguuuucuauagagagagaaguagag aaaggguugugauuuuucaauuugucuccgauuuuuuucgcaucgaaggaaucugua accguucggguuaauuuuuuuua | 198 |

5' UTRs Used for the Analysis in FIG. 16, and the Sequence Information of the 5' UTRs after Replacement In the case of a long pair, the activity level was reduced by the replacement of 7 bases at the 5' end of the 5' UTR (white box) with a high relative activity level by 7 bases at the 5' end of the 5' UTR (gray box) with a low relative activity level (FIG. 16-*b*). Further, a decrease was observed when bases 12 to 32 from the 5' end were replaced, although not as much as when 7 bases at the 5' end were replaced (FIG. 16-*c*).

When both regions were simultaneously replaced, the activity level was more significantly reduced compared to when only 7 bases were replaced (FIG. 16-*d*). In contrast, an increase in the relative activity level was observed when 7 bases at the 5' end of the 5' UTR (gray box) with a low relative activity level were replaced by 7 bases at the 5' end of the 5' UTR (white box) with a high relative activity level (FIG. 16-*f*). An increase was observed also when bases 12 to 32 were replaced, although not as high as when 7 bases were replaced (FIG. 16-*g*). When both regions were simultaneously replaced, the activity level was more significantly increased compared to when only 7 bases were replaced (FIG. 16-*h*).

The above results indicate that 7 bases at the 5' end are important to reporter mRNA translation under heat stress, and that although the influence by the region of bases 12 to 32 is less, the presence thereof together with 7 bases at the 5' end provides greater influence.

4-4. Influence on Reporter mRNA Translation under Heat Stress by the Distance between the 5' End and 7 Bases and Bases 12 to 32 at the 5' End The above experimental results suggest that 7 bases and bases 12 to 32 at the 5' end of the 5' UTR are important factors that regulate the expression of reporter mRNA under heat stress.

Subsequently, the importance of these important regions being located in the vicinity of the 5' end, rather than simply being located in the 5' UTR, was examined.

Specifically, a transient expression experiment was performed to evaluate the influence on the relative activity level when the 5' UTR (gray box) gene At5g39740 with a low relative activity level was replaced by the 5' UTR (white box) gene At3g15450 with a high relative activity level, and further, 7 bases and bases 12 to 32 at the 5' end, which were inserted for replacement, were shifted toward the 3' end by 5 bp (i.e., the important regions were moved away from the 5' end).

Figure 17:
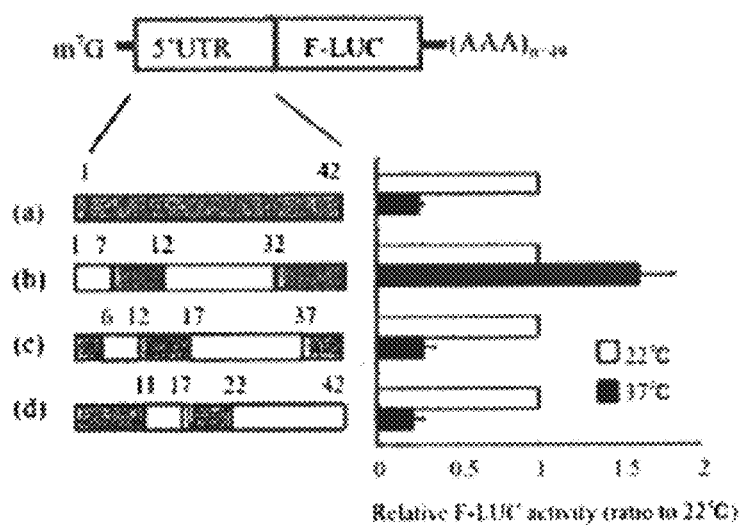
FIG. 17 shows the results from the examination of the distance between the 5' end and the regions that contribute to the escape from translational repression under heat stress. The 5' UTR (At5g39740) with a low relative activity level is replaced by the 5' UTR (At3g15450) with a high relative activity level, and the distance between the 5' end and these regions is varied. The influence on reporter mRNA translation under heat stress is examined. (a) shows the full length 5' UTR. (b), (c), and (d) show constructs obtained by replacing the regions (indicated by the number) in the 5' UTR (a) by the regions in the 5' UTRs of genes with a high relative activity level. Further, for the right side of the figure, +cap_5' UTR_f-luc_pA mRNAs to which the 5' UTRs shown in the figure have been individually added are separately introduced into protoplasts with +cap_r-luc_pA mRNA as a control. The protoplasts transfected with the mRNA are divided, and then allowed to stand under normal temperature (22° C.) or heat stress (37° C.) for 20 minutes. The protoplasts are then collected, and the f-luc and r-luc activities are measured. The right side of the figure shows the f-luc activity level when the activity level at 22° C. is assumed to be 1. The values are expressed as averages and standard errors from three independent experiments.

FIG. 17 shows the structure of the constructs. (a) shows the full length 5' UTR. (b), (c), and (d) show constructs obtained by replacing the regions (indicated by the number) in the 5' UTR (a) by the regions in the 5' UTRs of genes with a high relative activity level.

Table 5 shows the AGI codes, sequences, and the total number of nucleotides in the 5' UTRs (a) to (d) used for the analysis in FIG. 17. The bold and underlined portions are sequences of 7 bases and/or bases 12 to 32 at the 5' end after replacement.

+cap_5' UTR_f-luc_pA mRNAs to which the 5' UTRs shown in (a) to (d) have been individually added were separately introduced into protoplasts with +cap_r-luc_pA mRNA as a control. The protoplasts transfected with the mRNA were divided into two samples. Subsequently, one sample was allowed to stand under normal temperature (22° C.) for 20 minutes and the other sample under heat stress (37° C.) for 20 minutes. Then, protoplasts were collected, and the f-luc and r-luc activities were measured.

Further, the right side in FIG. 17 shows the f-luc activity level of each construct when the activity level at 22° C. was assumed to be 1. The results are averages and standard errors from three independent experiments. Regardless of the type of +cap_5' UTR_f-luc_pA mRNA tested, the expression from +cap_r-luc pA mRNA was reduced by a similar amount.

TABLE 5

| Sample name | AGI code | Sequence | 5'UTR (nt) |
|---|---|---|---|
| | | (SEQ ID NO: 44) | |
| a | At5g39740 | gcgccucuugccaucuuuugucacucau-cuucacaggaaaca | 42 |
| | | (SEQ ID NO: 45) | |
| b | — | auaacacuugc caagcauuggauuaaucaaagacaggaaaca | 42 |
| | | (SEQ ID NO: 46) | |
| c | — | gcgccduaacdcducuca agcduuggauuaaucaaagaaaca | 42 |
| | | (SEQ ID NO: 47) | |
| d | — | gcgccucuugauaacacuugu caagcauuggauuaaucaaag | 42 |

5' UTRs Used for the Analysis in FIG. 17, and the Sequence Information of the 5' UTRs after Replacement As a result, compared to the construct obtained by replacing 7 bases and bases 12 to 32 at the 5' end (FIG. 17-(*b*)), the relative activity level was significantly reduced simply by a shift toward the 3' side by 5 bp or 10 bp (FIGS. 17-(*c*) and (*d*)). The resulting relative activity level was comparable to that of the full length sequence before the replacement of the important regions.

This suggests what may be important with the important regions of 7 bases and bases 12 to 32 at the 5' end of the 5' UTR with a high relative activity level is that these regions are present on the 5' end side, rather than that these regions are simply present in the 5' UTR.

4-5. Correlation between the Activity Value Predicted Using the Model Constructed from In Silico Analysis and ΔPS In the previous experiments, a model was constructed using PLS based on the sequence information of the 5' UTR actually tested in the transient expression experiment and on the actual values thereof (relative activity level), and the important regions that contribute to reporter mRNA translation under heat stress, i.e., 7 bases and bases 12 to 32 at the 5' end, were identified.

Subsequently, the importance of 7 bases and bases 12 to 32 at the 5' end as the factors that regulate changes in the translational state in response to heat stress was examined from a different angle.

First, a regression model was again constructed by PLS using the sequence information on both 7 bases and bases 12 to 32 at the 5' end, and regression coefficients were again calculated, based on the actual values (relative activity level) of the 5' UTRs of about 39 species, which were determined by the transient expression experiment.

Subsequently, in regard to about 3,000 genes whose information on the full length 5' UTR sequence has been organized by Kawaguchi et al. (NPL 4), the relative activity level predicted from the 5' UTR sequence and the constructed model was calculated. Then, examination was performed to determine the degree of correlation between the predicted relative activity level and the ΔPS value calculated by polysome/microarray analysis described in 3-1 (i.e., an index that reflects changes in the translational state caused by heat stress).

Figure 18:
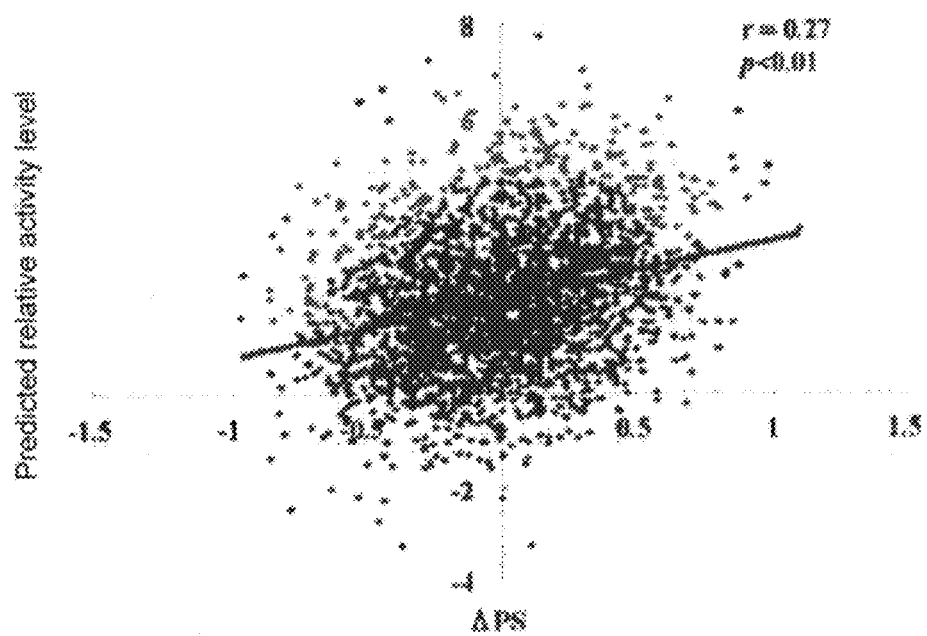
FIG. 18 shows the correlation between the relative activity level predicted from the model constructed by in silico analysis using PLS and ΔPS analyzed by polysome/microarray. The abscissa in FIG. 18 shows ΔPS obtained by polysome/microarray, and the ordinate shows the relative activity level predicted from the model constructed with in silico analysis using PLS for 1,746 genes whose 5' UTR sequence information has been organized. Herein, r indicates the Pearson correlation coefficient, and p<0.01 shows the results from the test for non-correlation.

FIG. 18 shows the results from the investigation of the correlation between the relative activity level predicted from the model constructed by in silico analysis using PLS, and ΔPS analyzed by polysome/microarray. The abscissa in FIG. 18 shows APS obtained by polysome/microarray, and the ordinate shows the relative activity level predicted from the model constructed with in silico analysis using PLS obtained in section 3-2-1 for 1,746 genes whose 5' UTR sequence information has been organized. Herein, r indicates the Pearson correlation coefficient, and $p<0.01$ shows the results from the test for non-correlation.

As a result, a moderate ($r=0.2737$) but statistically significant ($p<0.01$) correlation between the two index values (predicted relative activity level and ΔPS value) was observed.

This indicates that the predicted relative activity level and the actual ΔPS value will be brought into correlation simply by inputting the information on the specific regions (7 bases and bases 12 to 32 at the 5' end) in the 5' UTR into the regression model constructed by PLS. It was suggested that 7 bases and bases 12 to 32 at the 5' end contribute as the important factors not only to transient expression of reporter mRNA but also to changes in the state of polysome formation by mRNA.

5. Optimal Sequence Free from Translational Repression Even Under Heat Stress 5-1. Extraction of the Optimal 5' UTR Sequence Free from Translational Repression Even under Heat Stress, Using In Silico Analysis Subsequently, based on the model constructed by PLS, the optimal sequence that contributes to the escape from heat stress-induced translational repression of reporter mRNA was extracted.

Specifically, in section 4-1, the PLS regression coefficient for each base at each position was placed as shown in the conceptual diagram of FIG. 19, based on the regression coefficients for the partial base sequences calculated by the PLS model constructed based on the base information of 7 bases and bases 12 to 32 at the 5' end (FIG. 19A). The average of each of the 4 types of bases at each base position was determined, and a t-test was performed (FIG. 19B). Then, the weight (influence on the expression intensity) of each base at each base sequence position was calculated, thereby extracting the optimal sequence.

Figure 20:
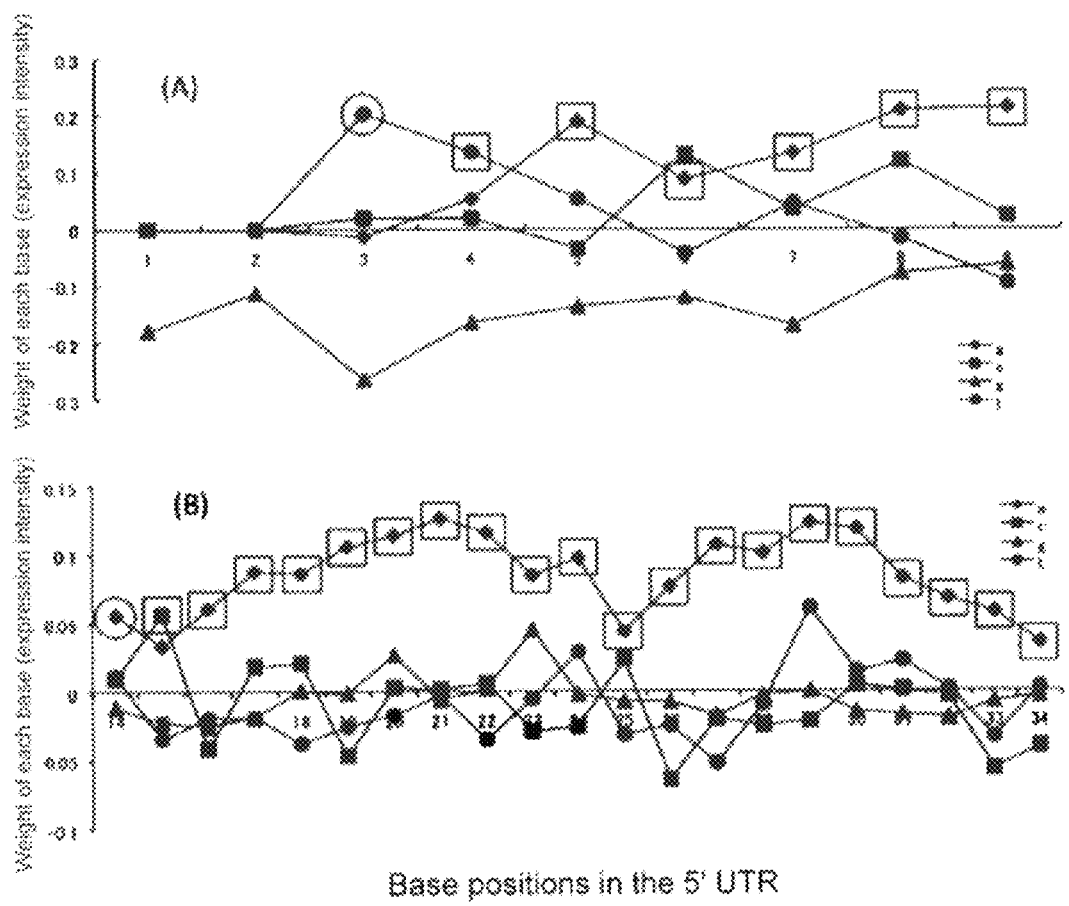
FIG. 20 shows the results from the extraction of a sequence predicted to be the most effective to the escape from translational repression of reporter mRNA under heat stress. The sequence was determined by a PLS model constructed using the sequence information on the 5' UTRs of the 39 genes used in the test and the relative activity level obtained by a transient expression experiment. The abscissa shows the base position in the 5' UTR. The ordinate shows the weight (i.e., expression intensity) of each base, which is calculated based on the model constructed by PLS. A higher weight indicates a greater contribution to the escape from translational repression of reporter mRNA under heat stress. Among the bases with statistical significance (p<0.05), the base with the highest weight at each position is selected and indicated by a square. When none of the 4 bases is statistically significant, the base with the highest weight is selected and indicated by a circle. Each mRNA used in the transient expression experiment contains GG added to the 5' end after transcription from the promoter, and a sequence containing these (GG+5' UTR sequence) was used for in silico analysis. Accordingly, the actual 5' UTR region is obtained by subtracting 2 from the value of the region.

The abscissa in FIG. 20 shows the base position in the 5' UTR. For example, "9" indicates the 9$^{th}$ base from the 5' end. Additionally, the ordinate shows the weight (i.e., expression intensity) of each base, which was calculated based on the model constructed by PLS. When the weight is higher, it means that the base contributes more to the escape from translational repression of reporter mRNA under heat stress. Among the bases with statistical significance (p<0.05), the base with the highest weight was selected (black open square) from the 4 types of bases at each position. When none of the 4 types of the bases was statistically significant, the base with the highest weight at each position was selected (black open circle).

Each mRNA used in the transient expression experiment contains GG added at the 5' end after transcription from the T3 promoter, and the sequence comprising that (GG+5' UTR sequence) was used for in silico analysis. The actual 5' UTR region is obtained by subtracting 2 from the value of the region.

5-2. Examination of the Optimal Sequence Determined by In Silico Analysis by a Transient Expression Experiment Based on the in silico analysis results described in section 5-1, whether the proposed optimal sequence actually contributes to the escape from translational repression of reporter mRNA under heat stress was examined by a transient expression experiment.

The examination method was as follows: using two types of 5' UTRs of different lengths with a low relative activity level (i.e., the 5' UTR (42 bp) of At5g39740 and the 5' UTR (198 bp) of At2g41630), 7 bases and/or bases 12 to 32 at the 5' end were replaced by the above-described optimal sequence(s). Then, a transient expression experiment was performed to examine the influence on reporter mRNA translation under heat stress. The optimal sequence (indicated by "best") for 7 bases at the 5' end was uuaaaaa, and the optimal sequence (indicated by "best") for bases 12 to 32 was acaaaaaaaaaaaaaaaaaaa (SEQ ID NO:8). 7 bases and/or bases 12 to 32 at the 5' end of the tested 5' UTR were replaced by the above sequence(s).

Because initiation codon AUG is produced when bases 12 to 32 in the 5' UTR of At2g41630 are replaced by the optimal sequence, "u" at position 33 was also replaced by "a" (Table 7).

Figure 21:
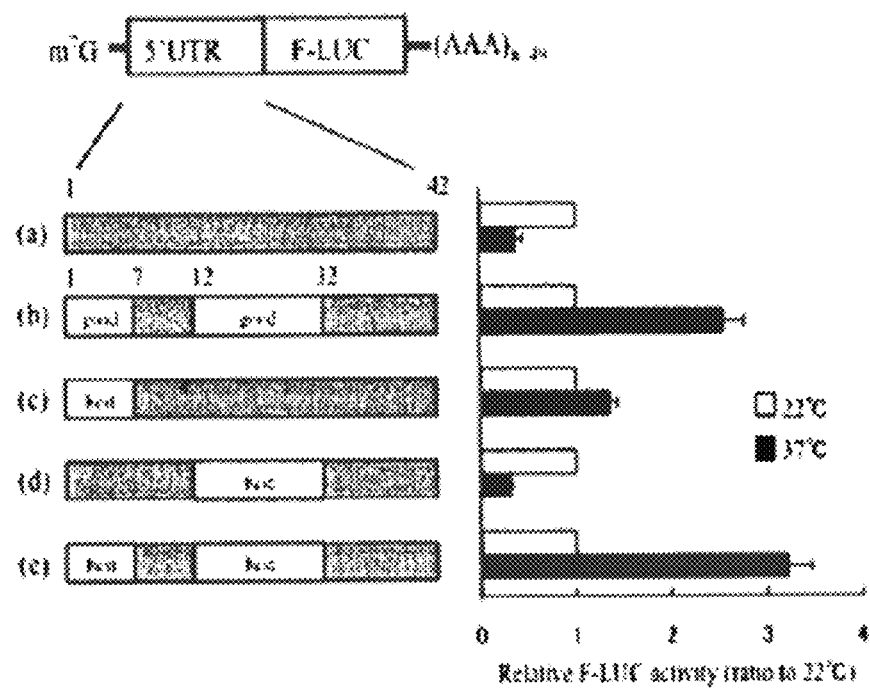
FIG. 21 shows the results from the examination of the influence on reporter mRNA translation under heat stress when 7 bases and bases 12 to 32 at the 5' end of the 5' UTR are replaced by the optimal sequences, using a short 5' UTR (42 bp). The examination is performed to investigate the influence on reporter mRNA translation by the replacement of 7 bases and/or bases 12 to 32 at the 5' end of the 5' UTR of gene (At5g39740) with a low relative activity level by the optimal sequence(s). (a) shows the full length sequence of the 5' UTR. (b) shows a construct obtained by replacing the regions of the bases (indicated by the number) in (a) by the same regions in the 5' UTR (At3g15450, good) with a high relative activity level. (c), (d), and (e) show constructs in which the regions of the bases (indicated by the number) in these 5' UTRs are replaced by the optimal sequences. Further, for the right side of the figure, +cap_5' UTR_f-luc_pA mRNAs to which the 5' UTRs shown in the figure have been individually added are separately introduced into protoplasts with +cap_r-luc_pA mRNA as a control. The protoplasts transfected with the mRNA are divided, and then allowed to stand under normal temperature (22° C.) or heat stress (37° C.) for 20 minutes. The protoplasts are then collected, and the f-luc and r-luc activities are measured. The right side of the figure shows the f-luc activity level when the activity level at 22° C. is assumed to be 1. The values are expressed as averages and standard errors from three independent experiments.

FIG. 21 shows the results of the replacement test of the short 5' UTR (At5g39740).

Examination was performed to investigate the influence on the reporter mRNA by the replacement of 7 bases and/or bases 12 to 32 at the 5' end of the 5' UTR (gray box) of gene At5g39740 with a low relative activity level by the optimal sequence(s).

The left side of FIG. 21 shows the 5' UTR structures. (a) shows the full length sequence of the 5' UTR. (b) shows a construct obtained by replacing the regions of the bases (indicated by the number) in (a) by the same regions (indicated by "good") in the 5' UTR of gene At3g15450 with a high relative activity level. (c), (d), and (e) show constructs in which the regions of the bases (indicated by the number) in these 5' UTRs were replaced by the optimal sequences (indicated by "best").

Table 6 shows the AGI codes, sequences, and the total number of nucleotides in the 5' UTRs (a) to (e) used for the analysis in FIG. 21. The bold and underlined portions are sequences of 7 bases and/or bases 12 to 32 at the 5' end after replacement. +cap_5' UTR_f-luc_pA mRNAs to which the 5' UTR shown in (a) to (e) have been individually added were separately introduced into protoplasts with +cap_r-luc_pA mRNA as a control. The protoplasts transfected with the mRNA were divided into two samples. Subsequently, one sample was allowed to stand under normal temperature (22° C.) for 20 minutes and the other sample under heat stress (37° C.) for 20 minutes. Then, protoplasts were collected from each sample, and the f-luc and r-luc activities were measured.

The right side in FIG. 21 shows the f-luc activity level of each construct when the activity level at 22° C. was assumed to be 1. The results are means and standard errors from three independent experiments. Regardless of the type of +cap_5' UTR_f-luc_pA mRNA tested, the expression from +cap_r-luc_pA mRNA was reduced by a similar amount.

In the case of short 5' UTR (gray box), an increase in the relative activity level was observed by the replacement of 7 bases at the 5' end by the optimal sequence (FIG. 21-c). No influence on the relative activity level was observed when bases 12 to 32 were replaced by the optimal sequence (FIG. 21-d); however, the relative activity level was significantly increased when both regions were replaced by the optimal sequences (FIG. 21-e). Further, the degree of the increase was greater than the case (FIG. 15-h) where the same regions were replaced by the regions of the 5' UTR with a high relative activity level (shown in FIG. 21-b). The above results again indicated the previously demonstrated importance of 7 bases and bases 12 to 32 at the 5' end as well as the contribution of the optimal sequences to the escape from translational repression under heat stress.

TABLE 6

| Sample name | AGI code | Sequence | 5'UTR (nt) |
|---|---|---|---|
| a | At5g39740 | (SEQ ID NO: 48)<br>gcgccucuugccaucuuuugucacucaucuucacaggaaca | 42 |
| b | — | (SEQ ID NO: 49)<br><u>auaacac</u>uugc<u>caagcauuggauuaaucaaag</u>acaggaaaca | 42 |
| c | — | (SEQ ID NO: 50)<br><u>uuaaaaa</u>uugccaucuuuugucacucaucuucacaggaaaca | 42 |

TABLE 6-continued

| Sample name | AGI code | Sequence | 5'UTR (nt) |
|---|---|---|---|
| d | — | gcgccucuugcacaaaaaaaaaaaaauauaaaacaggaaaca (SEQ ID NO: 51) | 42 |
| e | — | uuaaaaauugcucaaaaaaaaaaaaaaaaaaaacaggaaaca (SEQ ID NO: 52) | 42 |

Figure 22:
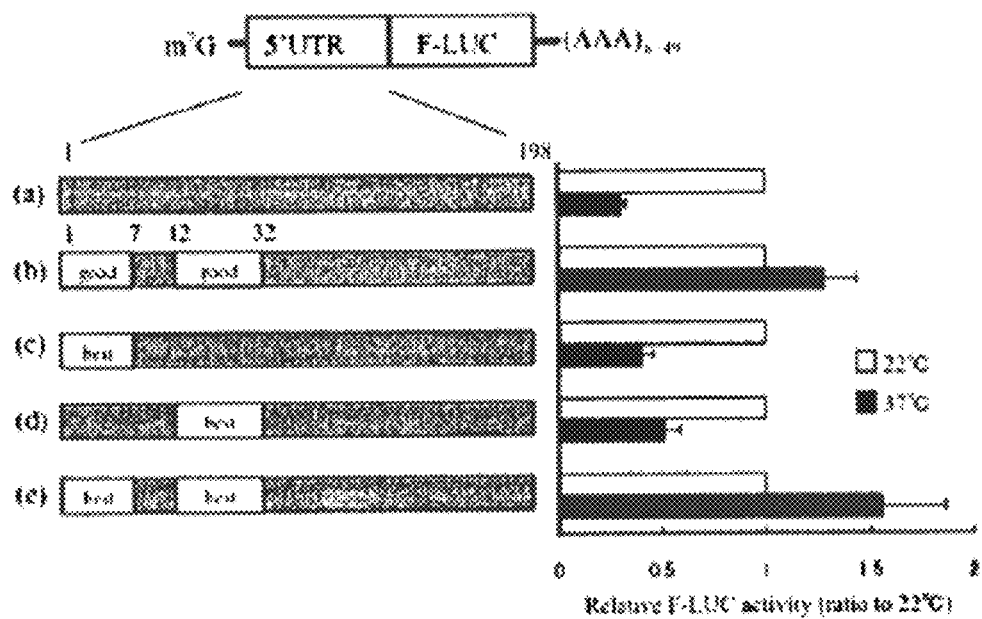
FIG. 22 shows the results from the examination of the influence on reporter mRNA translation under heat stress when 7 bases and bases 12 to 32 at the 5' end of the 5' UTR are replaced by the optimal sequences, using a long 5' UTR (198 bp). The examination is performed to investigate the influence on reporter mRNA translation by the replacement of 7 bases and/or bases 12 to 32 at the 5' end of the 5' UTR (At2g41630) with a low relative activity level by the optimal sequence(s). (a) shows the full length sequence of the 5' UTR. (b) shows a construct obtained by replacing the regions (indicated by the number) in (a) by the same regions in the 5' UTR (At4g12000, good) with a high relative activity level. (c), (d), and (e) show constructs in which the regions of the bases (indicated by the number) in these 5' UTRs are replaced by the optimal sequences. In regard to (d) and (e), because initiation codon AUG is produced when bases 12 to 32 are replaced by the optimal sequence, "u" at position 33 is replaced by "a." Further, for the right side of the figure, +cap_5' UTR_f-luc_pA mRNAs to which the separate 5' UTRs have been individually added are separately introduced into protoplasts with +cap_r-luc_pA mRNA as a control. The protoplasts transfected with the mRNA are divided, and then allowed to stand under normal temperature (22° C.) or heat stress (37° C.) for 20 minutes. The protoplasts are then collected, and the f-luc and r-luc activities are measured. The right side of the figure shows the f-luc activity level when the activity level at 22° C. is assumed to be 1. The values are expressed as averages and standard errors from three independent experiments.

5' UTRs Used for the Analysis in FIG. 21, and the Sequence Information of the 5' UTRs after Replacement Further, FIG. 22 shows the results of the replacement test of the long 5' UTR (At2g41630).

Examination was performed to investigate the influence on the reporter mRNA by the replacement of 7 bases and/or bases 12 to 32 at the 5' end of the 5' UTR (gray box) of gene At2g41630 with a low relative activity level by the optimal sequence(s).

The left side of FIG. 22 shows the 5' UTR structures. (a) shows the full length sequence of the 5' UTR. (b) shows a construct obtained by replacing the regions of the bases (indicated by the number) in (a) by the same regions (indicated by "good") in the 5' UTR of gene At4g12000 with a high relative activity level.

(c), (d), and (e) show the constructs in which the regions of the bases (indicated by the number) in these 5' UTRs were replaced by the optimal sequences (indicated by "best"). In regard to (d) and (e), because AUG would be produced when bases 12 to 32 are replaced by the optimal sequence, "u" at position 33 was replaced by "a."

Further, Table 7 shows the AGI codes, sequences, and the total number of nucleotides in the 5' UTRs (a) to (e) used for the analysis in FIG. 15. The bold and underlined portions are sequences of 7 bases and/or bases 12 to 32 at the 5' end after replacement.

+cap_5' UTR_f-luc_pA mRNAs to which the 5' UTRs shown in (a) to (e) have been individually added were separately introduced into protoplasts with +cap_r-luc_pA mRNA as a control. The protoplasts transfected with the mRNA were divided into two samples. Subsequently, one sample was allowed to stand under normal temperature (22° C.) for 20 minutes and the other sample under heat stress (37° C.) for 20 minutes. Then, protoplasts were collected from each sample, and the f-luc and r-luc activities were measured.

The right side in FIG. 22 shows the f-luc activity level of each construct when the activity level at 22° C. was assumed to be 1. The results are averages and standard errors from three independent experiments. Regardless of the type of +cap_5' UTR_f-luc_pA mRNA tested, the expression from +cap_r-luc pA mRNA was reduced by a similar amount.

TABLE 7

| Sample Name | AGI code | Sequence | 5'UTR (nt) |
|---|---|---|---|
| a | At2g41630 | ccuucuccacauaaguuacaucucucguguuuuguuuucuuugucuccgauuuuuuucgc gacgaagaagaagacgagagauagagagagaaguagagaaaucgaaggaaucuguaaccgauuuuaagau cucaauuuuuagggguuguugauuuuucaauuucgggguuaauuuuuuuuagggguuuucauuuggaauc (SEQ ID NO: 53) | 198 |
| b | — | auuaacacacaaaccgaaaaaagaaaaaaacuuguuuucuuugucuccgauuuuuuucgcgacgaagaag aagacgagagauagagagagaaguagagaaaucgaaggaaucuguaaccgauuuuaagaucucaauuuuu agggguuguugauuuuucaauuucgggguuaauuuuuuuuagggguuuucauuuggaauc (SEQ ID NO: 54) | 198 |
| c | — | uuaaaaacacauaaguuacaucucucguguuuuguuuucuuugucuccgauuuuuuucgcgacgaagaag aagacgagagauagagagagaaguagagaaaucgaaggaa ucuguaaccgauuuuaagaucucaauuuuu agggguuguugauuuuucaauuucgggguuaauuuuuuuuagggguuuucauuuggaauc (SEQ ID NO: 55) | 198 |
| d | — | ccuucuccacaacaaaaaaaaaaaaaaaaaaaaguuuucuuugucuccgauuuuuuucgcgacgaagaag aagacgagagauagagagagaaguagagaaaucgaaggaaucuguaaccgauuuuaagaucucaauuuuu agggguuguugauuuuucaauuucgggguuaauuuuuuuuagggguuuucauuuggaauc (SEQ ID NO: 56) | 198 |
| e | — | uuaaaaacacaacaaaaaaaaaaaaaaaaaaaaguuuucuuugucuccgauuuuuuucgcgacgaagaag aagacgagagauagagagagaaguagagaaaucgaaggaaucuguaaccgauuuuaagaucucaauuuu uagggguuguugauuuuucaauuucgggguuaauuuuuuuuagggguuuucauuuggaauc (SEQ ID NO: 57) | 198 |

5' UTRs Used for the Analysis in FIG. 22, and the Sequence Information of the 5' UTRs after Replacement In the case of the long 5' UTR (gray box), an increase in the relative activity level was observed by the replacement of 7 bases at the 5' end by the optimal sequence (FIG. 22-c). An increase in the relative activity level was also observed when bases 12 to 33 were replaced by the optimal sequence (FIG. 22d). The relative activity level was significantly increased when both regions were replaced by the optimal sequences (FIG. 22-e). The degree of the increase was greater than the case where the same regions were replaced by the regions of the 5' UTR with a high relative activity level (shown in FIG. 22-b). The above results again indicated the previously demonstrated importance of 7 bases and bases 12 to 32 (33) at the 5' end as well as the effect of the optimal sequences.

As described above, in the experiment of the replacement using two types of 5' UTRs, the relative activity level was increased by the optimal sequences offered by the calculation of the weight of each base at each base position using in silico analysis. This is considered to be a result that supports the usefulness of in silico analysis that uses PLS analysis that derived the previously demonstrated importance of 7 bases and bases 12 to 32 at the 5' end.

Figures 23, 24:
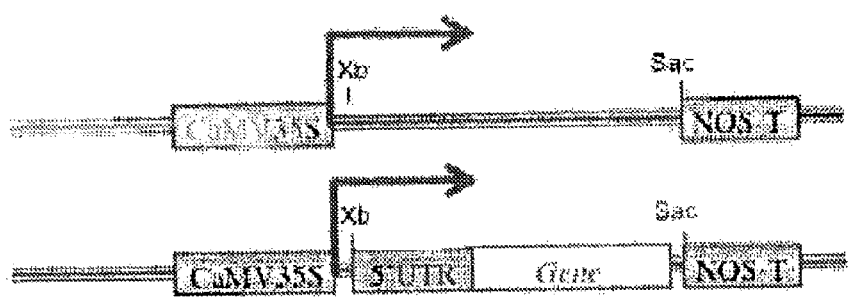
FIG. 23 shows a construction diagram of a common plant expression vector. "CaMV35S" is a promoter region derived from cauliflower mosaic virus 35S rRNA, and "NOS-T" is a terminator region derived from nopaline synthetic enzyme gene of *Agrobacterium*. "Xb" and "Sac" are respectively XbaI and SacI restriction enzyme recognition sites. The arrows indicate the transcription initiation point and the transcriptional direction.
FIG. 24 shows a schematic view of synthetic mRNA used for the examination. At1g77120+ shows the mRNA in which a vector-derived sequence, which would be expected to be added, is added to the 5' UTR of At1g77120. At1g77120 shows the mRNA containing only the 5' UTR of At1g77120. Further, C indicates the transcription initiation point of CaMV35S promoter, i.e., the 5' end of the 5' UTR.

6. Form of Ligation of the 5' UTR Capable of Escaping Translational Repression to the Vector DNA Normally, a plant expression vector to which a useful gene and a 5' UTR are ligated is constructed using restriction enzyme sites located downstream of the promoter region of the vector as the basis (FIG. 23). FIG. 23 shows a construction diagram of a general plant expression vector. In this case, a 5' UTR and a gene are introduced into the XbaI and SacI sites of an expression vector as the basis.

However, in this case, a sequence derived from the vector is added to the 5' side of the mRNA transcribed from the promoter. In other words, an extra sequence from the transcription initiation point to the restriction enzyme site used for the construction is added to the 5' side of the original 5' UTR. On the other hand, as shown in the results described in section 4-4, it is clear that the important feature of the 5' UTR capable of escaping heat stress-induced translational repression is not that the regions of 7 bases and bases 12 to 32 at the 5' end of the 5' UTR are simply present in the 5' UTR but that these regions are present at the 5' end side. Therefore, the ability to escape translational repression induced by stress may not be demonstrated when the construction as shown in FIG. 23 is obtained.

6-1 Influence of the Vector-Derived Sequence on Reporter mRNA Translation under Heat Stress Two types of mRNAs were synthesized: one to which the 5' UTR of At1g77120 with a high relative activity level was added, and the other to which a vector-derived sequence, which would be expected to be present when the 5' UTR was ligated to the vector using the XbaI site shown in FIG. 23, was added to the immediately up-stream of the 5' UTR of At1g77120. Then, a transient expression experiment was carried out to examine the influence on the escape from translational repression when the vector-derived sequence was added.

FIG. 24 shows the structure of the 5' UTR. (At1g77120+) is the mRNA in which a possibly occurring vector-derived sequence was added to the 5' UTR of At1g77120. (At1g77120) is the mRNA containing only the 5' UTR of At1g77120. Further, C indicates the transcription initiation point of CaMV35S promoter, i.e., the 5' end of the 5' UTR.

Table 8 shows 5' UTR sequences of (At1g77120+) and (At1g77120).

Figure 25:
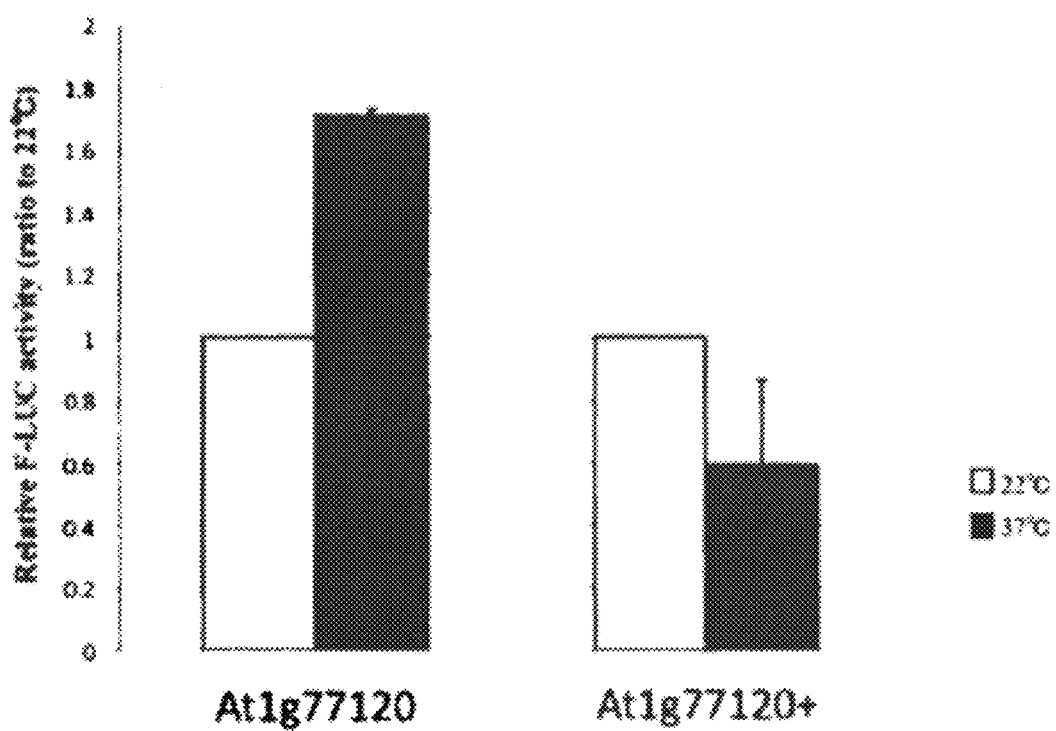
FIG. 25 shows the f-luc activity level of each construct of At1g77120+ and At1g77120 shown in FIG. 24 when the activity level at 22° C. is assumed to be 1. The values are expressed as averages and standard errors from three independent experiments.

+cap_5' UTR_f-luc_pA mRNAs to which the 5' UTRs shown in FIG. 24 have been individually added were separately introduced into protoplasts with +cap_r-luc_pA mRNA as a control. The protoplasts transfected with the mRNA were divided into two samples. Subsequently, one sample was allowed to stand under normal temperature (22° C.) for 20 minutes and the other sample under heat stress (37° C.) for 20 minutes. Then, protoplasts were collected from each sample, and the f-luc and r-luc activities were measured. FIG. 25 shows the f-luc activity level of each construct (At1g77120+ and At1g77120) shown in FIG. 24 when the activity level at 22° C. was assumed to be 1. The results are averages and standard errors from three independent experiments. Regardless of the type of +cap_5' UTR_f-luc_pA mRNA tested, the expression from +cap_r-luc_pA mRNA was reduced by a similar amount.

The relative activity level was significantly reduced when a vector-derived sequence, which would be expected to be present after the construction of the expression vector, was added to the 5' UTR of At1g77120, which is capable of escaping translational repression under heat stress.

Based on the above, it became clear that the 5' UTR capable of escaping translational repression even under stress must be ligated to an appropriate position, specifically, a site immediately downstream of the transcription initiation point of the promoter, in order to allow the gene introduced into a plant to be expressed and efficiently translated even under stress without repression.

7. Creation of Stably Transformed Cells 7-1 Binary Vector Construction

The NOS terminator region of plasmid AtADH NF (Sugio et al., J. Biosci. Bioeng., 3, 300-302. 2008) in which the 5' UTR of At1g77120+ is inserted between CaMV35S promoter and GUS gene (β-glucuronidase gene) was replaced by the HSP terminator (Nagaya et al., Plant Cell Physiol. 51(2): 328-332 (2010)), using the SacI and EcoRI sites. Using forward primers having the XbaI site and backward primers having the StuI site at the 3' side (Table 9), the 5' UTRs of At4g14560, At3g47610, At5g39740, and At5g39740-S were subjected to PCR, with pT3-5' UTR-FL-pA plasmids as templates into which these 5' UTRs have been separately introduced. The resulting PCR products were separately inserted into At1g77120+HF HSP-T plasmids using the XbaI and StuI sites to replace the 5' UTR thereof. The thus-obtained plasmids were named At4g14560+NF HSP-T, At3g47610+NF HSP-T, At5g39740+NF HSP-T, and At5g39740-S+NF HSP-T. Next, inverse PCR was performed using forward and backward primers (Table 10) in order to remove the extra sequence between the transcription initiation point of CaMV35S promoter and the 5' UTR in each plasmid. The PCR products were self-ligated, and the thus-obtained plasmids were named At4g14560 NF HSP-T, At1g77120 NF HSP-T, At3g47610 NF HSP-T, At5g39740NF HSP-T, and At5g39740-S NF HSP-T. Further, the absence of mutations was confirmed by base sequence determination. Lastly, HindIII/EcoRI fragments of At4g14560+NF HSP-T, At1g77120+NF HSP-T, At4g14560 NFHSP-T, At1g77120

TABLE 8

| Sample Name | Sequence |
|---|---|
| At1g77120+ | cacgggggacucuagauacaucacaaucacacaaaacuaacaaaagaucaaaagcaaguucuucacuguugaua (SEQ ID NO: 58) |
| At1g77120 | uacaucacaaucacacaaaacuaacaasagaucaaaagcaaguucuucacuguugaua (SEQ ID NO: 59) |

Sequence Information of the 5' UTRs Used for Analysis in FIG. 25

Figure 26:
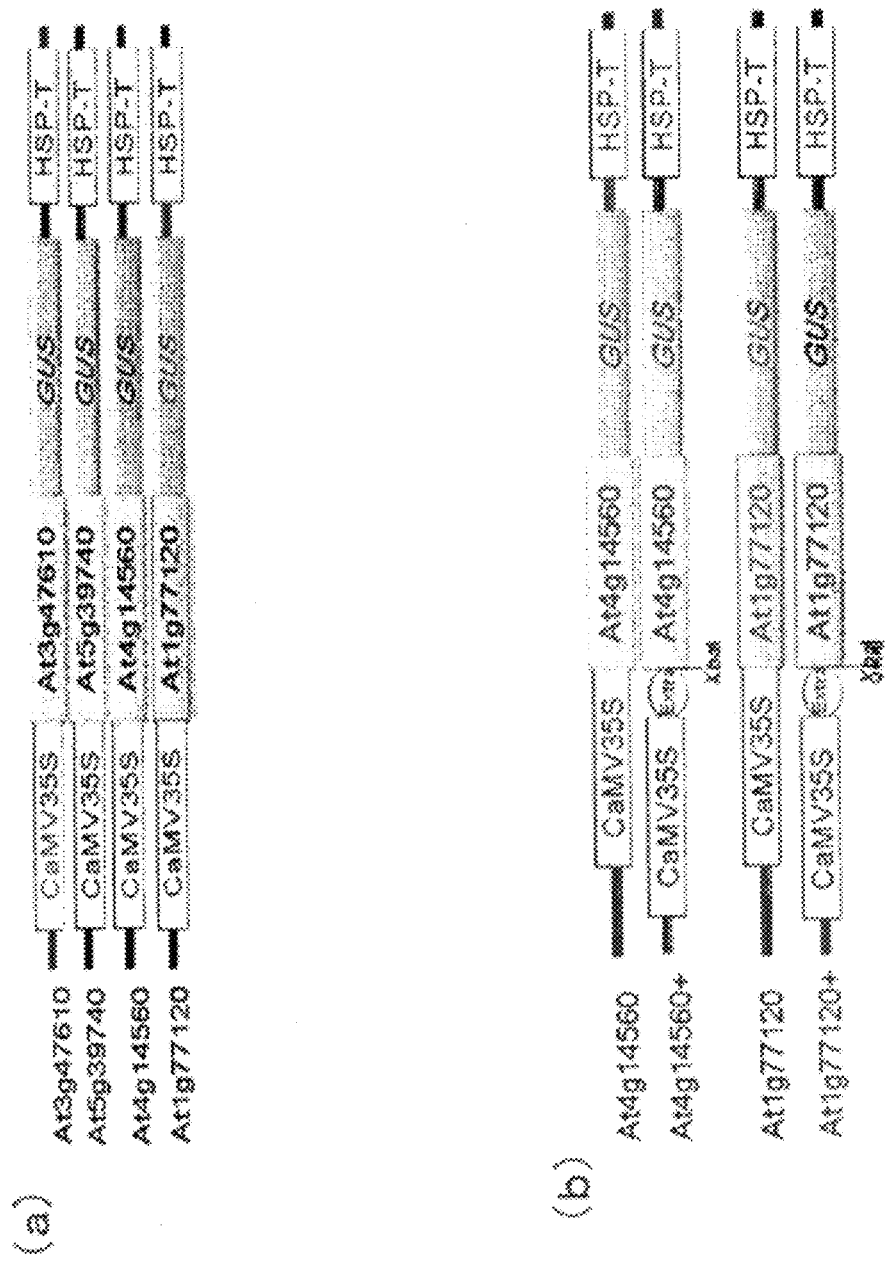
FIG. 26a shows a construction diagram of binary vectors constructed by separately adding the 5' UTR of At4g14560, At1g77120, At3g47610, and At5g39740 to reporter GUS genes each having HSP terminator at the downstream, and placing the constructs under CaMV35S promoter control.
FIG. 26b shows a construction diagram of the binary vectors introduced into cells transformed with At4g14560+ and cells transformed with At1g77120+.

NF HSP-T, At3g47610 NF HSP-T, At5g39740 NF HSP-T, and At5g39740-S NF HSP-T were separately inserted into pRI910 (Takara Bio), thereby producing vectors for transformation. The produced binary vectors were separately introduced into *Agrobacterium tumefaciens* EHA105 strains by electroporation, and the strains were stored as glycerol stock at −80° C. FIG. 26 shows an example of the construction diagram of the produced binary vector.

Table 9

TABLE 9

| 5'UTR (AGI code) | Primer sequences (5' to 3') |
|---|---|
| At4g14560 | actctagaacacaagcattttcaaggatat (SEQ ID NO: 61) |
| | tgaggccttaacatattctctcactata (SEQ ID NO: 62) |
| At3g47610 | actctagacctttcttgtcgtcgtttcgaa (SEQ ID NO: 63) |
| | tgaggccttaacatcttcttctccgattct (SEQ ID NO: 64) |
| At5g39740 | actctagagcgcctcttgccatcttttgtc (SEQ ID NO: 65) |
| | tgaggccttaacattgatectgtgaagat (SEQ ID NO: 66) |
| At5g39740-S | actctagattaaaaattgcacaaaaaaaaa (SEQ ID NO: 67) |
| | tgaggccttaacattgtttcctgtttatt (SEQ ID NO: 68) |

Primer Sequences Used for PCR in 7-1

Primer Sequences Used for PCR in 7-1

TABLE 10

| 5'UTR (AGI code) | Primer sequences (5' to 3') |
|---|---|
| At4g14560 | acacaagcattttcaaggata (SEQ ID NO: 69) |
| At1g77120 | tacatcacaatcacacaaaac (SEQ ID NO: 70) |
| At3g47610 | cctttcttgtcgtcgtttcga (SEQ ID NO: 71) |
| At5g39740 | gcgcctcttgccatcttttgtc (SEQ ID NO: 72) |
| At5g39740-S | ttaaaaattgcacaaaaaaaaaaaaaaaaaacagg (SEQ ID NO: 73) |
| backward (universal) | ttctctccaaatgaaatgaac (SEQ ID NO: 74) |

Primer Sequences Used for Inverse PCR

Primer Sequences Used for Inverse PCR 7-2 Introduction of the Binary Vector into Cultured Cells by the *Agrobacterium* Method On day 7 after entering stationary phase, 2 mL of *Arabidopsis thaliana* cultured cells (T87) were subcultured into fresh modified LS medium (95 mL) and cultured at 22° C. with shaking in a 24-hour light period for 3 days. On day 3, the culture medium of *Arabidopsis thaliana* cultured cells (T87) was inoculated with 500 μL or 1 mL (O.D.600 measured value 1) of *Agrobacterium* (transfected with each binary vector produced) cultured in 2×YT medium (described in Molecular Cloning (Sambrook et al., 2001)). At the same time, acetosyringone of a final concentration of 100 μM was added thereto, and co-cultivation was carried out at 22° C. in a continuous light period with shaking at a stirring rate of 120 rpm for 2 days. Subsequently, 50 mL (half of the full length amount) of the co-culture medium was transferred to a 50-mL falcon tube, followed by centrifugation (800×g, 1 min., 4° C.). Then, the supernatant was removed, and washes were performed (5 times) by adding about 20 mL of 100 mg/L modified LS medium containing carbenicillin sodium (washing medium). The washed cultured cells were transferred into 100 mL of washing medium and cultured for recovery at 22° C. in a continuous light period with shaking at a stirring rate of 120 rpm for 2 days. The total amount of cultured cells that were cultured for recovery was washed with washing medium (the washing method is as defined above). 1 mL or 500 μL of the mixture of equal amounts of washed cultured cells and washing medium was spread onto a modified LS Km Cb plate (modified LS medium, 40 mg/L of kanamycin, 250 mg/L of carbenicillin sodium, and 3 g/L of gellan gum). After standing at 22° C. in a continuous light period for 2 to 3 weeks, the formed callus was removed to a fresh modified LS Km Cb plate. Further, the calli showing good growth were selected and stained with GUS, which is described later. After expression of GUS gene was confirmed, the full grown callus mass was cultured in 95 mL of modified LS Km Cb liquid medium and used in subsequent experiments.

7-3 Confirmation of Stably Transformed Cells by GUS Staining

GUS staining was performed essentially in accordance with the method of Jefferson et al. (Jefferson et al., 1987, EMBO J. 6, 3901-3907). 0.1 mM 5-Bromo-4-chloro-3-indoxyl-beta-D-glucuronide cyclohexylammonium salt (x-gluc) was added to the prepared GUS extraction buffer (50 mM $NaH_2PO_4$ pH 7.0, 10 mM beta-mercaptoethanol, 10 mM $Na_2EDTA$) immediately before staining, and 1 mL of the mixture was added to the collected callus mass, followed by stirring and standing at 37° C. for 30 minutes to 2 hours. Changes in the color were observed. The callus in which GUS gene expression was confirmed was used as transformed cells in the experiments described below (polysome analysis, RT-PCR, and GUS activity measurement).

7-4 Subculture of Stably Transformed Cells

Culturing was performed at 22° C. in an 18-hour light period/6-hour dark period and at a stirring rate of 120 rpm. 95 mL of modified LS Km Cb liquid medium was used in a 300-mL Erlenmeyer flask. Every week, 4 to 10 mL of cells that entered stationary phase were transplanted into 95 mL of fresh medium for subculture.

8 Polysome/RT-PCR Assay 8-1 Growing Conditions and Stress Treatment of Stably Transformed Cells The transformed cells were subjected to heat stress treatment or salt stress treatment. For heat stress treatment of the transformed cell, cells on day 3 of culturing were used and cultured at 37° C. for 10 minutes with shaking. After heat stress treatment, the medium was filtered off with suction, frozen in liquid nitrogen, and stored at −80° C. Normal cells were treated in the same manner as in the heat stress-treated cells, except that the temperature was 22° C. Transformed cells on day 3 of culturing were also used for salt stress treatment. After adding NaCl to the cell culture medium to obtain the final concentration of 200 mM, the cells were cultured under normal culture conditions (the conditions described in section 7-4 above) for 10 minutes with shaking. The cells obtained by filtration with suction were frozen in liquid nitrogen and stored at −80° C.

8-2 Polysome Analysis Using Sucrose Density Gradient Centrifugation

Polysome analysis using sucrose density gradient centrifugation was performed in accordance with the method of Davis et al. (Davies, E., and Abe, S. 1995, Methods Cell Biol. 50, 209-222). 300 mg of normal cells or heat stress-treated/salt stress-treated cells were finely ground with a pestle and a mortar in liquid nitrogen. Then, 1.5 mL of buffer U (200 mM tris-HCl, pH 8.5, 50 mM KCl, 25 mM MgCl$_2$, 2 mM EGTA, 100 µg/mL heparin, 2% polyoxyethylene 10-tridecyl ether, 1% sodium deoxycholate) was added to the ground particles to gently suspend the cells. After cell debris was removed by centrifugation (15,000×g, 10 min., 4° C.), the supernatant was layered on 4.5 mL of 15-60% sucrose density gradient prepared in buffer B (50 mM tris-HCl, pH 8.5, 25 mM KCl, and 10 mM MgCl$_2$), followed by ultracentrifugation (SW55Ti rotor, 55,000 rpm, 50 min., 4° C., brake off) (Beckman Coulter). A micropipette (40 µL calibrated pipette; Drummond) connected to a peristaltic pump (Minipuls 3; Gilson) was inserted into the sucrose density gradient from the above, and the sucrose density gradient solution was aspirated at a rate of about 1 mL/min. At the same time, the absorbance at 254 nm was recorded using an AC-5200 Biomini UV-absorbance Monitor (ATTO).

8-3 RNA Extraction (15 Fractions) from the Solution Subjected to Sucrose Density Gradient Centrifugation 350 µL of solution subjected to sucrose density gradient centrifugation was collected into each of 15 tubes to which 8 M guanidine hydrochloride had been added in advance to obtain a final concentration of 5.1 M. 100% ethanol in the same amount as the mixture was added thereto, followed by cooling overnight at −20° C. and then centrifugation (12,000× g, 45 min., 4° C.). The thus-obtained pellet was washed once with 85% ethanol and dried. The subsequent RNA purification was performed using an RNeasyMini Kit (Qiagen) in accordance with the accompanying protocol (Dnase I treatment was performed as an option). RNA in all fractions was dissolved in 30 µL of RNase-free water. The quality of purified RNA was tested by 1.5% denaturing gel electrophoresis.

8-4 RT-PCR

The same amount of purified RNA solution from each of the 15 fractions was used to perform reverse transcription reaction. Reverse transcription reaction was performed using a Transcriptor First Strand cDNA Synthesis Kit (Roche). The volume of the reaction system was 20 µL (oligo dT primer was used). A specific cDNA product obtained by PCR reaction was amplified using gene-specific primers (Table 11) and a KAPA Taq Extra PCR Kit (Kapa Biosystems) (the volume of the reaction system was 20 µL) with 2 to 3 µL of 1:2 diluted reverse transcription reaction solution as a template. The amplification product was visualized with agarose electrophoresis and EtBr staining. The cycle number of PCR was set in the exponential amplification phase of PCR products.

TABLE 11

| Target gene | Primer sequences (5' to 3') |
| --- | --- |
| GUS | (SEQ ID NO: 75) ccttacgctgaagagatgctcg |
|  | (SEQ ID NO: 76) attcggtgatgataatcggctg |
| At4g14560 | (SEQ ID NO: 77) cgactcaacagaagaatctg |
|  | (SEQ ID NO: 78) cgtatttgtaaccctattgc |

TABLE 11-continued

| Target gene | Primer sequences (5' to 3') |
| --- | --- |
| At1g77120 | (SEQ ID NO: 79) gagtattcgttgcatcatcacc |
|  | (SEQ ID NO: 80) caaagtgaacatcatctgcga |
| At3g47610 | (SEQ ID NO: 81) cggccgtaaggttctgttaaat |
|  | (SEQ ID NO: 82) ccatccgacgtggactcaac |
| At3g18780 (Act2) | (SEQ ID NO: 83) atggctgaggctgatgatat |
|  | (SEQ ID NO: 84) ttagaaacattttctgtgaacgattc |

Primer Sequences Used for PT-PCR

Primer Sequences Used for PT-PCR

Figure 27:
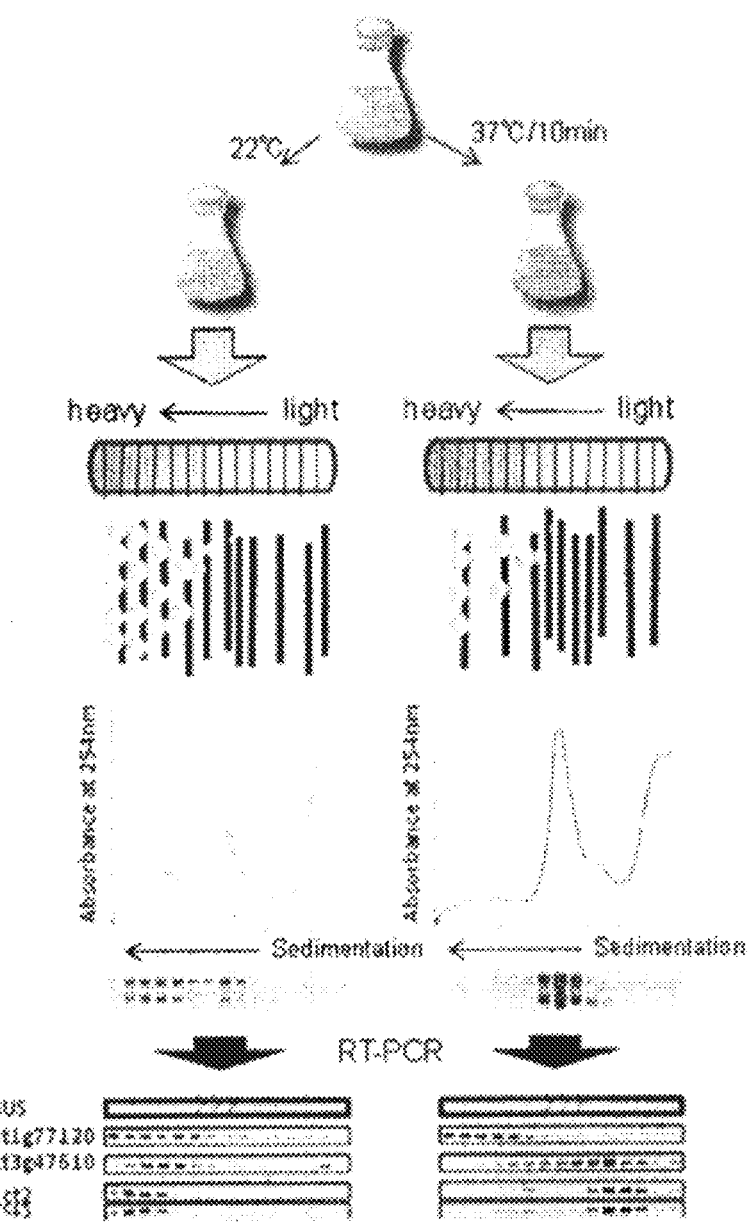
FIG. 27 summarizes polysome/RT-PCR assay.

FIG. 27 summarizes the polysome/RT-PCR assay. Because the number of ribosomes binding to the mRNA serves as an index that indicates translation efficiency (translation is actively performed when many ribosomes are bound to the mRNA, forming polysomes, whereas translation is repressed when ribosomes are released from the mRNA, not forming polysomes) (Mathews et al., 2007, Cold Spring Harbor, N.Y.: Cold Spring Harbor Laboratory Press, pp. 1-40.; Kawaguchi and Bailey-Serres, Kawaguchi R., and Bailey-Serres J., 2002, Curr Opin Plant Biol. 5, 460-5), polysome analysis in which the mRNA present in the cell extract can be fractionated according to the number of bound ribosomes by sucrose density gradient centrifugation is widely used as a method to analyze changes in the translational state of the cells. Further, by purifying RNA from each fraction of the sucrose density gradient solution, which was fractionated according to the number of bound ribosomes, and performing RT-PCR, it is possible to analyze behavioral changes induced by the presence or absence of stress between GUS mRNA containing a different 5' UTR and endogenous gene mRNA. The ability of each 5' UTR to maintain translation can be examined by performing such polysome/RT-PCR as described above. In order to ensure reproducibility, two lines were analyzed for each transformed cell type.

8-5 Analysis Results

Heat Stress Treatment

Cells Transformed with At3g47610

Figure 28:
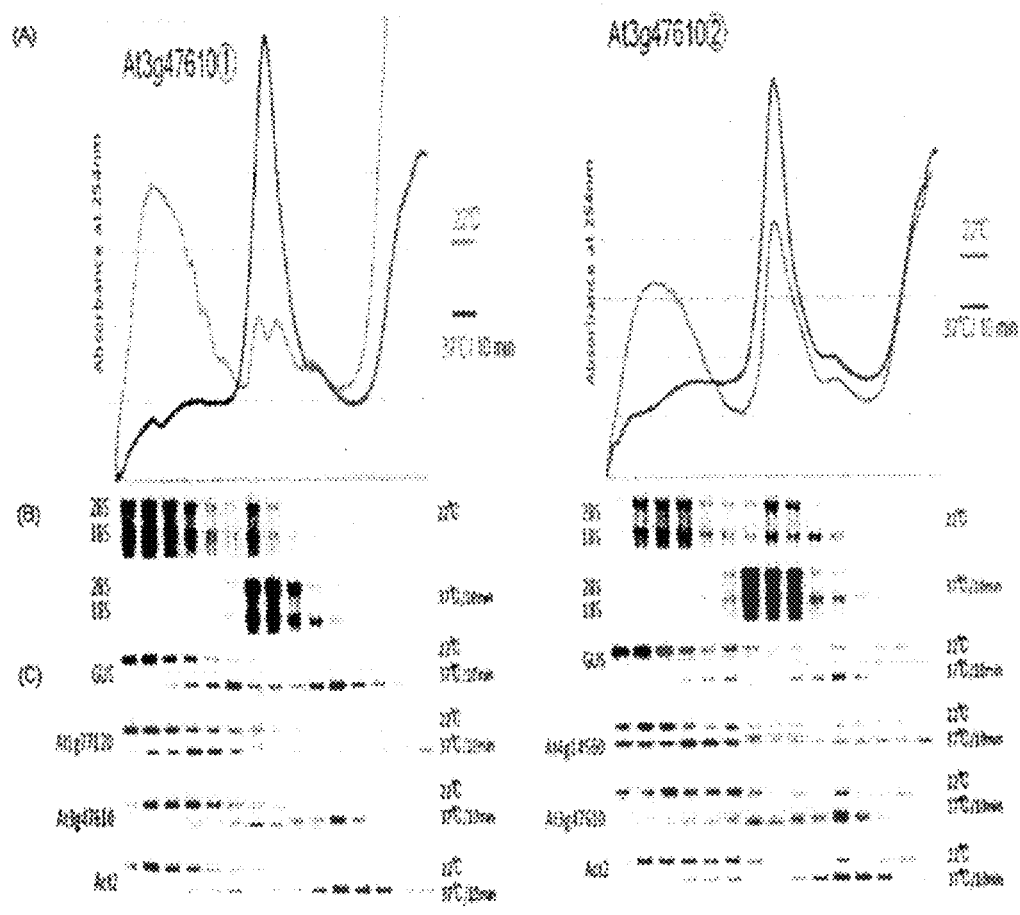
FIG. 28 shows the results from polysome/RT-PCR assay of cells transformed with At3g47610 and the results obtained using two independently isolated lines of transformed cells.

Cells transformed with At3g47610 were subjected to heat stress treatment at 37° C. for 10 minutes. A decrease in the polysome fractions and an increase in the non-polysome fraction compared to normal cells were indicated by the absorbance profile at 254 nm that uses the amount of RNA as an index (FIG. 28A). Further, the fact that the distribution of 28S rRNA and 18S rRNA (components of ribosome) in the sucrose density gradient solution reflects the behavior of the absorbance profile was also confirmed by fractioning the sucrose density gradient solution after centrifugation and subjecting the RNA collected from each fraction to agarose electrophoresis (FIG. 28B). Further, based on the results of array analysis, the distribution of the mRNA of At1g77120 or At4g14560 (a gene whose translation is maintained even under heat stress) in the sucrose density gradient solution was examined by RT-PCR. The results show that the mRNA remained in the polysome fraction without undergoing translational repression even under heat stress conditions (37° C./10 min.) (FIG. 28C). On the other hand, the results of array analysis shows that in the case of the mRNA of housekeeping genes Actin2 (Act2) and At3g47610 susceptible to translational repression under heat stress, the distribution of the mRNA was remarkably shifted from the polysome fraction to non-polysome fraction by heat stress treatment (FIG. 28C), and that in the case of GUS mRNA to which the 5' UTR of At3g47160 was added, polysome formation was inhibited under heat stress, causing repression of translation (FIG. 28C), as is the case with At3g47610 mRNA.

Cells Transformed with At5g39740

Figure 29:
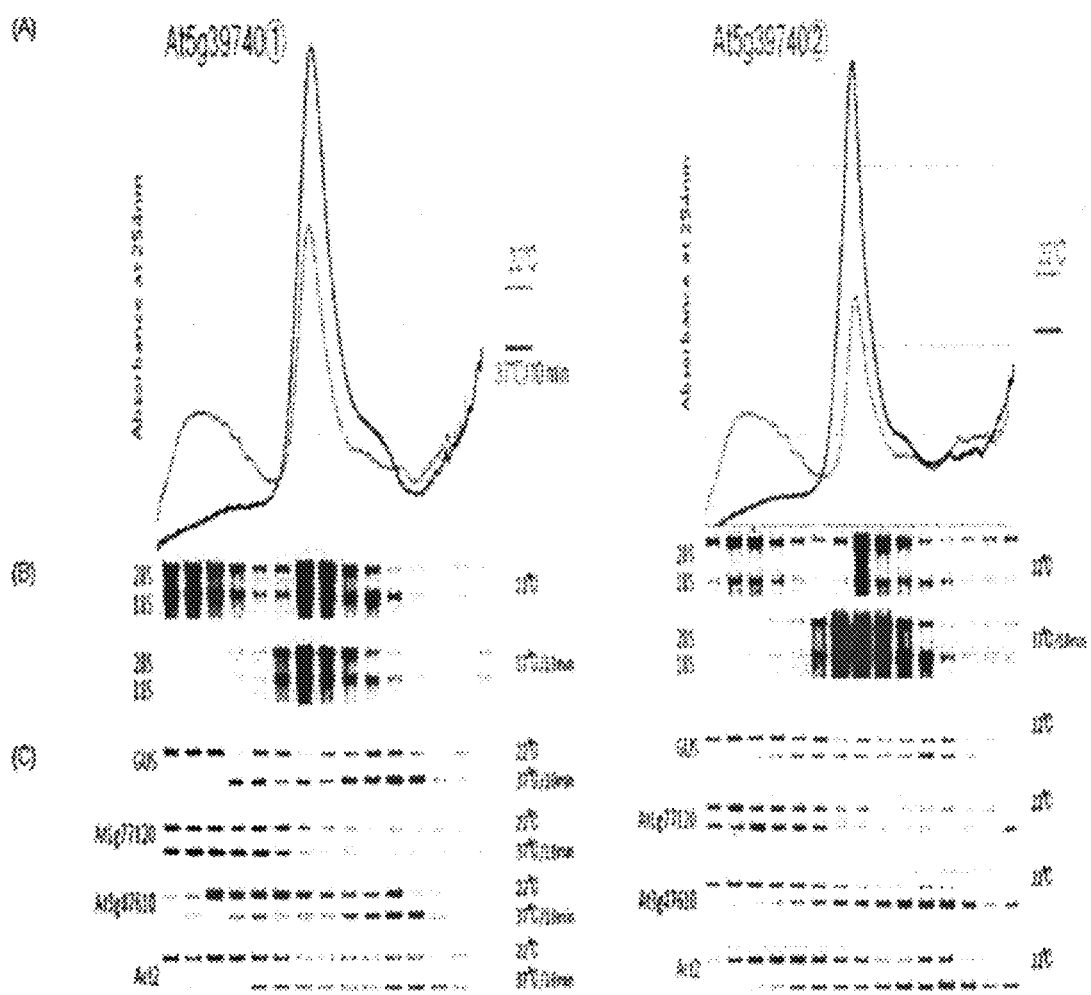
FIG. 29 shows the results from polysome/RT-PCR assay of cells transformed with At5g39740 and the results obtained using two independently isolated lines of transformed cells.

Cells transformed with At5g39740 were also analyzed in a similar manner as the cells transformed with At3g47610. The results show, as is the case with the cells transformed with At3g47610, a decrease in the polysome fraction and an increase in the non-polysome fraction, which were induced by stress treatment (FIG. 29A), consistency between the distribution of 28S rRNA and 18S rRNA in the sucrose density gradient solution and the behavior of the absorbance profile (FIG. 29B), maintenance of polysome formation by At1g77120 mRNA, and a shift of the mRNA of Act2 and At3g47610 to the non-polysome fraction (FIG. 29C). Further, in the case of GUS mRNA containing the 5' UTR of At5g39740 (a gene whose translation is repressed under heat stress), translation under heat stress was repressed (FIG. 29C), as is the case with when the 5' UTR of At3g47610 was used.

The results of the analysis using the cells transformed with At3g47610 and the cells transformed with At5g39740 show that when the 5' UTR of a gene whose translation is repressed under heat stress was added to a transgene, the translation of the transgene was repressed under heat stress, as is the case with the endogenous gene.

Cells Transformed with At4g14560

Figure 30:
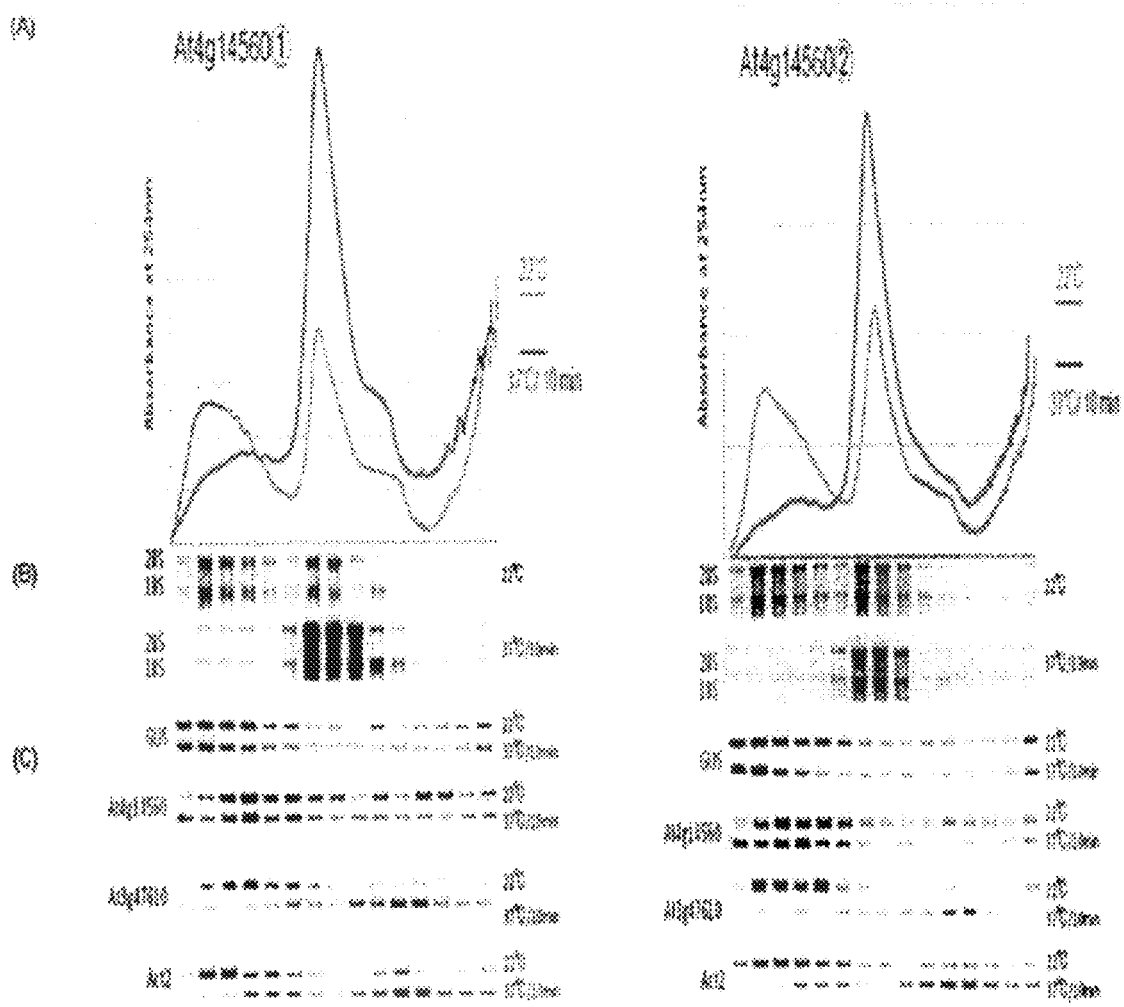
FIG. 30 shows the results from polysome/RT-PCR assay of cells transformed with At4g14560 and the results obtained using two independently isolated lines of transformed cells.

Cells transformed with At4g14560 were also analyzed in a similar manner. Similar to the above cases, the results show a decrease in the polysome fraction and an increase in the non-polysome fraction, which were induced by heat stress treatment at 37° C. for 10 minutes (FIG. 30A), consistency between the distribution of 28S rRNA and 18S rRNA in the sucrose density gradient solution and the behavior of the absorbance profile (FIG. 30B), maintenance of polysome formation by At4g14560 mRNA whose translation is maintained even under heat stress, and a shift of the mRNA of Act2 and At3g47610 susceptible to translational repression under heat stress to the non-polysome fraction (FIG. 30C). However, in contrast to the cells transformed with At3g47610 and the cells transformed with At5g39740, GUS mRNA that contains the 5' UTR of At4g14560 whose translation is maintained even under heat stress remained in the polysome fraction also under heat stress (FIG. 30C).

Cells Transformed with At1g77120

Figure 31:
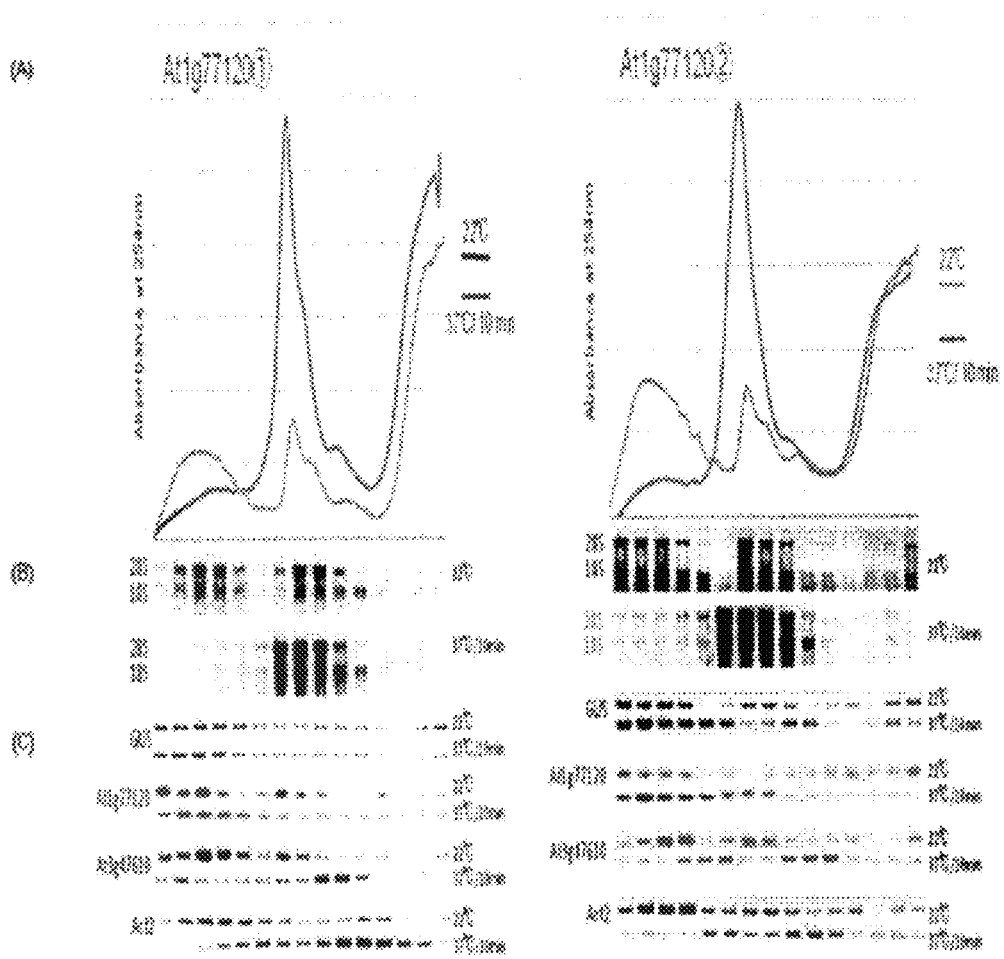
FIG. 31 shows the results from polysome/RT-PCR assay of cells transformed with At1g77120 and the results obtained using two independently isolated lines of transformed cells.

Cells transformed with At4g14560 were also analyzed in a similar manner. The results show a decrease in the polysome fraction and an increase in the non-polysome fraction, which were induced by heat stress treatment at 37° C. for 10 minutes (FIG. 31A), consistency between the distribution of 28S rRNA and 18S rRNA in the sucrose density gradient solution and the behavior of the absorbance profile (FIG. 31B), maintenance of polysome formation under heat stress by At1g77120 mRNA whose translation is maintained even under heat stress, and a shift of the mRNA of Act2 and At3g47610 susceptible to translational repression under heat stress to the non-polysome fraction (FIG. 31C). On the other hand, GUS mRNA that contains the 5' UTR of At1g77120 remained in the polysome fraction also under heat stress (FIG. 31C).

The results of the analysis using the cells transformed with At4g14560 and the cells transformed with At1g77120 showed that a foreign gene introduced into a plant can be expressed without repression even under heat stress, by utilizing the 5' UTR having the ability to maintain translation even under heat stress.

Cells Transformed with At4g14560+ and Cells Transformed with At1g77120+

Figure 32:
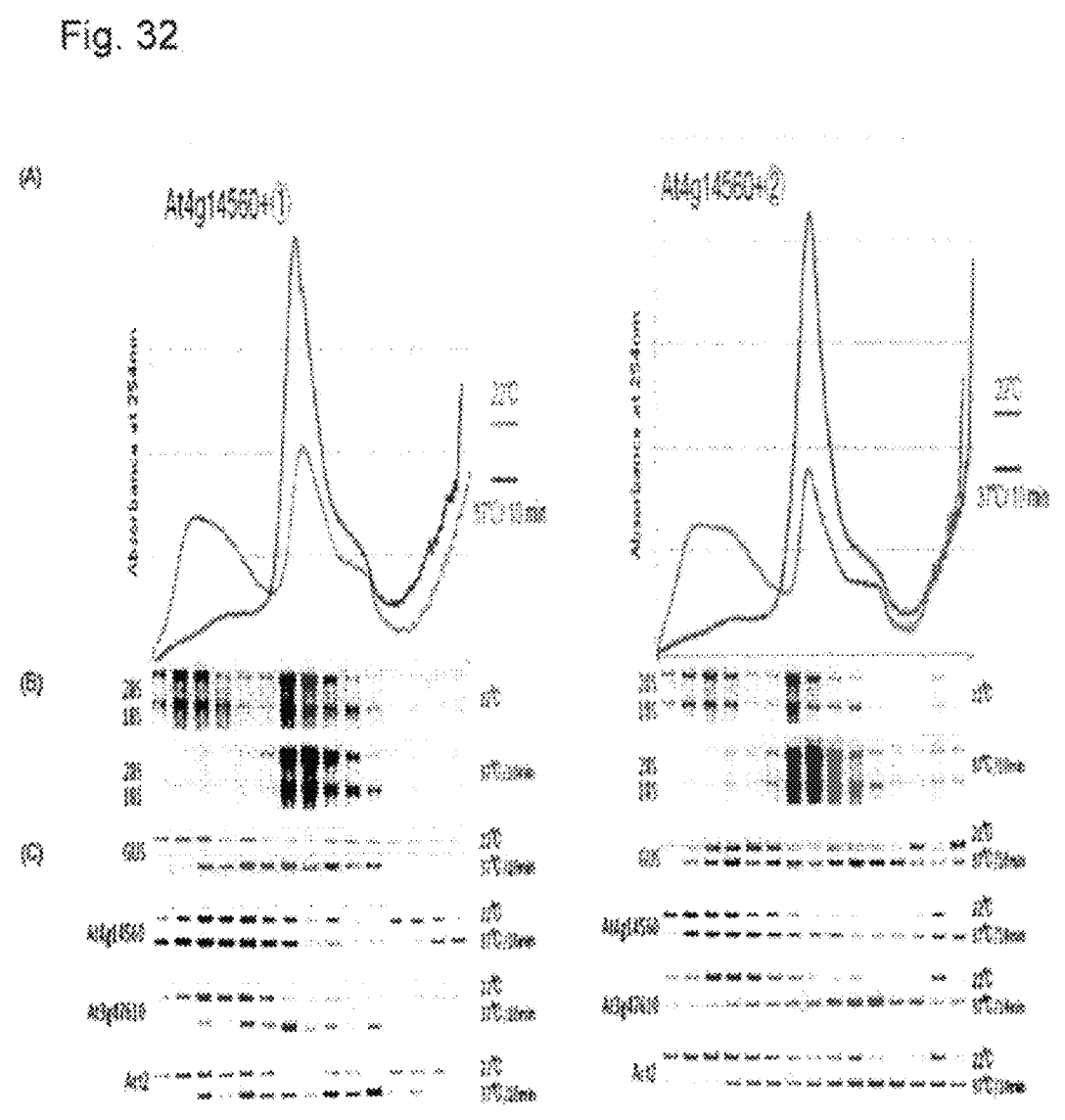
Figure 33:
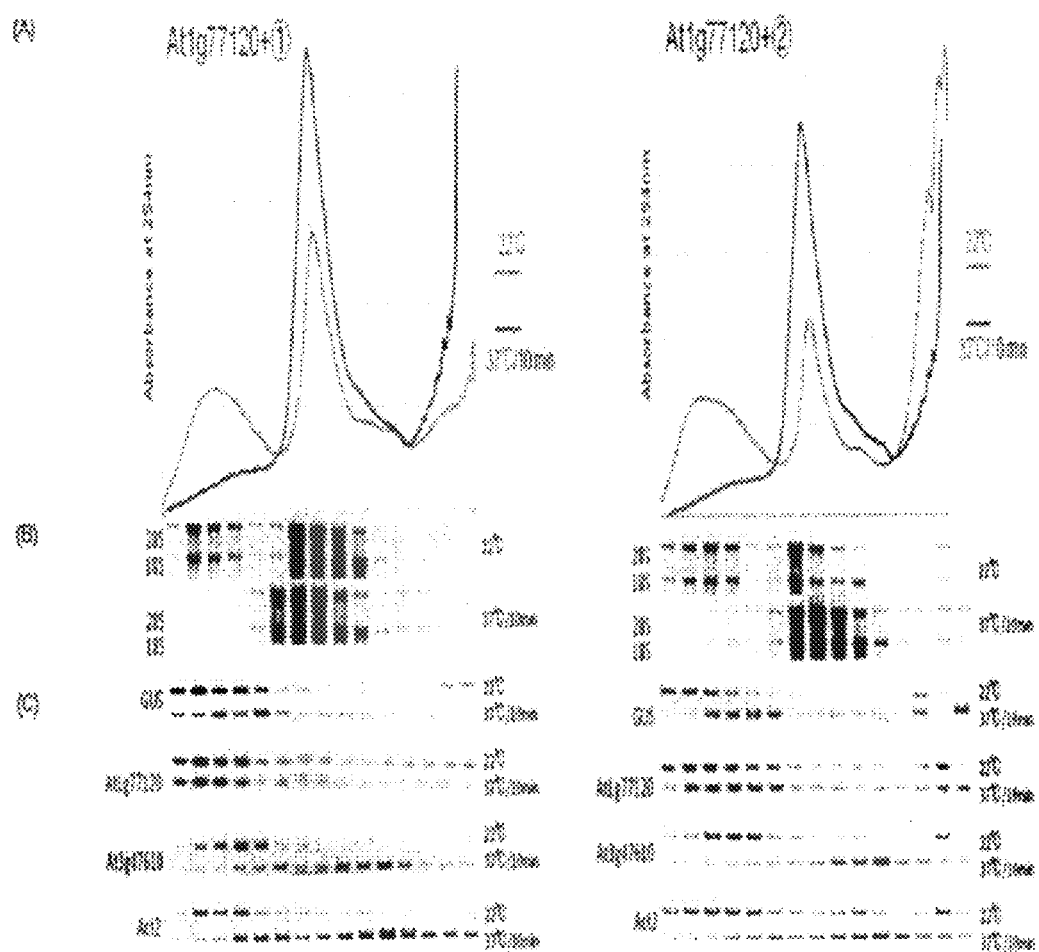
FIG. 33 shows the results from polysome/RT-PCR assay of cells transformed with At1g77120+ and the results obtained using two independently isolated lines of transformed cells.

The total of 4 types of transformed cells (two lines of the cells transformed with At4g14560+ and two lines of the cells transformed with At1g77120+) were used to analyze the behavior of GUS mRNA of the cells cultured under normal conditions (22° C.) and heat stress conditions (37° C./10 min.) by polysome/RT-PCR. As is the case with the analysis results obtained using the above-described 4 types of transformed cells, according to the results, the cells transformed with At4g14560+ and the cells transformed with At1g77120+, which contain an extra sequence, showed a decrease in the polysome fraction and an increase in the non-polysome fraction, which were induced by heat stress (FIGS. 32A and 33A), consistency between the distribution of 28S rRNA and 18S rRNA in the sucrose density gradient solution and the behavior of the absorbance profile (FIGS. 32B and 33B), maintenance of polysome formation by At4g14560 and At1g77120 mRNA whose translations are maintained even under heat stress, and a shift of the mRNA of Act2 and At3g47610 susceptible to translational repression under heat stress to the non-polysome fraction (FIGS. 32C and 33C). On the other hand, in the case of GUS mRNA to which the 5' UTR of At4g14560+5' was added, the distribution of GUS mRNA shifted to the non-polysome fraction by heat stress treatment (FIG. 32C), compared to GUS mRNA of the cells transformed with At4g14560 (FIG. 30C), although the degree of the shift was not as much as the case of GUS mRNA containing the 5' UTR of At3g47610 or At5g39740. Further, also in the case of the cells transformed with At1g77120+, it was confirmed that GUS mRNA containing the 5' UTR of At1g77120+ made a shift as a whole to the non-polysome fraction, compared to the cells transformed with At1g77120 (FIGS. 31C and 33C). These results are consistent with the results of the transient expression experiment performed in section 6-1. The results show that the ability to maintain translation under heat stress is impaired when an extra sequence is present at the 5' side of the 5' UTR. The results also suggest that consideration is needed to prevent an extra sequence from being added to the 5' UTR when constructing an expression vector.

Cells Transformed with At5g39740-S

Figure 34:
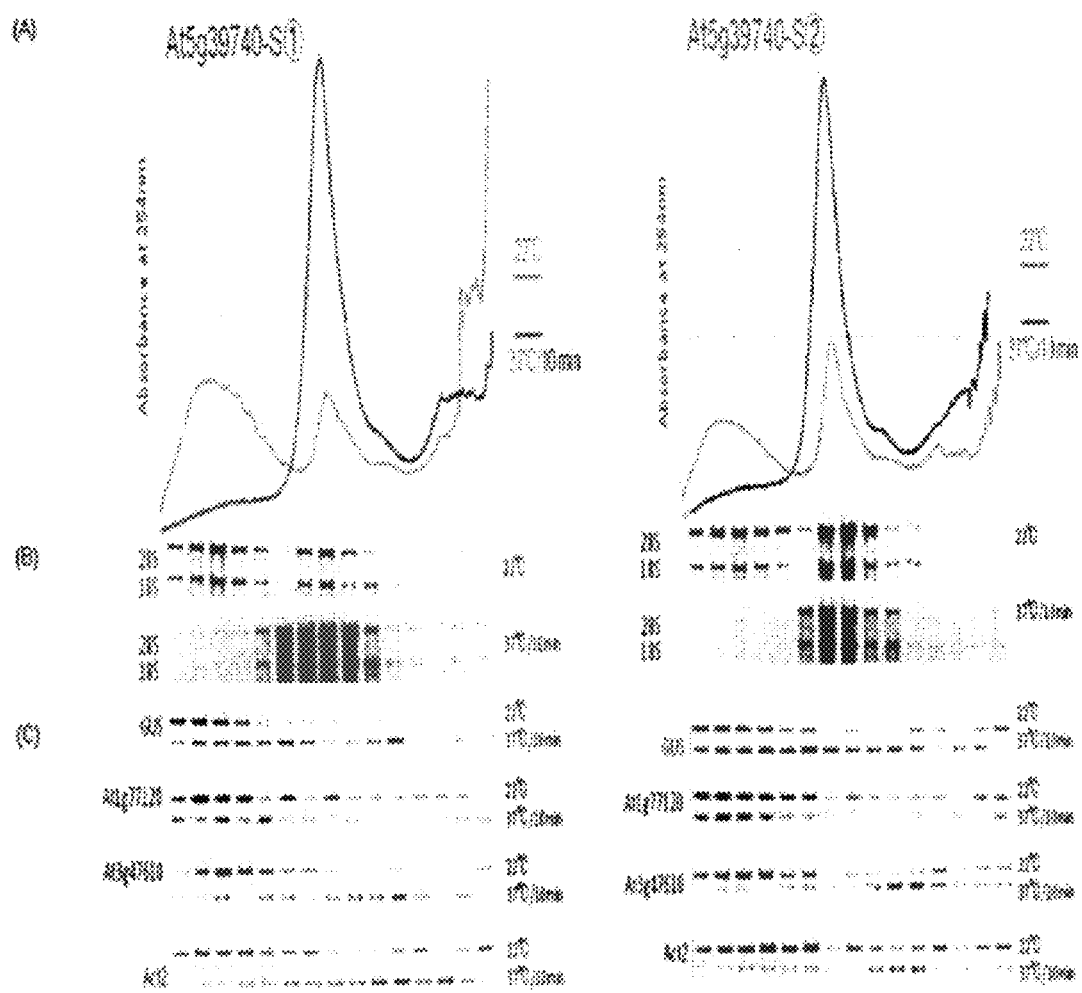
FIG. 34 shows the results from polysome/RT-PCR assay of cells transformed with At5g39740-S and the results obtained using two independently isolated lines of transformed cells.

A 5' UTR was produced by replacing the bases in the 5' UTR of At5g39740 whose translation is repressed under heat stress by the predicted optimal sequences (bases 1 to 7 from the 5' end: uuaaaaa (SEQ ID NO:7); and bases 12-32 from the 5' end: acaaaaaaaaaaaaaaaaaaaa (SEQ ID NO:8), see FIG. 20), and an expression vector that expresses this 5' UTR was constructed. The predicted optimal sequences were introduced into the 5' UTR of At5g39740 at the same positions shown in FIGS. 21-(e) and 22-(e). Cells transformed with At5g39740-S were transfected with the constructed binary vector, and the effect of the predicted optimal sequences was examined in a similar manner as the analysis of the above-described transformed cells. FIG. 34 shows the results.

The results show that the translation of GUS mRNA of cells transformed with At5g39740 is repressed under heat stress (FIG. 34C). On the other hand, in the case of GUS mRNA containing the 5' UTR of At5g39740-S prepared by replacing a portion of the 5' UTR of At5g39740 by the predicted optimal sequence, there was a decrease in the shift to the non-polysome fraction (FIG. 34C), compared to the results shown in FIG. 29C. This shows that replacement by the predicted optimal sequence improves the ability to maintain translation.

Salt Stress Treatment

The ability to maintain translation under salt stress was examined using the 5' UTRs (At4g14560 and At1g77120) whose translation is not repressed even under heat stress and the 5' UTR (At3g47610) whose translation is repressed. Specifically, polysome/RT-PCR assay was performed using the cells transformed with At4g14560, cells transformed with At1g77120, and cells transformed with At3g47610.

Figure 35:
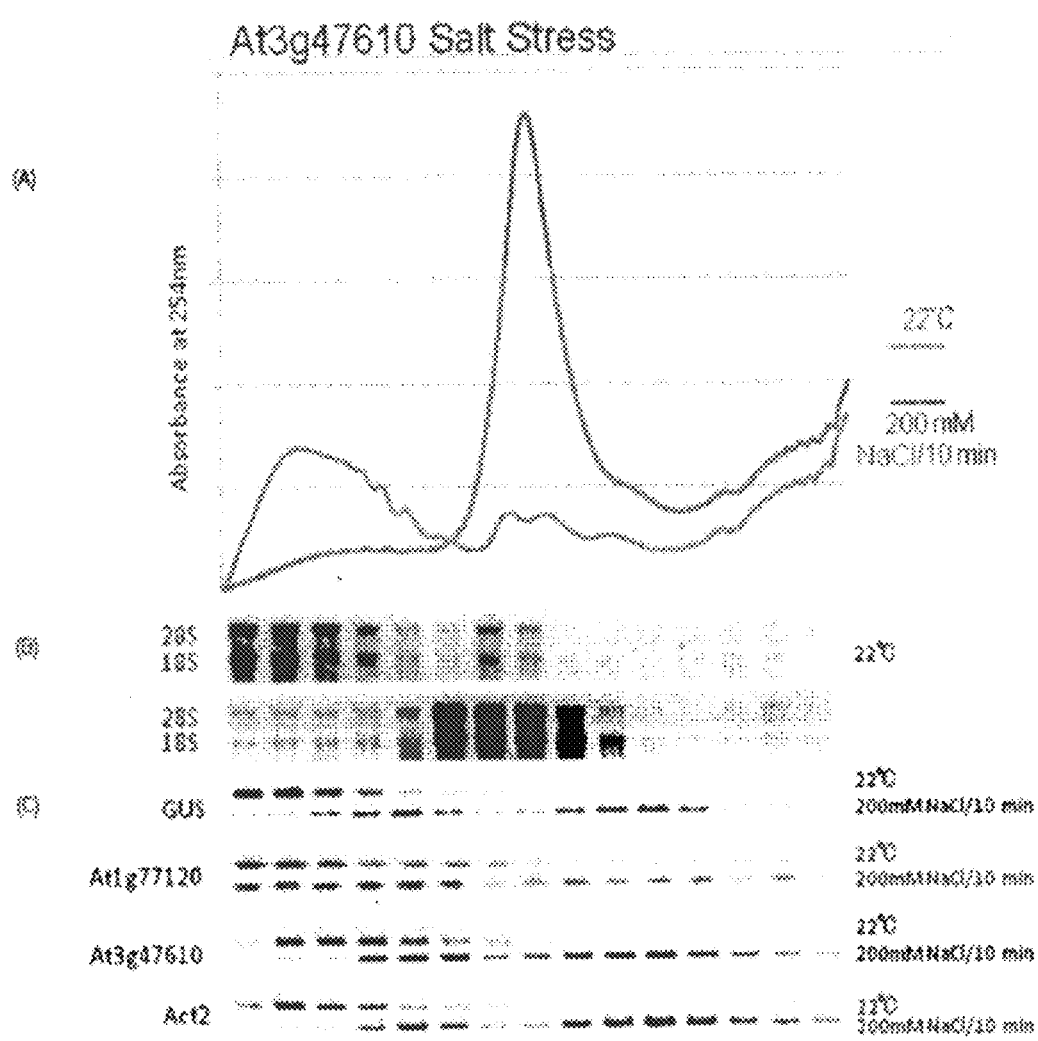
FIG. 35 shows the results from polysome/RT-PCR assay of cells transformed with At3g47610.
Figure 36:
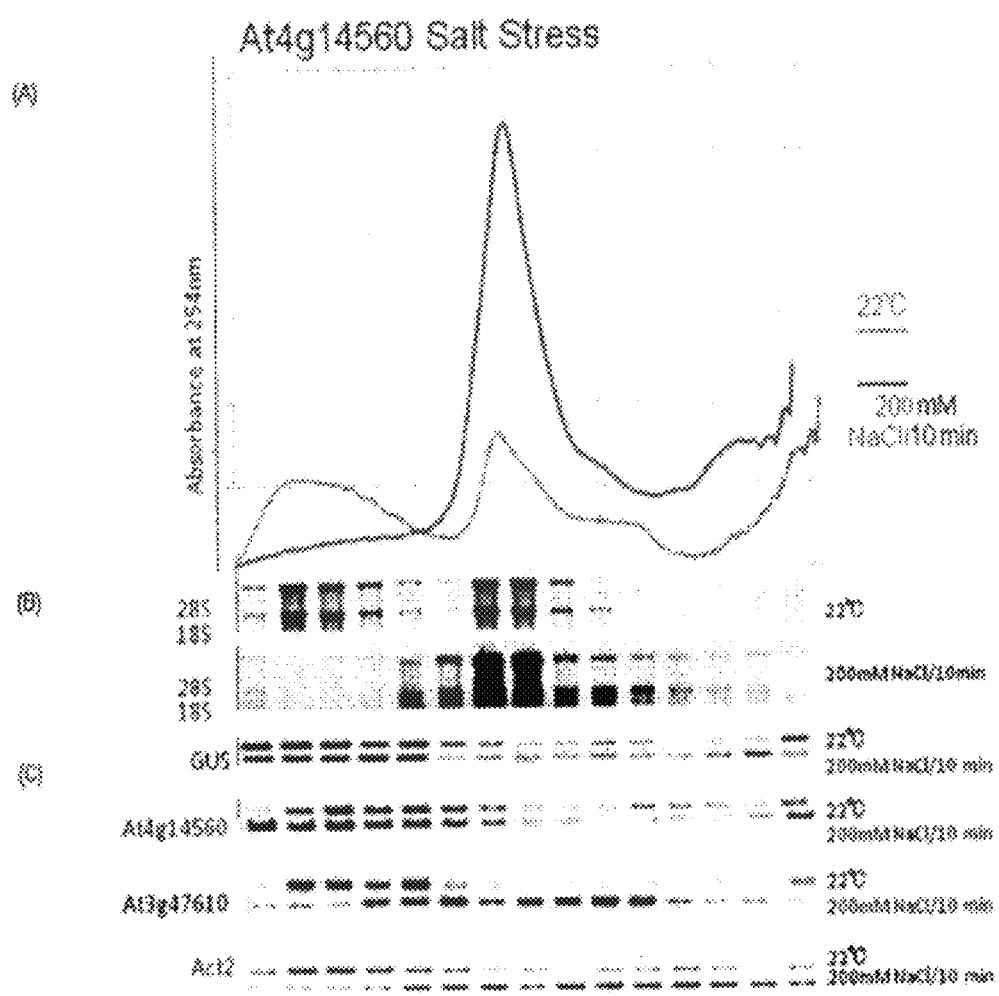
FIG. 36 shows the results from polysome/RT-PCR assay of cells transformed with At4g14560.
Figure 37:
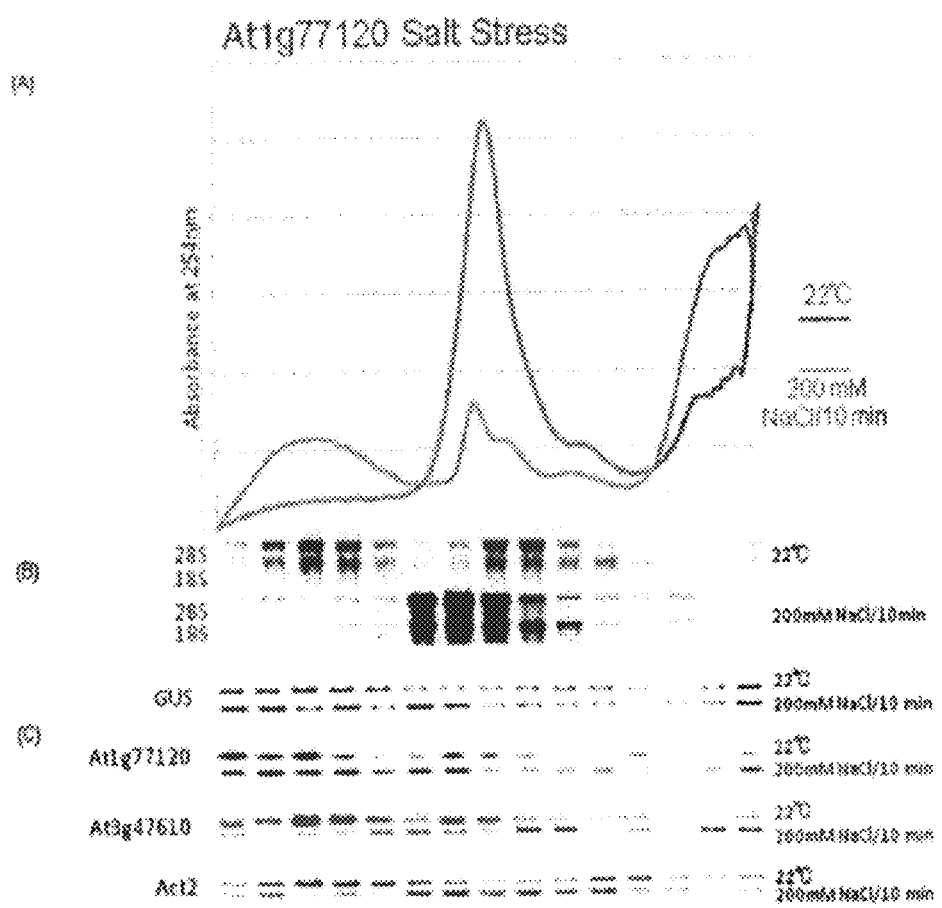
FIG. 37 shows the results from polysome/RT-PCR assay of cells transformed with At1g77120.

Similar to the results from heat stress treatment, salt treatment also resulted in a decrease in the polysome fraction and an increase in the non-polysome fraction of cells as a whole (FIGS. 35A, 36A, and 37A), and in consistency between the distribution of 28S rRNA and 18S rRNA in the sucrose density gradient solution and the behavior of the absorbance profile (FIGS. 35B, 36B, and 37B). Translation was inhibited by salt stress in a similar manner as it was by heat stress. Further, the mRNA of Act2 and At3g47610 susceptible to translational repression under heat stress shifted to the non-polysome fraction by salt stress treatment (FIGS. 35C, 36C, and 37C). Further, the translation of GUS mRNA containing the 5' UTR of At3g47610 was similarly repressed by salt stress (FIG. 35C). In contrast, GUS mRNA containing the 5' UTR of At4g14560 and GUS mRNA containing the 5' UTR of At1g77120 remained in the polysome fraction without being repressed even under salt stress (FIGS. 36C and 37C).

The above findings show that the 5' UTR of At4g14560 and the 5' UTR of At1g77120, which are capable of maintaining the translation at least under heat stress, demonstrate the ability to maintain translation even under salt stress, and that when the 5' UTR of At3g47610 whose translation is repressed under heat stress was used, the translation thereof was similarly repressed also under salt stress.

9 Measurement of GUS Activity

In the above-described polysome/RT-PCR assay, a short period of intense heat stress treatment (37° C./10 min.) was performed, and the translation ability of the 5' UTR was evaluated from changes in the state of polysome formation by mRNA. Herein, the transformed cells were exposed to heat stress for a long period of time, and changes in the accumulated amount of GUS proteins, which are translation products, were investigated to thereby examine the ability of each 5' UTR to maintain translation. When cells are cultured at 37° C. for a long period of time, transformed cells are destroyed. Therefore, in this examination, cells were cultured under lower heat stress (32° C.), as described below.

9-1 Stress Treatment of Stably Transformed Cells

Stably transformed cells on day 3 after subculture were cultured at 32° C. for 24 hours as heat stress treatment. The conditions other than that were the same as those described in section 8-1.

9-2 Measurement of GUS Activity

GUS activity was measured in accordance with the method of Jefferson et al. (Jefferson et al., 1987, EMBO J. 6, 3901-3907). Cultured cells were centrifuged (800 rpm, 1 min., 22° C.) to precipitate the cells. 300 µL of passive lysis buffer (Promega) was added thereto, and the cells were disrupted using Handy Sonic (Tomy Seiko Co., Ltd.). The disrupted cells were re-centrifuged (15,000 rpm, 5 min., 4° C.), and 200 µL of the supernatant was collected. 100 µL of the supernatant and 200 µL of 1.5 mM 4-methylumbelliferyl-β-D-glucuronide solution were mixed together for reaction. Subsequently, using a SpectraFluor (Tecan), the fluorescence intensity of the reaction product, 4-methyl-umbelliferone (4-MU), was measured at an excitation wavelength of 365 nm and at a fluorescence wavelength of 455 nm every minute for 30 minutes. The average of the blank was subtracted from the average of the increase in the measured value per minute in a period of 10 to 20 minutes to determine the average increase in 4-MU per minute. GUS activity was calculated as pmol/min/mg protein.

9-3 Measurement of the Total Amount of Proteins by Bradford Method

The total amount of proteins was measured in accordance with the method of Bradford (Bradford, M., 1976, Anal. Biochem. 72, 248-254). 500 µL of protein quantitation reagent was added to 10 µL of protein solution, and the amount was measured using a SpectraFluor (Tecan). The protein concentration was determined from the standard curve created using BSA of a known concentration.

Figure 38:
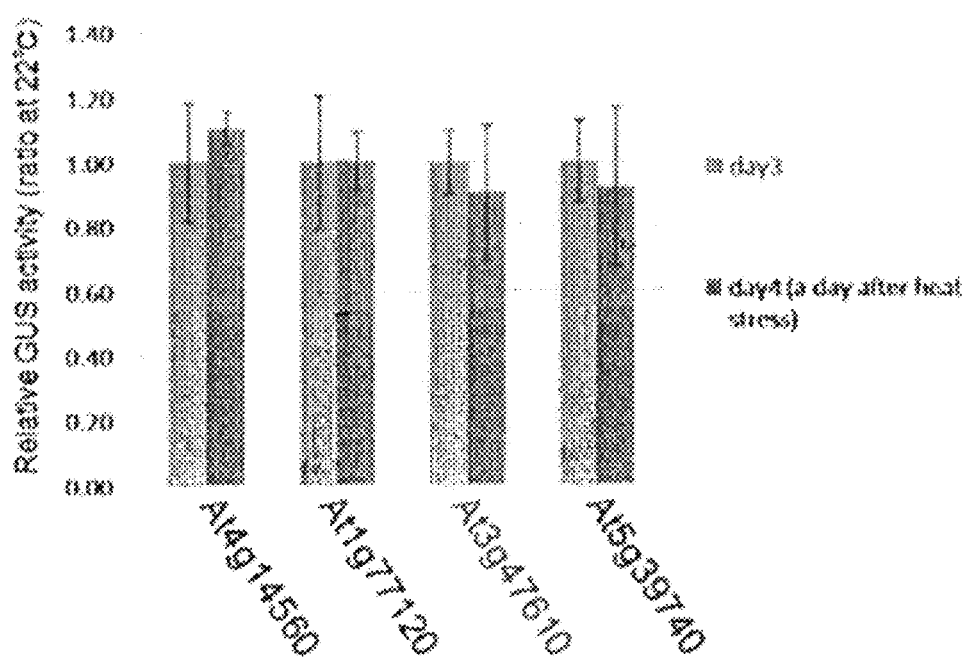
FIG. 38 For FIG. 38, transformed cells were cultured under normal conditions for 3 days and subsequently under heat stress conditions (32° C. for 24 hours). The figure shows a graph of the relative GUS activity level on day 4 when the activity level on day 3 is assumed to be 1. The culture conditions and the number of measurements are as described below: after normal subculture procedures, each transformed cell was cultured under normal conditions (22° C. for 3 days), followed by collection. After culturing the remaining culture medium at 32° C. for 24 hours, the cells were collected again. A crude protein solution was prepared from the isolated cells, and GUS activity per protein amount was measured. The activity was measured 4 or 5 times. The figure shows the averages and standard errors of GUS activity.

Protein quantitation reagent
Coomassie brilliant blue G-250 100 mg/L
95% ethanol 50 mL/L
85% (w/v) phosphoric acid 100 mL/L 9-4 Results The transformed cells transfected with the 5' UTRs from the genes (At4g14560 and At1g77120) having the ability to maintain translation under heat stress conditions at 32° C. for 24 hours showed a tendency to maintain the accumulated amount of GUS proteins (FIG. 38). In contrast, the cells transformed with the 5' UTRs from genes (At3g47610 and At5g39740) susceptible to translational repression showed a tendency of a decrease in the accumulated amount of GUS proteins by a long period of exposure to mild heat stress (32° C. for 24 hours) (FIG. 38).

This shows that the 5' UTRs of these genes have the ability to maintain translation, and that, by allowing genes encoding mRNA containing these 5' UTRs to be expressed in cells and subjecting the cells to heat stress, it is possible to preferentially produce proteins encoded by these genes.

SEQUENCE LISTING

The invention claimed is:

1. A recombinant DNA molecule comprising a heterologous promoter operably linked to a nucleotide sequence encoding an mRNA molecule, wherein bases 1 to 7 and bases 12 to 32 from the 5' end of said mRNA molecule are bases 1 to 7 and 12 to 32 of SEQ ID NO:6, respectively, wherein the nucleotide sequence encoding the mRNA molecule is directly ligated to within 3 nucleotides of transcription initiation point of said promoter.

2. The recombinant DNA molecule of claim 1, wherein the mRNA molecule comprises SEQ ID NO:6.

3. A vector comprising a nucleic acid coding sequence operably linked to the recombinant DNA molecule of claim 1.

4. A transformant transformed with the vector as defined in claim 3.

5. The transformant as define in claim 4, wherein the transformant is a transgenic plant.

6. A method for producing a protein comprising growing the transformant as defined in claim 5 under at least one environmental stress selected from the group consisting of heat stress and salt stress.

7. A method for producing a plant comprising introducing the vector as defined in claim 3 into a plant, wherein the plant is capable of escaping translational repression of the sequence encoded by the nucleic acid coding sequence that is induced by at least one environmental stress selected from the group consisting of heat stress and salt stress in plants not transformed with said vector.

8. A method for producing a recombinant DNA molecule, the method comprising: directly ligating the 5' end of a sequence encoding an mRNA molecule to within 3 nucleotides of transcription initiation point of a heterologous promoter and operably linking the 3' end of the sequence encoding said mRNA molecule to a nucleic acid coding sequence wherein bases 1 to 7 and bases 12 to 32 from the 5' end of said mRNA molecule are bases 1 to 7 and 12 to 32 of SEQ ID NO:6, respectively, and wherein the recombinant DNA molecule is capable of escaping translational repression induced by at least one environmental stress selected from the group consisting of heat stress and salt stress.

9. A method for escaping translational repression of a protein encoded by a recombinant DNA induced by at least one environmental stress selected from the group consisting of heat stress and salt stress, the method comprising: producing the vector of claim 3 and transforming a host with said vector, wherein the promoter is functional in a plant.

10. The vector of claim 3, wherein the mRNA molecule comprises SEQ ID NO:6.

11. The vector as defined in claim 3, wherein the promoter is CaMV35S promoter.

12. The method as defined in claim 9, wherein the promoter is CaMV35S promoter.

* * * * *

SEQUENCE LISTING

<160> NUMBER OF SEQ ID NOS: 90

<210> SEQ ID NO 1
<211> LENGTH: 7
<212> TYPE: RNA
<213> ORGANISM: Arabidopsis thaliana

<400> SEQUENCE: 1 acacaag                                                                  7

<210> SEQ ID NO 2

```
<211> LENGTH: 7
<212> TYPE: RNA
<213> ORGANISM: Arabidopsis thaliana

<400> SEQUENCE: 2 auaacac                                                                    7

<210> SEQ ID NO 3
<211> LENGTH: 7
<212> TYPE: RNA
<213> ORGANISM: Arabidopsis thaliana

<400> SEQUENCE: 3 uacauca                                                                    7

<210> SEQ ID NO 4
<211> LENGTH: 117
<212> TYPE: RNA
<213> ORGANISM: Arabidopsis thaliana

<400> SEQUENCE: 4
acacaagcau uuucaaggau aucaaaucac aaucccaaga agagcaauaa caagagaaga         60
agaaguaguu caagaauuaa ggaagagagc uucuccguua aaguauagug agagaau          117

<210> SEQ ID NO 5
<211> LENGTH: 47
<212> TYPE: RNA
<213> ORGANISM: Arabidopsis thaliana

<400> SEQUENCE: 5
auaacacauu ucaagcauug gauuaaucaa agacaaagaa aacgaaa                      47

<210> SEQ ID NO 6
<211> LENGTH: 58
<212> TYPE: RNA
<213> ORGANISM: Arabidopsis thaliana

<400> SEQUENCE: 6
uacaucacaa ucacacaaaa cuaacaaaag aucaaaagca aguucuucac uguugaua          58

<210> SEQ ID NO 7
<211> LENGTH: 7
<212> TYPE: RNA
<213> ORGANISM: Artificial Sequence
<220> FEATURE:
<223> OTHER INFORMATION: Synthetic predicted sequence

<400> SEQUENCE: 7 uuaaaaa                                                                    7

<210> SEQ ID NO 8
<211> LENGTH: 21
<212> TYPE: RNA
<213> ORGANISM: Artificial Sequence
<220> FEATURE:
<223> OTHER INFORMATION: Synthetic predicted sequence

<400> SEQUENCE: 8
acaaaaaaaa aaaaaaaaaa a                                                   21

<210> SEQ ID NO 9
<211> LENGTH: 40
<212> TYPE: DNA
<213> ORGANISM: Artificial Sequence
```

```
<220> FEATURE:
<223> OTHER INFORMATION: Synthetic promoter

<400> SEQUENCE: 9
gcgcgcaatt aaccctcact aaaggtctag aggatccatg                                40

<210> SEQ ID NO 10
<211> LENGTH: 27
<212> TYPE: DNA
<213> ORGANISM: Artificial Sequence
<220> FEATURE:
<223> OTHER INFORMATION: Synthetic restriction enzyme site

<400> SEQUENCE: 10
gcgcgcatcg atgaattcac tagttta                                             27

<210> SEQ ID NO 11
<211> LENGTH: 60
<212> TYPE: DNA
<213> ORGANISM: Artificial Sequence
<220> FEATURE:
<223> OTHER INFORMATION: Synthetic polyA site

<400> SEQUENCE: 11
aattcaaaaa aaaaaaaaaa aaaaaaaaaa aaaaaaaaaa aaaaaaaaaa aaaatattat         60

<210> SEQ ID NO 12
<211> LENGTH: 58
<212> TYPE: DNA
<213> ORGANISM: Artificial Sequence
<220> FEATURE:
<223> OTHER INFORMATION: Synthetic polyA site

<400> SEQUENCE: 12
cgataatatt ttttttttt tttttttttt tttttttttt tttttttttt tttttttg           58

<210> SEQ ID NO 13
<211> LENGTH: 30
<212> TYPE: RNA
<213> ORGANISM: Arabidopsis thaliana

<400> SEQUENCE: 13
augcauauaa aauagaucug ucgguccugu                                          30

<210> SEQ ID NO 14
<211> LENGTH: 23
<212> TYPE: RNA
<213> ORGANISM: Arabidopsis thaliana

<400> SEQUENCE: 14
gcgauuggag accauaacug cug                                                 23

<210> SEQ ID NO 15
<211> LENGTH: 24
<212> TYPE: RNA
<213> ORGANISM: Arabidopsis thaliana

<400> SEQUENCE: 15
aaaucauuau uaaagaaaua cccc                                                24

<210> SEQ ID NO 16
<211> LENGTH: 117
<212> TYPE: RNA
<213> ORGANISM: Arabidopsis thaliana
```

```
<400> SEQUENCE: 16
acacaagcau uuucaaggau aucaaaucac aaucccaaga agagcaauaa caagagaaga    60
agaaguaguu caagaauuaa ggaagagagc uucuccguua aaguauagug agagaau      117

<210> SEQ ID NO 17
<211> LENGTH: 117
<212> TYPE: RNA
<213> ORGANISM: Artificial Sequence
<220> FEATURE:
<223> OTHER INFORMATION: Synthetic modified sequence

<400> SEQUENCE: 17
ccuuucucau uuucaaggau aucaaaucac aaucccaaga agagcaauaa caagagaaga    60
agaaguaguu caagaauuaa ggaagagagc uucuccguua aaguauagug agagaau      117

<210> SEQ ID NO 18
<211> LENGTH: 57
<212> TYPE: RNA
<213> ORGANISM: Arabidopsis thaliana

<400> SEQUENCE: 18
ccuuucuugu cgucguuucg aagagacuaa aggcgacgga gagaaucgga gaagaag        57

<210> SEQ ID NO 19
<211> LENGTH: 57
<212> TYPE: RNA
<213> ORGANISM: Artificial Sequence
<220> FEATURE:
<223> OTHER INFORMATION: Synthetic modified sequence

<400> SEQUENCE: 19
acacaagugu cgucguuucg aagagacuaa aggcgacgga gagaaucgga gaagaag        57

<210> SEQ ID NO 20
<211> LENGTH: 47
<212> TYPE: RNA
<213> ORGANISM: Arabidopsis thaliana

<400> SEQUENCE: 20
auaacacauu ucaagcauug gauuaaucaa agacaaagaa aacgaaa                    47

<210> SEQ ID NO 21
<211> LENGTH: 47
<212> TYPE: RNA
<213> ORGANISM: Artificial Sequence
<220> FEATURE:
<223> OTHER INFORMATION: Synthetic modified sequence

<400> SEQUENCE: 21
gguucguauu ucaagcauug gauuaaucaa agacaaagaa aacgaaa                    47

<210> SEQ ID NO 22
<211> LENGTH: 29
<212> TYPE: RNA
<213> ORGANISM: Arabidopsis thaliana

<400> SEQUENCE: 22
gguucgucgu uaucgguauc gaaucaaca                                         29

<210> SEQ ID NO 23
<211> LENGTH: 29
<212> TYPE: RNA
<213> ORGANISM: Artificial Sequence
```

```
<220> FEATURE:
<223> OTHER INFORMATION: Synthetic modified sequence

<400> SEQUENCE: 23
auaacaccgu uaucgguauc gaaucaaca                                29

<210> SEQ ID NO 24
<211> LENGTH: 58
<212> TYPE: RNA
<213> ORGANISM: Arabidopsis thaliana

<400> SEQUENCE: 24
uacaucacaa ucacacaaaa cuaacaaaag aucaaaagca aguucuucac uguugaua    58

<210> SEQ ID NO 25
<211> LENGTH: 58
<212> TYPE: RNA
<213> ORGANISM: Artificial Sequence
<220> FEATURE:
<223> OTHER INFORMATION: Synthetic modified sequence

<400> SEQUENCE: 25
ccuuucucaa ucacacaaaa cuaacaaaag aucaaaagca aguucuucac uguugaua    58

<210> SEQ ID NO 26
<211> LENGTH: 57
<212> TYPE: RNA
<213> ORGANISM: Arabidopsis thaliana

<400> SEQUENCE: 26
ccuuucuugu cgucguuucg aagagacuaa aggcgacgga gagaaucgga gaagaag     57

<210> SEQ ID NO 27
<211> LENGTH: 57
<212> TYPE: RNA
<213> ORGANISM: Artificial Sequence
<220> FEATURE:
<223> OTHER INFORMATION: Synthetic modified sequence

<400> SEQUENCE: 27
uacaucaugu cgucguuucg aagagacuaa aggcgacgga gagaaucgga gaagaag     57

<210> SEQ ID NO 28
<211> LENGTH: 47
<212> TYPE: RNA
<213> ORGANISM: Arabidopsis thaliana

<400> SEQUENCE: 28
auaacacauu ucaagcauug gauuaaucaa agacaaagaa aacgaaa                47

<210> SEQ ID NO 29
<211> LENGTH: 47
<212> TYPE: RNA
<213> ORGANISM: Artificial Sequence
<220> FEATURE:
<223> OTHER INFORMATION: Synthetic modified sequence

<400> SEQUENCE: 29
gguucguauu ucaagcauug gauuaaucaa agacaaagaa aacgaaa                47

<210> SEQ ID NO 30
<211> LENGTH: 47
<212> TYPE: RNA
<213> ORGANISM: Artificial Sequence
<220> FEATURE:
```

<223> OTHER INFORMATION: Synthetic modified sequence

<400> SEQUENCE: 30
auaacacauu ucaucuuuug ucacucaucu ucacaaagaa aacgaaa         47

<210> SEQ ID NO 31
<211> LENGTH: 47
<212> TYPE: RNA
<213> ORGANISM: Artificial Sequence
<220> FEATURE:
<223> OTHER INFORMATION: Synthetic modified sequence

<400> SEQUENCE: 31
gcgccucauu ucaucuuuug ucacucaucu ucacaaagaa aacgaaa         47

<210> SEQ ID NO 32
<211> LENGTH: 42
<212> TYPE: RNA
<213> ORGANISM: Arabidopsis thaliana

<400> SEQUENCE: 32
gcgccucuug ccaucuuuug ucacucaucu ucacaggaaa ca              42

<210> SEQ ID NO 33
<211> LENGTH: 42
<212> TYPE: RNA
<213> ORGANISM: Artificial Sequence
<220> FEATURE:
<223> OTHER INFORMATION: Synthetic modified sequence

<400> SEQUENCE: 33
auaacacuug ccaucuuuug ucacucaucu ucacaggaaa ca              42

<210> SEQ ID NO 34
<211> LENGTH: 42
<212> TYPE: RNA
<213> ORGANISM: Artificial Sequence
<220> FEATURE:
<223> OTHER INFORMATION: Synthetic modified sequence

<400> SEQUENCE: 34
gcgccucuug ccaagcauug gauuaaucaa agacaggaaa ca              42

<210> SEQ ID NO 35
<211> LENGTH: 42
<212> TYPE: RNA
<213> ORGANISM: Artificial Sequence
<220> FEATURE:
<223> OTHER INFORMATION: Synthetic modified sequence

<400> SEQUENCE: 35
auaacacuug ccaagcauug gauuaaucaa agacaggaaa ca              42

<210> SEQ ID NO 36
<211> LENGTH: 210
<212> TYPE: RNA
<213> ORGANISM: Arabidopsis thaliana

<400> SEQUENCE: 36
auuaacaaac aaaccgaaaa aagaaaaaaa cucaucuuuc uccaaaauca cacaaaucuu    60
cuuuauuugu uauucucaau ccuuccuuca uccccagguu ucuuucgauu cguugaguca    120
uucaauuuuu ccaucacugg guuuuucucu cugaauccga ucggagaauc cagucgauua    180
cuaaucuagc gcucucuuuu uuucuacucg                                    210

```
<210> SEQ ID NO 37
<211> LENGTH: 210
<212> TYPE: RNA
<213> ORGANISM: Artificial Sequence
<220> FEATURE:
<223> OTHER INFORMATION: Synthetic modified sequence

<400> SEQUENCE: 37
ccuucucaac aaaccgaaaa aagaaaaaaa cucaucuuuc uccaaaauca cacaaaucuu      60
cuuuauuugu uauucucaau ccuuccuuca uccccagguu ucuuucgauu cguugaguca     120
uucaauuuuu ccaucacugg guuuuucucu cugaauccga ucggagaauc cagucgauua     180
cuaaucuagc gcucucuuuu uuucuacucg                                      210

<210> SEQ ID NO 38
<211> LENGTH: 210
<212> TYPE: RNA
<213> ORGANISM: Artificial Sequence
<220> FEATURE:
<223> OTHER INFORMATION: Synthetic modified sequence

<400> SEQUENCE: 38
auuaacaaac auaaguuaca ucucucgugu uucaucuuuc uccaaaauca cacaaaucuu      60
cuuuauuugu uauucucaau ccuuccuuca uccccagguu ucuuucgauu cguugaguca     120
uucaauuuuu ccaucacugg guuuuucucu cugaauccga ucggagaauc cagucgauua     180
cuaaucuagc gcucucuuuu uuucuacucg                                      210

<210> SEQ ID NO 39
<211> LENGTH: 210
<212> TYPE: RNA
<213> ORGANISM: Artificial Sequence
<220> FEATURE:
<223> OTHER INFORMATION: Synthetic modified sequence

<400> SEQUENCE: 39
ccuucucaac auaaguuaca ucucucgugu uucaucuuuc uccaaaauca cacaaaucuu      60
cuuuauuugu uauucucaau ccuuccuuca uccccagguu ucuuucgauu cguugaguca     120
uucaauuuuu ccaucacugg guuuuucucu cugaauccga ucggagaauc cagucgauua     180
cuaaucuagc gcucucuuuu uuucuacucg                                      210

<210> SEQ ID NO 40
<211> LENGTH: 198
<212> TYPE: RNA
<213> ORGANISM: Arabidopsis thaliana

<400> SEQUENCE: 40
ccuucuccac auaaguuaca ucucucgugu uuuguuuucu uugucuccga uuuuuucgc       60 gacgaagaag aagacgagag auagagagag aaguagagaa aucgaaggaa ucuguaaccg     120
auuuuaagau cucaauuuuu aggguuguug auuuuucaau uucgggguua auuuuuuua      180 ggguuuucau uuggaauc                                                   198

<210> SEQ ID NO 41
<211> LENGTH: 198
<212> TYPE: RNA
<213> ORGANISM: Artificial Sequence
<220> FEATURE:
<223> OTHER INFORMATION: Synthetic modified sequence
```

<400> SEQUENCE: 41
auuaacacac auaaguuaca ucucucgugu uuuguuuucu uugucuccga uuuuuuucgc    60
gacgaagaag aagacgagag auagagagag aaguagagaa aucgaaggaa ucuguaaccg   120
auuuuaagau cucaauuuuu aggguuguug auuuuucaau uucuggguua auuuuuuua    180 ggguuuucau uuggaauc                                                 198

<210> SEQ ID NO 42
<211> LENGTH: 198
<212> TYPE: RNA
<213> ORGANISM: Artificial Sequence
<220> FEATURE:
<223> OTHER INFORMATION: Synthetic modified sequence

<400> SEQUENCE: 42
ccuucuccac aaaccgaaaa aagaaaaaaa cuuguuuucu uugucuccga uuuuuuucgc    60
gacgaagaag aagacgagag auagagagag aaguagagaa aucgaaggaa ucuguaaccg   120
auuuuaagau cucaauuuuu aggguuguug auuuuucaau uucuggguua auuuuuuua    180 ggguuuucau uuggaauc                                                 198

<210> SEQ ID NO 43
<211> LENGTH: 198
<212> TYPE: RNA
<213> ORGANISM: Artificial Sequence
<220> FEATURE:
<223> OTHER INFORMATION: Synthetic modified sequence

<400> SEQUENCE: 43
auuaacacac aaaccgaaaa aagaaaaaaa cuuguuuucu uugucuccga uuuuuuucgc    60
gacgaagaag aagacgagag auagagagag aaguagagaa aucgaaggaa ucuguaaccg   120
auuuuaagau cucaauuuuu aggguuguug auuuuucaau uucuggguua auuuuuuua    180 ggguuuucau uuggaauc                                                 198

<210> SEQ ID NO 44
<211> LENGTH: 42
<212> TYPE: RNA
<213> ORGANISM: Arabidopsis thaliana

<400> SEQUENCE: 44
gcgccucuug ccaucuuuug ucacucaucu ucacaggaaa ca                      42

<210> SEQ ID NO 45
<211> LENGTH: 42
<212> TYPE: RNA
<213> ORGANISM: Artificial Sequence
<220> FEATURE:
<223> OTHER INFORMATION: Synthetic modified sequence

<400> SEQUENCE: 45
auaacacuug ccaagcauug gauuaaucaa agacaggaaa ca                      42

<210> SEQ ID NO 46
<211> LENGTH: 42
<212> TYPE: RNA
<213> ORGANISM: Artificial Sequence
<220> FEATURE:
<223> OTHER INFORMATION: Synthetic modified sequence

<400> SEQUENCE: 46
gcgccauaac acaucucaag cauuggauua aucaaagaaa ca                      42

<210> SEQ ID NO 47
<211> LENGTH: 42
<212> TYPE: RNA
<213> ORGANISM: Artificial Sequence
<220> FEATURE:
<223> OTHER INFORMATION: Synthetic modified sequence

<400> SEQUENCE: 47
gcgccucuug auaacacuug ucaagcauug gauuaaucaa ag         42

<210> SEQ ID NO 48
<211> LENGTH: 42
<212> TYPE: RNA
<213> ORGANISM: Arabidopsis thaliana

<400> SEQUENCE: 48
gcgccucuug ccaucuuuug ucacucaucu ucacaggaaa ca         42

<210> SEQ ID NO 49
<211> LENGTH: 42
<212> TYPE: RNA
<213> ORGANISM: Artificial Sequence
<220> FEATURE:
<223> OTHER INFORMATION: Synthetic modified sequence

<400> SEQUENCE: 49
auaacacuug ccaagcauug gauuaaucaa agacaggaaa ca         42

<210> SEQ ID NO 50
<211> LENGTH: 42
<212> TYPE: RNA
<213> ORGANISM: Artificial Sequence
<220> FEATURE:
<223> OTHER INFORMATION: Synthetic modified sequence

<400> SEQUENCE: 50
uuaaaaauug ccaucuuuug ucacucaucu ucacaggaaa ca         42

<210> SEQ ID NO 51
<211> LENGTH: 42
<212> TYPE: RNA
<213> ORGANISM: Artificial Sequence
<220> FEATURE:
<223> OTHER INFORMATION: Synthetic modified sequence

<400> SEQUENCE: 51
gcgccucuug cacaaaaaaa aaaaaaaaaa aaacaggaaa ca         42

<210> SEQ ID NO 52
<211> LENGTH: 42
<212> TYPE: RNA
<213> ORGANISM: Artificial Sequence
<220> FEATURE:
<223> OTHER INFORMATION: Synthetic modified sequence

<400> SEQUENCE: 52
uuaaaaauug cacaaaaaaa aaaaaaaaaa aaacaggaaa ca         42

<210> SEQ ID NO 53
<211> LENGTH: 198
<212> TYPE: RNA
<213> ORGANISM: Arabidopsis thaliana

<400> SEQUENCE: 53

```
ccuucuccac auaaguuaca ucucucgugu uuuguuuucu uugucuccga uuuuuuucgc    60
gacgaagaag aagacgagag auagagagag aaguagagaa aucgaaggaa ucuguaaccg   120
auuuuaagau cucaauuuuu agguuguug auuuucaau uucugggua auuuuuuua      180 ggguuuucau uuggaauc                                                 198

<210> SEQ ID NO 54
<211> LENGTH: 198
<212> TYPE: RNA
<213> ORGANISM: Artificial Sequence
<220> FEATURE:
<223> OTHER INFORMATION: Synthetic modified sequence

<400> SEQUENCE: 54
auuaacacac aaaccgaaaa aagaaaaaaa cuuguuuucu uugucuccga uuuuuuucgc    60
gacgaagaag aagacgagag auagagagag aaguagagaa aucgaaggaa ucuguaaccg   120
auuuuaagau cucaauuuuu agguuguug auuuucaau uucugggua auuuuuuua      180 ggguuuucau uuggaauc                                                 198

<210> SEQ ID NO 55
<211> LENGTH: 198
<212> TYPE: RNA
<213> ORGANISM: Artificial Sequence
<220> FEATURE:
<223> OTHER INFORMATION: Synthetic modified sequence

<400> SEQUENCE: 55
uuaaaaacac auaaguuaca ucucucgugu uuuguuuucu uugucuccga uuuuuuucgc    60
gacgaagaag aagacgagag auagagagag aaguagagaa aucgaaggaa ucuguaaccg   120
auuuuaagau cucaauuuuu agguuguug auuuucaau uucugggua auuuuuuua      180 ggguuuucau uuggaauc                                                 198

<210> SEQ ID NO 56
<211> LENGTH: 198
<212> TYPE: RNA
<213> ORGANISM: Artificial Sequence
<220> FEATURE:
<223> OTHER INFORMATION: Synthetic modified sequence

<400> SEQUENCE: 56
ccuucuccac aacaaaaaaa aaaaaaaaaa aaaguuuucu uugucuccga uuuuuuucgc    60
gacgaagaag aagacgagag auagagagag aaguagagaa aucgaaggaa ucuguaaccg   120
auuuuaagau cucaauuuuu agguuguug auuuucaau uucugggua auuuuuuua      180 ggguuuucau uuggaauc                                                 198

<210> SEQ ID NO 57
<211> LENGTH: 198
<212> TYPE: RNA
<213> ORGANISM: Artificial Sequence
<220> FEATURE:
<223> OTHER INFORMATION: Synthetic modified sequence

<400> SEQUENCE: 57
uuaaaaacac aacaaaaaaa aaaaaaaaaa aaaguuuucu uugucuccga uuuuuuucgc    60
gacgaagaag aagacgagag auagagagag aaguagagaa aucgaaggaa ucuguaaccg   120
auuuuaagau cucaauuuuu agguuguug auuuucaau uucugggua auuuuuuua      180 ggguuuucau uuggaauc                                                 198
```

<210> SEQ ID NO 58
<211> LENGTH: 74
<212> TYPE: RNA
<213> ORGANISM: Artificial Sequence
<220> FEATURE:
<223> OTHER INFORMATION: Synthetic 5'UTR

<400> SEQUENCE: 58 cacggggac ucuagauaca ucacaaucac acaaaacuaa caaaagauca aaagcaaguu    60
cuucacuguu gaua                                                    74

<210> SEQ ID NO 59
<211> LENGTH: 58
<212> TYPE: RNA
<213> ORGANISM: Artificial Sequence
<220> FEATURE:
<223> OTHER INFORMATION: Synthetic 5'UTR

<400> SEQUENCE: 59
uacaucacaa ucacacaaaa cuaacaaaag aucaaaagca aguucuucac uguugaua    58

<210> SEQ ID NO 60
<211> LENGTH: 32
<212> TYPE: RNA
<213> ORGANISM: Artificial Sequence
<220> FEATURE:
<223> OTHER INFORMATION: Synthetic predicted sequence
<220> FEATURE:
<221> NAME/KEY: misc_feature
<222> LOCATION: (8)..(11)
<223> OTHER INFORMATION: n is a, c, g, or u

<400> SEQUENCE: 60
uuaaaaannn nacaaaaaaa aaaaaaaaaa aa                                32

<210> SEQ ID NO 61
<211> LENGTH: 30
<212> TYPE: DNA
<213> ORGANISM: Artificial Sequence
<220> FEATURE:
<223> OTHER INFORMATION: Synthetic primer

<400> SEQUENCE: 61
actctagaac acaagcattt tcaaggatat                                   30

<210> SEQ ID NO 62
<211> LENGTH: 28
<212> TYPE: DNA
<213> ORGANISM: Artificial Sequence
<220> FEATURE:
<223> OTHER INFORMATION: Synthetic primer

<400> SEQUENCE: 62
tgaggcctta acatattctc tcactata                                     28

<210> SEQ ID NO 63
<211> LENGTH: 30
<212> TYPE: DNA
<213> ORGANISM: Artificial Sequence
<220> FEATURE:
<223> OTHER INFORMATION: Synthetic primer

<400> SEQUENCE: 63
actctagacc tttcttgtcg tcgtttcgaa                                   30

```
<210> SEQ ID NO 64
<211> LENGTH: 30
<212> TYPE: DNA
<213> ORGANISM: Artificial Sequence
<220> FEATURE:
<223> OTHER INFORMATION: Synthetic primer

<400> SEQUENCE: 64
tgaggcctta acatcttctt ctccgattct                              30

<210> SEQ ID NO 65
<211> LENGTH: 30
<212> TYPE: DNA
<213> ORGANISM: Artificial Sequence
<220> FEATURE:
<223> OTHER INFORMATION: Synthetic primer

<400> SEQUENCE: 65
actctagagc gcctcttgcc atcttttgtc                              30

<210> SEQ ID NO 66
<211> LENGTH: 30
<212> TYPE: DNA
<213> ORGANISM: Artificial Sequence
<220> FEATURE:
<223> OTHER INFORMATION: Synthetic primer

<400> SEQUENCE: 66
tgaggcctta acattgtttc ctgtgaagat                              30

<210> SEQ ID NO 67
<211> LENGTH: 30
<212> TYPE: DNA
<213> ORGANISM: Artificial Sequence
<220> FEATURE:
<223> OTHER INFORMATION: Synthetic primer

<400> SEQUENCE: 67
actctagatt aaaaattgca caaaaaaaaa                              30

<210> SEQ ID NO 68
<211> LENGTH: 30
<212> TYPE: DNA
<213> ORGANISM: Artificial Sequence
<220> FEATURE:
<223> OTHER INFORMATION: Synthetic primer

<400> SEQUENCE: 68
tgaggcctta acattgtttc ctgttttttt                              30

<210> SEQ ID NO 69
<211> LENGTH: 21
<212> TYPE: DNA
<213> ORGANISM: Artificial Sequence
<220> FEATURE:
<223> OTHER INFORMATION: Synthetic primer

<400> SEQUENCE: 69
acacaagcat tttcaaggat a                                       21

<210> SEQ ID NO 70
<211> LENGTH: 21
<212> TYPE: DNA
<213> ORGANISM: Artificial Sequence
<220> FEATURE:
<223> OTHER INFORMATION: Synthetic primer
```

```
<400> SEQUENCE: 70
tacatcacaa tcacacaaaa c                                              21

<210> SEQ ID NO 71
<211> LENGTH: 21
<212> TYPE: DNA
<213> ORGANISM: Artificial Sequence
<220> FEATURE:
<223> OTHER INFORMATION: Synthetic primer

<400> SEQUENCE: 71
cctttcttgt cgtcgtttcg a                                              21

<210> SEQ ID NO 72
<211> LENGTH: 22
<212> TYPE: DNA
<213> ORGANISM: Artificial Sequence
<220> FEATURE:
<223> OTHER INFORMATION: Synthetic primer

<400> SEQUENCE: 72
gcgcctcttg ccatcttttg tc                                             22

<210> SEQ ID NO 73
<211> LENGTH: 37
<212> TYPE: DNA
<213> ORGANISM: Artificial Sequence
<220> FEATURE:
<223> OTHER INFORMATION: Synthetic primer

<400> SEQUENCE: 73
ttaaaaattg cacaaaaaaa aaaaaaaaaa aaacagg                             37

<210> SEQ ID NO 74
<211> LENGTH: 21
<212> TYPE: DNA
<213> ORGANISM: Artificial Sequence
<220> FEATURE:
<223> OTHER INFORMATION: Synthetic primer

<400> SEQUENCE: 74
ttctctccaa atgaaatgaa c                                              21

<210> SEQ ID NO 75
<211> LENGTH: 22
<212> TYPE: DNA
<213> ORGANISM: Artificial Sequence
<220> FEATURE:
<223> OTHER INFORMATION: Synthetic primer

<400> SEQUENCE: 75
ccttacgctg aagagatgct cg                                             22

<210> SEQ ID NO 76
<211> LENGTH: 22
<212> TYPE: DNA
<213> ORGANISM: Artificial Sequence
<220> FEATURE:
<223> OTHER INFORMATION: Synthetic primer

<400> SEQUENCE: 76
attcggtgat gataatcggc tg                                             22

<210> SEQ ID NO 77
```

```
<211> LENGTH: 20
<212> TYPE: DNA
<213> ORGANISM: Artificial Sequence
<220> FEATURE:
<223> OTHER INFORMATION: Synthetic primer

<400> SEQUENCE: 77
cgactcaaca gaagaatctg                                              20

<210> SEQ ID NO 78
<211> LENGTH: 20
<212> TYPE: DNA
<213> ORGANISM: Artificial Sequence
<220> FEATURE:
<223> OTHER INFORMATION: Synthetic primer

<400> SEQUENCE: 78
cgtatttgta accctattgc                                              20

<210> SEQ ID NO 79
<211> LENGTH: 22
<212> TYPE: DNA
<213> ORGANISM: Artificial Sequence
<220> FEATURE:
<223> OTHER INFORMATION: Synthetic primer

<400> SEQUENCE: 79
gagtattcgt tgcatcatca cc                                           22

<210> SEQ ID NO 80
<211> LENGTH: 21
<212> TYPE: DNA
<213> ORGANISM: Artificial Sequence
<220> FEATURE:
<223> OTHER INFORMATION: Synthetic primer

<400> SEQUENCE: 80
caaagtgaac atcatctgcg a                                            21

<210> SEQ ID NO 81
<211> LENGTH: 22
<212> TYPE: DNA
<213> ORGANISM: Artificial Sequence
<220> FEATURE:
<223> OTHER INFORMATION: Synthetic primer

<400> SEQUENCE: 81
cggccgtaag gttctgttaa at                                           22

<210> SEQ ID NO 82
<211> LENGTH: 20
<212> TYPE: DNA
<213> ORGANISM: Artificial Sequence
<220> FEATURE:
<223> OTHER INFORMATION: Synthetic primer

<400> SEQUENCE: 82
ccatccgacg tggactcaac                                              20

<210> SEQ ID NO 83
<211> LENGTH: 20
<212> TYPE: DNA
<213> ORGANISM: Artificial Sequence
<220> FEATURE:
<223> OTHER INFORMATION: Synthetic primer

<400> SEQUENCE: 83
```
atggctgagg ctgatgatat                                                    20

<210> SEQ ID NO 84
<211> LENGTH: 26
<212> TYPE: DNA
<213> ORGANISM: Artificial Sequence
<220> FEATURE:
<223> OTHER INFORMATION: Synthetic primer

<400> SEQUENCE: 84
ttagaaacat tttctgtgaa cgattc                                             26

<210> SEQ ID NO 85
<211> LENGTH: 21
<212> TYPE: RNA
<213> ORGANISM: Arabidopsis thaliana

<400> SEQUENCE: 85
uucaaggaua ucaaaucaca a                                                  21

<210> SEQ ID NO 86
<211> LENGTH: 21
<212> TYPE: RNA
<213> ORGANISM: Arabidopsis thaliana

<400> SEQUENCE: 86
cacacaaaac uaacaaaaga u                                                  21

<210> SEQ ID NO 87
<211> LENGTH: 21
<212> TYPE: RNA
<213> ORGANISM: Arabidopsis thaliana

<400> SEQUENCE: 87
caagcauugg auuaaucaaa g                                                  21

<210> SEQ ID NO 88
<211> LENGTH: 7
<212> TYPE: RNA
<213> ORGANISM: Arabidopsis thaliana

<400> SEQUENCE: 88 auuaaca                                                                   7

<210> SEQ ID NO 89
<211> LENGTH: 21
<212> TYPE: RNA
<213> ORGANISM: Arabidopsis thaliana

<400> SEQUENCE: 89
aaccgaaaaa agaaaaaaac u                                                  21

<210> SEQ ID NO 90
<211> LENGTH: 16
<212> TYPE: RNA
<213> ORGANISM: Artificial Sequence
<220> FEATURE:
<223> OTHER INFORMATION: Synthetic 5'UTR

<400> SEQUENCE: 90 cacggggggac ucuaga                                                       16